US007964181B2

(12) United States Patent
Sharma et al.

(10) Patent No.: US 7,964,181 B2
(45) Date of Patent: *Jun. 21, 2011

(54) AMINO ACID SURROGATES FOR PEPTIDIC CONSTRUCTS

(75) Inventors: Shubh D. Sharma, Cranbury, NJ (US); Margarita Bastos, Plainsboro, NJ (US); Wei Yang, Edison, NJ (US); Hui-Zhi Cai, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 484 days.

This patent is subject to a terminal disclaimer.

(21) Appl. No.: 11/694,181

(22) Filed: Mar. 30, 2007

(65) Prior Publication Data

US 2007/0260040 A1    Nov. 8, 2007

Related U.S. Application Data

(60) Provisional application No. 60/743,963, filed on Mar. 30, 2006, provisional application No. 60/743,964, filed on Mar. 30, 2006, provisional application No. 60/743,960, filed on Mar. 30, 2006, provisional application No. 60/743,961, filed on Mar. 30, 2006.

(51) Int. Cl.
   *A61K 31/785*    (2006.01)
   *A61K 47/16*     (2006.01)
   *A61K 38/02*     (2006.01)
   *A01N 43/34*     (2006.01)

(52) U.S. Cl. ...... 424/78.14; 424/1.69; 514/43; 530/332; 530/333

(58) Field of Classification Search .......................... None
See application file for complete search history.

(56) References Cited

U.S. PATENT DOCUMENTS

| 4,251,438 | A |   | 2/1981  | Moon              |           |
|-----------|---|---|---------|-------------------|-----------|
| 4,341,698 | A |   | 7/1982  | Carr et al.       |           |
| 5,559,232 | A |   | 9/1996  | Ackermann et al.  |           |
| 5,929,237 | A |   | 7/1999  | Kahn              |           |
| 6,013,458 | A |   | 1/2000  | Kahn et al.       |           |
| 6,184,223 | B1|   | 2/2001  | Kahn et al.       |           |
| 6,413,963 | B2|   | 7/2002  | Kahn et al.       |           |
| 6,462,046 | B2| * | 10/2002 | Lou et al.        | 514/253.01|
| 6,943,157 | B2|   | 9/2005  | Nagula et al.     |           |
| 7,008,941 | B2|   | 3/2006  | Urban et al.      |           |
| 2002/0111348 | A1 | | 8/2002 | Reichard et al.   |           |
| 2003/0019049 | A9 | | 1/2003 | Kravtchenko et al.|           |
| 2004/0224957 | A1 | | 11/2004| Sharma            |           |
| 2006/0217532 | A1 | | 9/2006 | Miao et al.       |           |
| 2006/0234923 | A1 | | 10/2006| Zumbrunn et al.   |           |

FOREIGN PATENT DOCUMENTS

| DE | 3022401      |   | 1/1981  |
|----|--------------|---|---------|
| FR | 2717484      |   | 9/1995  |
| WO | WO 92/21361  |   | 12/1992 |
| WO | WO 99/43662  | * | 9/1999  |
| WO | WO 99/48913  |   | 9/1999  |
| WO | WO 99/55684  |   | 11/1999 |
| WO | WO-02/85925  | * | 10/2002 |
| WO | WO 02/085925 |   | 10/2002 |
| WO | WO 2007/115175|  | 10/2007 |
| WO | WO 2007/115182|  | 10/2007 |

OTHER PUBLICATIONS

Tong, 1998, Bioorganic and Medicinal Chemistry Letters, 8, 1679-1682.*
Su, 2003, Bioorganic and Medicinal Chemistry Letters, 13, 1679-1682.*
Mohammad, 1998, Tetrahedron Letters, 39, 8213-8216.*
Kolter, 1995, Liebigs Ann., 625-629.*
DiMaio, 1989, J. Chem. Soc. Perkin Trans, 1687-1689.*
Rubsam, 2000, Tetrahedron, 56, 8481-8487.*
Goff, 1996, Tetrahedron Letters, 37, 6247-6250.*
Shigematsu, 1988, Tetrahedron Letters, 29, 5147-5150.*
Masuzawa, et al., The Reaction of C-Substituted Ethylenediamine with the Ester of Alpha-Halo Acid, vol. 38, No. 12, 2078-2081 (1965).
PCT International Preliminary Report on Patentability in PCT/US2007/065632 dated Mar. 3, 2009.
S.M. Hecht, Bioorganic Chemistry: Peptides and Proteins, Oxford University Press, 1998, 395-419.
Rubsam, F., et al., Synthesis of chiral piperazinones as versatile scaffolds for peptidomimetics, Tetrahedron, 2000, 56(43) 8481-8487.
Kolter, T., et al., Synthesis of substituted chiral piperazinones as building blocks for peptidomimetics, Liebigs Annalen, 1995, 4, 625-629.
DiMaio, John, et al., Synthesis of Chiral Piperazin-2-ones as Model Peptidomimetics, J. Chem. Soc., 1989, 1687-1689.
Dutta, A.S., Potent Cyclic Monomeric and Dimeric Peptide, etc., Journal of Peptide Science, 2000, vol. 6, pp. 321-341, especially pp. 323-325, Table 1, compounds 47-58.
de Visser, Solid-phase synthesis of polymyxin B1 and analogues via, etc. P.C.J. Peptide Res., 2003, vol. 61, pp. 298-306, especially p. 303, Table 1, compounds 27-28.

(Continued)

*Primary Examiner* — Andrew D Kosar
*Assistant Examiner* — Satyanarayana R Gudibande
(74) *Attorney, Agent, or Firm* — Stephen A. Slusher

(57) ABSTRACT

Ring-constrained amino acid surrogates of formula I:

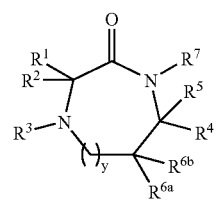

where $R^1$, $R^2$, $R^3$, $R^4$, $R^5$, $R^{6a}$, $R^{6b}$, $R^7$, and y are as defined in the specification, methods for synthesizing ring-constrained amino acid surrogates of formula I, methods of use of ring-constrained amino acid surrogates of formula I, including use in linear or cyclic compounds which include a plurality of amino acid residues and one or more ring-constrained amino acid surrogates of formula I and linear or cyclic compounds which include a plurality of amino acid residues and one or more ring-constrained amino acid surrogates of formula I.

35 Claims, No Drawings

OTHER PUBLICATIONS

Masuzawa et al., The Reaction of C-Substituted Ethylenediamine with the Ester of Alpha-Halo Acid, Apr. 1965, vol. 38, No. 12, pp. 2078-2081.

Shreder, K., et al, "Synthesis of a Constrained Enkephalin Analog to Illustrate a Novel Route to the Piperazinone Ring Structure", Tetrahedron Letters, Elsevier, Amsterdam vol. 39, No. 3-4, Jan. 15, 1998, pp. 221-224, ISSN: 0040-4039.

Communication from European Patent Office in European Patent Application 07759821.7, dated Oct. 2, 2009, and including Supplementary European Search Report and European Search Opinion.

Goff D.A., et al: Tetrahedron Letters, Elsevier, Amsterdam, NL Lnkd.—DOI:10.1016/0040-4039(96)01382-2, vol. 37, No. 35, Aug. 26, 1996, pp. 6247-6250.

Shigematsu, N., et al.: "Structure and Synthesis of FR-900490 A New Immunomodulating Peptide Isolated From A Fungus" Tetrahedron Letters, vol. 29, No. 40, 1988, pp. 5147-5150.

Communication pursuant to Article 94(3) EPC in European Application No. 07759821.7, Jun. 8, 2010.

* cited by examiner ns. 7,008,941, 6,943,157, 6,413,963, 6,184,223, 6,013,458 and 5,929,237, and U.S. Published Patent Application 2006/0084655, all describing various bicyclic ring structures asserted to mimic a dipeptide or tripeptide sequence. Other applications disclose a number of different small molecule compounds, again asserted to mimic a dipeptide or tripeptide sequence. See, for example, U.S. Published Patent Applications 2006/0234923 and 2003/0191049.

AMINO ACID SURROGATES FOR PEPTIDIC CONSTRUCTS

CROSS-REFERENCE TO RELATED APPLICATIONS

This application claims priority to and the benefit of the filing of U.S. Provisional Patent Application Ser. No. 60/743,963 entitled "Linear Natriuretic Peptide Constructs", filed on Mar. 30, 2006, of U.S. Provisional Patent Application Ser. No. 60/743,964 entitled "Linear Natriuretic Peptide Constructs with Prosthetic Groups", filed on Mar. 30, 2006, of U.S. Provisional Patent Application Ser. No. 60/743,960 entitled "Cyclic Natriuretic Peptide Constructs", filed on Mar. 30, 2006, and of U.S. Provisional Patent Application Ser. No. 60/743,961 entitled "Cyclic Natriuretic Peptide Constructs with Prosthetic Groups", filed on Mar. 30, 2006, and the specification and claims thereof of each are incorporated herein by reference.

Two related applications are being filed concurrently herewith, U.S. patent application Ser. No. 11/694,358, entitled "Linear Natriuretic Peptide Constructs" and U.S. patent application Ser. No. 11/694,260, entitled "Cyclic Natriuretic Peptide Constructs", and the specification and claims thereof are incorporated herein by reference.

BACKGROUND OF THE INVENTION

1. Field of the Invention (Technical Field)

The present invention relates to ring-constrained amino acid surrogates, methods for synthesizing ring-constrained amino acid surrogates, and methods of use of ring-constrained amino acid surrogates, including use in linear or cyclic constructs or compounds which include a plurality of amino acid residues and one or more ring-constrained amino acid surrogates.

2. Background Art

Amino Acid Surrogates. A number of different peptide mimetics are known, and are employed to make mimetics of critical function domains of peptides. See generally *Bioorganic Chemistry: Peptides and Proteins*, S. M. Hecht, ed., Oxford University Press, 1998, and particularly Chapter 12 thereof, pages 395-419, and the references cited therein. Peptides and proteins are highly flexible, due in large part to the high rotational degrees of freedom of individual amino acid residues. In addition, some bonds in side chains of individual amino acid residues also have rotational degrees of freedom. The non-bonded steric interactions between amino acid residues force the peptide or protein along its degrees of freedom into some stable minimal free energy configuration. Local structures, also known as a "secondary structure," are common in peptides and proteins. These structures include α-helixes, β-bends, sheets, extended chains, loops and the like, and most often contribute to binding or receptor-specificity of peptides and proteins. There are several types of α-helixes known, differing in torsion angles within the amino acid residues of the actual turn and by the patterns of intra- and inter-molecular hydrogen bonding. There are also a number of known different β-bends, differing in the dihedral torsion angles ψ (for the $C^α$—C bond) or φ (for the $C^α$—N bond), or both. Peptide mimetics are employed to provide a conformationally restricted component in a molecule, in part with the objective of fixing critical function domains in a restricted configuration that is optimal for a desired biological response.

Typically peptide mimetics are designed and intended to fix and mimic the function of a dipeptide or tripeptide. For example, see the reverse-turn mimetics disclosed in U.S. Pat.

Natriuretic Peptide System. One potential application for amino acid surrogates employs the natriuretic peptide system, which has been extensively explored since the identification of the human atrial natriuretic peptide (ANP) sequence and gene structure in 1984. ANP is part of the natriuretic peptide system, which in humans involves an ANP gene, which through differences in post-translational processing results in both ANP and urodilatin, a gene which produces BNP, or brain natriuretic peptide, and a gene which produces CNP, or c-type natriuretic peptide. ANP, urodilatin, BNP and CNP are each ring structures, with a 17 amino acid loop formed by a cysteine-cysteine disulfide linkage. The amino acid sequence and structure of human ANP (hANP) is shown in FIG. 1. ANP, urodilatin, BNP and CNP are closely related, differing by some five or six amino acids within the ring, though the N- and C-terminal tails are substantially different.

ANP, BNP and CNP are each specific for distinct receptors, natriuretic peptide receptors A, B and C (NPRA, NPRB and NPRC). NPRA and NPRB are linked to guanylyl cyclases, while NPRC is a G-protein linked clearance receptor. ANP, BNP and CNP are the primary endogenous mammalian natriuretic peptides identified to date. However, there are a number of non-mammalian natriuretic peptides that have been identified and may have therapeutic application in mammals. These include salmon natriuretic or cardiac peptide (sCP), ventricular natriuretic peptide (VNP), a cardiac natriuretic peptide identified in eels and a variety of fish, dendroaspis natriuretic peptide (DNP), a natriuretic peptide identified in mamba snake venom, and three natriuretic-like peptides (TNP-a, TNP-b, and TNP-c) isolated from taipan snake venom. See generally Tervonen V, Ruskoaho H, Lecklin T, lives M, Vuolteenaho O, Salmon cardiac natriuretic peptide is a volume-regulating hormone. *Am. J. Physiol. Endocrinol. Metab.* 283:E353-61 (2002); Takei Y, Fukuzawa A, Itahara Y, Watanabe T X, Yoshizawa Kumagaye K, Nakajima K, Yasuda A, Smith M P, Duff D W, Olson K R. A new natriuretic peptide isolated from cardiac atria of trout, *Oncorhynchus mykiss*. *FEBS Lett.* 414:377-80 (1997); Schweitz H, Vigne P, Moinier D, Frelin C, Lazdunski M. A new member of the natriuretic peptide family is present in the venom of the green mamba (*Dendroaspis angusticeps*). *J. Biol. Chem.* 267:13928-32 (1992); Lisy O, Jougasaki M, Heublein D M, Schirger J A, Chen H H, Wennberg P W, Burnett J C. Renal actions of synthetic dendroaspis natriuretic peptide. *Kidney Int.* 56:502-8 (1999); and Fry B G, Wickramaratana J C, Lemme S, Beuve A, Garbers D, Hodgson W C, Alewood P. Novel natriuretic peptides from the venom of the inland (*Oxyuranus microlepidotus*): isolation, chemical and biological characterization. *Biochem. Biophys. Res. Comm.* 327:1011-1015 (2005).

ANP is endogenously secreted predominately in response to increased atrial pressure, but other factors, including cytokine receptor stimulation, may contribute to endogenous secretion. Once released, ANP is a hormonal regulator of blood pressure, sodium and fluid homeostasis, providing vasorelaxant effects, affecting cardiovascular remodeling, and the like. Thus ANP, including endogenous ANP, is effective in congestive heart failure and other cardiovascular disease, in part by providing a defense against a chronically activated reninangiotensin-aldosterone system. Circulating ANP is rapidly removed from the circulation by two mechanisms, binding to a natriuretic peptide receptor and enzymatic degradation.

Human ANP is also referred to as wild-type human ANP, hANP, ANP(1-28) and ANP(99-126) (the later referring to the relevant sequence within proANP(1-126), which is normally cleaved at Arg$^{98}$-Ser$^{99}$ in the C-terminal region during secretion). Hereafter human ANP is sometimes referred to as "hANP."

In general, natriuretic peptides and variants thereof are believed to have utility in the treatment of congestive heart failure, renal hypertension, acute kidney failure and related conditions, as well as any condition, disease or syndrome for which a diuretic, natriuretic and/or vasodilatory response would have a therapeutic or preventative effect. One review article describing natriuretic peptides, including ANP, and use of the natriuretic peptide system in heart failure is Schmitt M., Cockcroft J. R., and Frenneaux M. P. Modulation of the natriuretic peptide system in heart failure: from bench to bedside? *Clinical Science* 105:141-160 (2003).

A large number of ANP mimetics and variations have been made, some of which are substantially reduced in size from ANP. On ANP version that is reduced in size yet is biologically active is the 15-mer disulfide cyclic peptide H-Met-cyclo(Cys-His-Phe-Gly-Gly-Arg-Met-Asp-Arg-Ile-Ser-Cys)-Tyr-Arg-NH$_2$ (SEQ ID NO:1) as described in Li B, Tom J Y, Oare D, Yen R, Fairbrother W J, Wells J A, Cunningham B C. Minimization of a polypeptide hormone. *Science* 270: 1657-60 (1995). This 15-mer peptide is commonly referred to as "mini-ANP".

BRIEF SUMMARY OF THE INVENTION

In one aspect, the invention provides a ring-constrained amino acid surrogate of the general formula I:

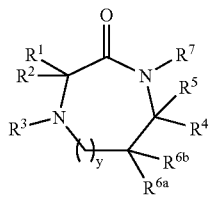

I or an enantiomer, stereoisomer or diastereoisomer thereof, or a synthetically acceptable salt thereof, wherein:

$R^1$ is H, alkyl, aryl, alkylaryl, alkyl-N(R$^8$)$_2$, alkyl-OR$^8$, alkyl-C(=O)OR$^8$, C(=O)OR$^8$, alkyl-NH$_2$, alkyl-S—R$^8$ alkyl-C(=O)N(R$^8$)$_2$, or a group of a formula:

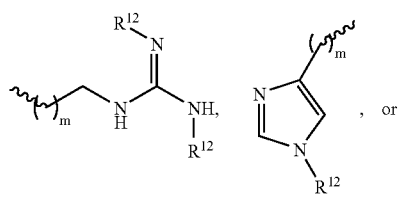

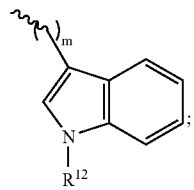

$R^2$ is H or alkyl, provided that $R^1$ and $R^2$ are not both H;
$R^3$ is H or a first nitrogen protecting group;
$R^4$ is H, alkyl, (CH$_2$)$_m$C(=O)OH, (CH$_2$)$_m$C(=O)N(H)R$^{11}$, (CH$_2$)$_m$C(=O)OR$^{11}$, (CH$_2$)$_q$OH, (CH$_2$)$_q$OBn, (CH$_2$)$_q$Oallyl, (CH$_2$)$_m$C(=O)N(R$^8$)$_2$, or (CH$_2$)$_m$C(=O)N(R$^8$)(CH$_2$)$_p$N(R$^8$)$_2$;
$R^5$ is H or alkyl;
$R^{6a}$ is H, alkyl, (CH$_2$)$_m$C(=O)OH, (CH$_2$)$_m$C(=O)N(H)R$^{11}$, (CH$_2$)$_m$C(=O)OR$^{11}$, (CH$_2$)$_q$OH, (CH$_2$)$_q$OBn, (CH$_2$)$_q$Oallyl, (CH$_2$)$_m$C(=O)N(R$^8$)$_2$, or (CH$_2$)$_m$C(=O)N(R$^8$)(CH$_2$)$_p$N(R$^8$)$_2$;
$R^{6b}$ is H or alkyl;
provided that both of $R^4$ and $R^{6a}$ are not (CH$_2$)$_m$C(=O)OH, (CH$_2$)$_m$C(=O)N(H)R$^{11}$, (CH$_2$)$_m$C(=O)OR$^{11}$, (CH$_2$)$_q$OH, (CH$_2$)$_q$OBn, (CH$_2$)$_q$Oallyl, (CH$_2$)$_m$C(=O)N(R$^8$)$_2$, or (CH$_2$)$_m$C(=O)N(R$^8$)(CH$_2$)$_p$N(R$^8$)$_2$;
$R^7$ is H, C(=O)alkyl, C(=O)(CH$_2$)$_m$(NR$^8$)$_2$, alkyl, aralkyl, or aryl;
each occurrence of $R^8$ is independently H, aryl, or alkyl;
$R^{11}$ is a peptide solid support;
$R^{12}$ is H or a second nitrogen protecting group;
each occurrence of m is an independent integer having a value between 0 and 6;
each occurrence of q is an independent integer having a value between 1 and 6;
p is an integer having a value between 1 and 10; and
y is 0 or 1.

In one aspect of the surrogate of general formula I, y is 1. In another aspect, y is 0.

In one aspect of the surrogate of general formula I, $R^4$ is (CH$_2$)$_m$C(=O)OH, (CH$_2$)$_m$C(=O)N(R$^8$)$_2$, or (CH$_2$)$_m$C(=O)N(H)R$^{11}$, (CH$_2$)$_m$C(=O)OR$^{11}$ and $R^{6a}$ is H or alkyl.

In one aspect of the surrogate of general formula I, $R^{6a}$ is (CH$_2$)$_m$C(=O)OH, (CH$_2$)$_m$C(=O)N(R$^8$)$_2$, or (CH$_2$)$_m$C(=O)N(H)R$^{11}$, (CH$_2$)$_m$C(=O)OR$^{11}$ and $R^4$ is H or alkyl.

In one aspect of the surrogate of general formula I, $R^3$ is a group of a formula:

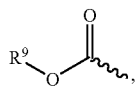

and $R^9$ is tert-butyl, allyl, or a group of a formula:

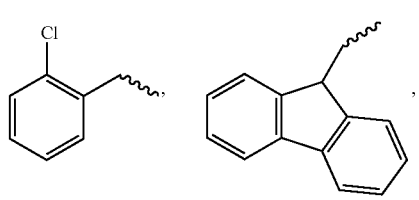

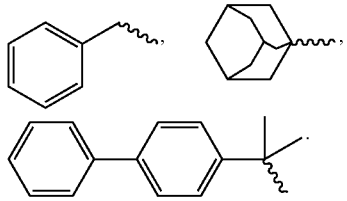

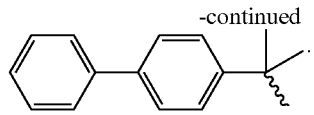

In one aspect of the surrogate of general formula I, $R^1$ is alkyl-$N(R^8)_2$, alkyl-$OR^8$, $(CH_2)_m$—C(=O)$OR^8$, C(=O)$OR^8$, alkyl-$NH_2$, alkyl-S—$R^8$, alkyl-C(=O)$N(R^8)_2$, or a group of the formula:

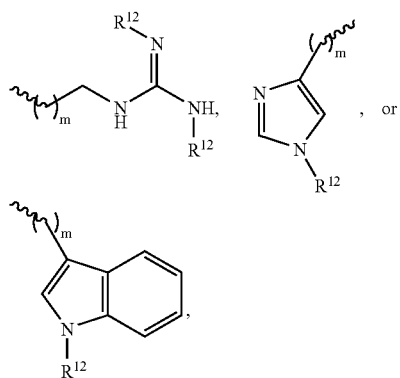

and $R^{12}$ is H or triphenylmethylene, tert-butyloxycarbonyl, toluenesulphonyl, formyl, nitro or benzyloxycarbonyl and n is an integer having a value between 2 and 6.

In one aspect of the surrogate of general formula I, there is provided a compound having a formula:

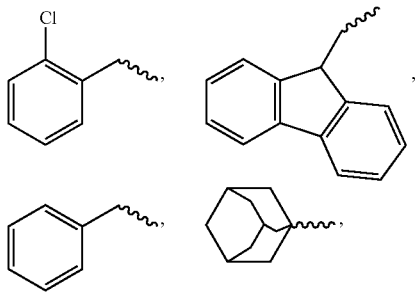

or an enantiomer, stereoisomer or diastereoisomer thereof, or a synthetically acceptable salt thereof, wherein:

$R^{6a}$ is H or alkyl; and
$R^9$ is tert-butyl, allyl, or a group of a formula:

In the foregoing, $R^1$ can be alkyl-$N(R^8)_2$, alkyl-$OR^8$, $(CH_2)_m$—C(=O)$OR^8$, C(=O)$OR^8$, alkyl-$NH_2$, alkyl-S—$R^8$, alkyl-C(=O)$N(R^8)_2$, or a group of the formula:

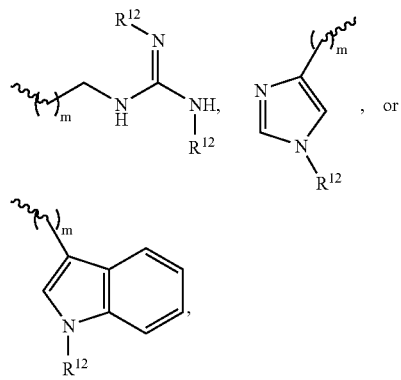

where $R^{12}$ is H or triphenylmethylene, tert-butyloxycarbonyl, toluenesulphonyl, formyl, nitro or benzyloxycarbonyl and n is an integer having a value between 2 and 6. $R^7$ can be H. $R^4$ can be $(CH_2)_mC$(=O)OH, $(CH_2)_mC$(=O)$N(R^8)_2$, $(CH_2)_mC$(=O)N(H)$R^{11}$, or $(CH_2)_mC$(=O)$OR^{11}$.

In one aspect of the surrogate of general formula I, there is provided a compound having a formula:

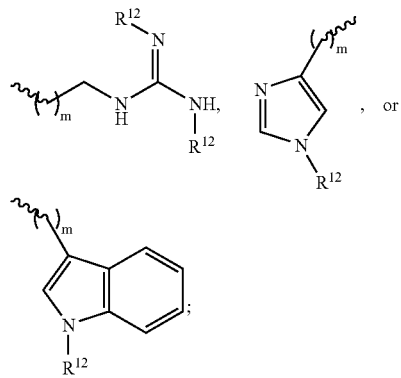

or an enantiomer, stereoisomer or diastereoisomer thereof, or a synthetically acceptable salt thereof, wherein:
$R^1$ is alkyl-$N(R^8)_2$, alkyl-$OR^8$, $(CH_2)_m$—C(=O)$OR^8$, C(=O)$OR^8$, alkyl-$NH_2$, alkyl-S—$R^8$, alkyl-C(=O)$N(R^8)_2$, or the group of the formula:

where R⁴ is (CH₂)ₘC(=O)OH, (CH₂)ₘC(=O)N(H)R¹¹, (CH₂)ₘC(=O)OR¹¹, (CH₂)ᵩOH, (CH₂)ᵩOBn, (CH₂)ᵩOallyl, (CH₂)ₘC(=O)N(R⁸)₂, or (CH₂)ₘC(=O)N(R⁸)(CH₂)ₚN(R⁸)₂; R⁶ᵃ is H or alkyl; and n is an integer having a value between 2 and 6.

In the foregoing, R¹ can be alkyl-N(R⁸)₂, alkyl-OR⁸, (CH₂)ₘ—C(=O)OR⁸, C(=O)OR⁸, alkyl-NH₂, alkyl-S—R⁸, alkyl-C(=O)N(R⁸)₂, or a group of the formula:

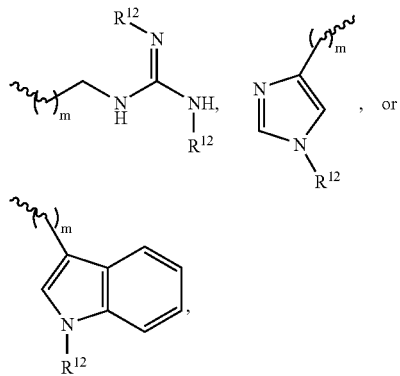

where R¹² is H or triphenylmethylene, tert-butyloxycarbonyl, toluenesulphonyl, formyl, nitro or benzyloxycarbonyl and n is an integer having a value between 2 and 6. R⁷ can be H. R⁴ can be (CH₂)ₘC(=O)OH, (CH₂)ₘC(=O)N(R⁸)₂, (CH₂)ₘC(=O)N(H)R¹¹, or (CH₂)ₘC(=O)OR¹¹.

In one aspect of the surrogate of general formula I, there is provided a compound having a formula:

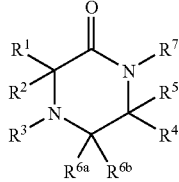

or an enantiomer, stereoisomer or diastereoisomer thereof, or a synthetically acceptable salt thereof, wherein:
R¹ is alkyl-N(R⁸)₂, (CH₂)ₘOR⁸, (CH₂)ₘ—C(=O)OR⁸, C(=O)OR⁸, alkyl-NH₂, alkyl-S—R⁸, alkyl-C(=O)N(R⁸)₂, or a group of the formula:

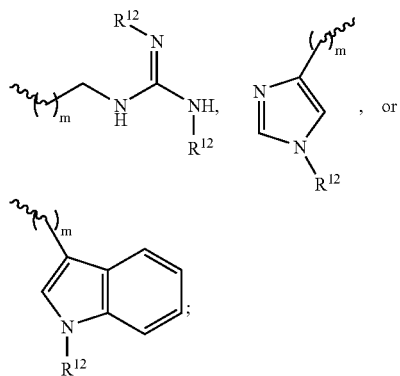

R⁴ is H or alkyl;
R⁶ᵃ is H or alkyl; and n is an integer having a value between 2 and 6.

In the foregoing, R³ can be a group of a formula:

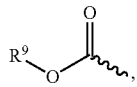

and R⁹ can be tert-butyl, allyl, or a group of a formula:

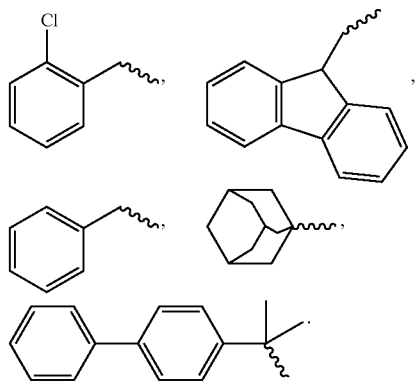

R¹ can be alkyl-N(R⁸)₂, alkyl-OR⁸, (CH₂)ₘ—C(=O)OR⁸, C(=O)OR⁸, alkyl-NH₂, alkyl-S—R⁸, alkyl-C(=O)N(R⁸)₂, or a group of the formula:

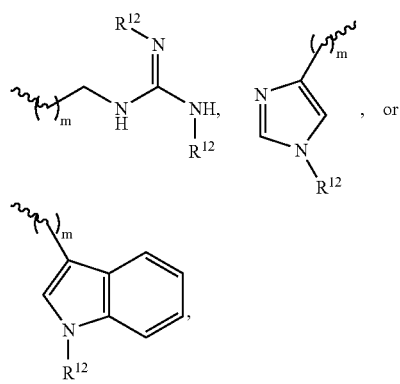

where R¹² is H or, toluenesulphonyl, formyl, nitro or benzyloxycarbonyl and n is an integer having a value between 2 and 6. R⁷ can be H.

In one aspect of the surrogate of general formula I, there is provided a compound having a formula:

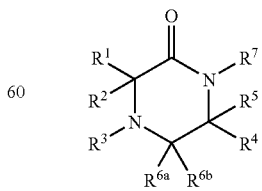

or an enantiomer, stereoisomer or diastereoisomer thereof, or a synthetically acceptable salt thereof, wherein:

$R^1$ is alkyl-N$(R^8)_2$, alkyl-OR$^8$, (CH$_2$)$_m$—C(=O)OR$^8$, C(=O)OR$^8$, alkyl-NH$_2$, alkyl-S—R$^8$, alkyl-C(=O)N$(R^8)_2$, or a group of a formula:

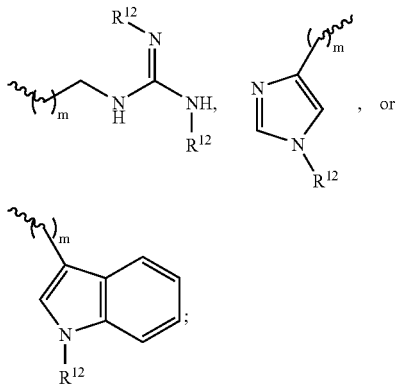

$R^4$ is H or alkyl; and $R^{6a}$ is (CH$_2$)$_m$C(=O)OH, (CH$_2$)$_m$C(=O)N(H)R$^{11}$, (CH$_2$)$_q$OH, (CH$_2$)$_q$OBn, (CH$_2$)$_q$Oallyl, (CH$_2$)$_m$C(=O)N$(R^8)_2$, or (CH$_2$)$_m$C(=O)N(R$^8$)(CH$_2$)$_p$N$(R^8)_2$.

In the foregoing, $R^3$ can be a group of a formula:

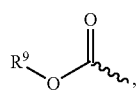

and $R^9$ can be tert-butyl, allyl, or a group of a formula:

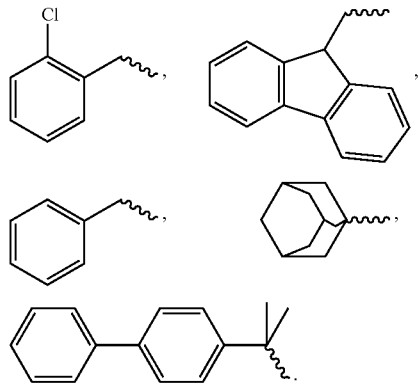

In the foregoing, $R^1$ can be alkyl-N$(R^8)_2$, alkyl-OR$^8$, (CH$_2$)$_m$—C(=O)OR$^8$, C(=O)OR$^8$, alkyl-NH$_2$, alkyl-S—R$^8$, alkyl-C(=O)N$(R^8)_2$, or a group of the formula:

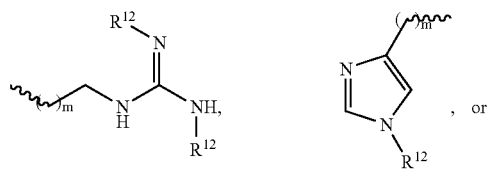

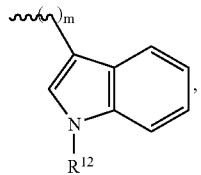

where R$^{12}$ is H or triphenylmethylene, tert-butyloxycarbonyl, toluenesulphonyl, formyl, nitro or benzyloxycarbonyl. R$^{6a}$ can be (CH$_2$)$_m$C(=O)OH, (CH$_2$)$_m$C(=O)N$(R^8)_2$, (CH$_2$)$_m$C(=O)N(H)R$^{11}$, or (CH$_2$)$_m$C(=O)OR$^{11}$. R$^7$ can be H.

In one aspect of the surrogate of general formula I, there is provided a compound having a formula:

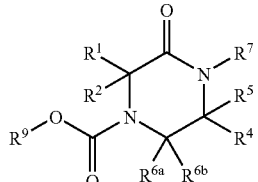

or an enantiomer, stereoisomer or diastereoisomer thereof, or a synthetically acceptable salt thereof, wherein:

$R^4$ is H or alkyl; and
$R^9$ is tert-butyl, allyl, or a group of a formula:

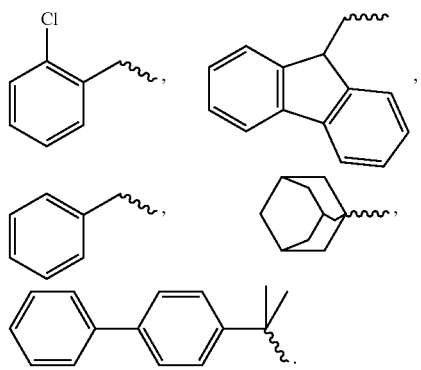

In the foregoing, $R^1$ can be alkyl-N$(R^8)_2$, alkyl-OR$^8$, (CH$_2$)$_m$—C(=O)OR$^8$, C(=O)OR$^8$, alkyl-NH$_2$, alkyl-S—R$^8$, alkyl-C(=O)N$(R^8)_2$, or a group of the formula:

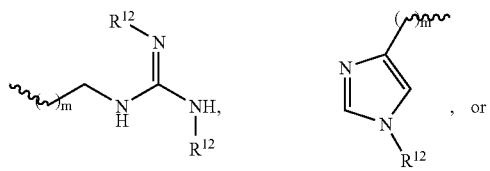

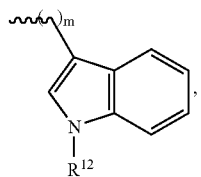

where $R^{12}$ is H or triphenylmethylene, tert-butyloxycarbonyl, toluenesulphonyl, formyl, nitro or benzyloxycarbonyl and n is an integer having a value between 2 and 6. $R^7$ can be H. $R^4$ can be $(CH_2)_mC(=O)OH$, $(CH_2)_mC(=O)N(R^8)_2$, $(CH_2)_mC(=O)N(H)R^{11}$, or $(CH_2)_mC(=O)OR^{11}$.

In one aspect of the surrogate of general formula I, there is provided a compound having a formula:

or an enantiomer, stereoisomer or diastereoisomer thereof, or a synthetically acceptable salt thereof, wherein:

$R^1$ and $R^2$ are independent alkyl groups.

In the foregoing, $R^3$ can be a group of a formula:

where $R^9$ is tert-butyl, allyl, or a group of a formula:

$R^4$ can be $(CH_2)_mC(=O)OH$, $(CH_2)_mC(=O)N(R^8)R^{11}$, or $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$ and $R^{6a}$ is H or alkyl. $R^{6a}$ can be $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$ and $R^4$ is H or alkyl. $R^7$ can be H.

In another embodiment, there is provided a method of synthesizing a peptide comprising a group of the formula:

said method comprising the step of reacting a compound having a formula of structure I:

or an enantiomer, stereoisomer or diastereoisomer thereof, or a synthetically acceptable salt thereof, with an N-protected amino acid,
wherein:
$R^1$ is H, alkyl, aryl, alkylaryl, alkyl-$N(R^8)_2$, alkyl-$OR^8$, alkyl-$C(=O)OR^8$, $C(=O)OR^8$, alkyl-$NH_2$, alkyl-S—$R^8$, alkyl-$C(=O)N(R^8)_2$, or a group of a formula:

$R^2$ is H or alkyl, provided that $R^1$ and $R^2$ are not both H;
$R^3$ is H or a first nitrogen protecting group;
$R^4$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^5$ is H or alkyl;
$R^{6a}$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^{6b}$ is H or alkyl;
provided that both of $R^4$ and $R^{6a}$ are not $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^7$ is H, $C(=O)$alkyl, $C(=O)(CH_2)_m(NR^8)_2$, alkyl, aralkyl, or aryl;
each occurrence of $R^8$ is independently H, aryl, or alkyl;
$R^{11}$ is a peptide solid support;
$R^{12}$ is H or a second nitrogen protecting group;
each occurrence of m is an independent integer having a value between 0 and 6;
each occurrence of q is an independent integer having a value between 1 and 6;
p is an integer having a value between 1 and 10; and
y is 0 or 1.

In one aspect of the invention, one amino acid surrogate may be employed in a compound of the invention, two amino acid surrogates may be employed in a compound of the invention, or more than two amino acid surrogates may be employed in a compound of the invention.

In another aspect of the invention, there is provided a compound including an amino acid surrogate wherein one or more peptide bonds between amino acid residues are substituted with a non-peptide bond.

In another aspect of the invention, there is provided a compound including at least one amino acid surrogate and a plurality of amino acid residues wherein the compound is a cyclic compound, cyclized by a bond between side chains of two amino acid residues, between an amino acid residue side chain and a group of an amino acid surrogate, between groups of two amino acid surrogates, between a terminal group of the compound and an amino acid residue side chain, or between a terminal group of the compound and a group of an amino acid surrogate.

Ring-constrained amino acid surrogates of formula I may be used to synthesize compounds wherein the compounds exhibit, upon administration to a mammal, one or more advantages relative to the corresponding amino acid sequence not comprising the amino acid surrogate of the invention, the advantages selected from the group consisting of increased resistance to enzymatic degradation, increased circulation half life, increased bioavailability, increased efficacy, prolonged duration of effect and combinations of the foregoing.

One object of the present invention is to provide ring-constrained amino acid surrogates of formula I which may be employed by substitution for an amino acid residue of a parent polypeptide.

Another object of the present invention is to provide a ring-constrained amino acid surrogate of formula I useful to synthesize a compound wherein the compound has an equilibrium receptor binding affinity, determined by the Ki (nM) value, less than the Ki (nM) value of the corresponding amino acid sequence not comprising an amino acid surrogate.

Another object of the present invention is to provide a ring-constrained amino acid surrogate of formula I useful to synthesize a compound wherein the compound has a receptor binding affinity with respect to a natriuretic peptide receptor greater than the receptor binding affinity of the corresponding amino acid sequence not comprising an amino acid surrogate.

Another object of the present invention is to provide a ring-constrained amino acid surrogate of formula I useful to synthesize a compound wherein the compound has biological efficacy at least as efficacious as or more efficacious than the same dose of the corresponding amino acid sequence not comprising an amino acid surrogate.

Another object of the present invention is to provide a ring-constrained amino acid surrogate of formula I useful to synthesize a compound wherein the compound has biological efficacy more efficacious than the same dose of the corresponding amino acid sequence not comprising an amino acid surrogate.

Another object of the present invention is to provide a ring-constrained amino acid surrogate of formula I useful to synthesize a compound wherein the corresponding amino acid sequence not comprising an amino acid surrogate has at least about 60% homology with the sequence of a parent polypeptide.

Another object of the present invention is to provide a ring-constrained amino acid surrogate of formula I useful to synthesize a compound wherein the corresponding amino acid sequence not comprising an amino acid surrogate has at least about 80% homology with the sequence of a parent polypeptide.

Another object of the present invention is to provide a ring-constrained amino acid surrogate of formula I useful to synthesize a compound wherein the corresponding amino acid sequence not comprising an amino acid surrogate has at least about 60% homology with the sequence of a peptide that binds to a receptor for ANP, BNP, CNP, sCP, DNP, TNP-a, TNP-b or TNP-c.

Another object of the present invention is to provide a ring-constrained amino acid surrogate of formula I useful to synthesize a natriuretic receptor-specific compound wherein the corresponding amino acid sequence not comprising an amino acid surrogate has at least about 80% homology with the sequence of a peptide that binds to a receptor for ANP, BNP, CNP, sCP, DNP, TNP-a, TNP-b or TNP-c.

Another object of the present invention is to provide a ring-constrained amino acid surrogate of formula I useful to synthesize a compound including a surrogate as defined herein wherein the corresponding amino acid sequence not comprising an amino acid surrogate is a parent polypeptide which binds to a known receptor.

Another object of the present invention is to provide ring-constrained amino acid surrogates of formula I useful to synthesize compounds with greater bioavailability and half-life than natural or recombinant forms of parent polypeptides.

Another object of the present invention is to provide ring-constrained amino acid surrogates of formula I useful to synthesize compounds with increased resistance to degradation but which have a significantly high binding affinity to its receptor.

Another object of the present invention is to provide a ring-constrained amino acid surrogates of formula I useful to synthesize compounds in a sustained release formulation.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

1. Definitions

"Alkyl Group"

As used herein, the term "alkyl group" means a saturated, monovalent, unbranched or branched hydrocarbon chain. Examples of alkyl groups include, but are not limited to, ($C_1$-$C_6$) alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or optionally substituted with one or two suitable substituents.

"Aliphatic"

As used herein, the term "aliphatic" includes compounds with hydrocarbon chains, such as for example alkanes, alkenes, alkynes, and derivatives thereof.

An "omega amino aliphatic" includes an aliphatic moiety with a terminal amino group. Examples of omega amino aliphatics include 7'-amino-heptanoyl and the amino acid side chain moieties of ornithine and lysine.

"Alkenyl Group"

As used herein, the term "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$) alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or optionally substituted with one or two suitable substituents.

"Alkynyl Group"

As used herein, the term "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or optionally substituted with one or two suitable substituents.

"Aralkyl"

The term "aralkyl" includes a radical—$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

"Aryl Group"

As used herein, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, naphthyl, 1-naphthyl, 2-naphthyl, and biphenyl as well as benzo-fused carbocyclic moieties such as 5,6,7,8-tetrahydronaphthyl. An aryl group can be unsubstituted or optionally substituted with one or two suitable substituents as defined below. An aryl group optionally may be fused to a cycloalkyl group, fused to another aryl group, fused to a heteroaryl group, or fused to a heterocycloalkyl group. Preferred aryl groups include, but are not limited to, monocyclic or bicyclic aromatic hydrocarbon radicals of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl.

In one embodiment, phenyl is a preferred aryl group, which when "substituted" independently comprises hydroxyl, halogen, alkyl, or aryl groups attached directly or through an ether linkage. Where the phenyl ring is so substituted, the amino acid residue may be referred to as substituted, as in substituted Phe, substituted HPhe or substituted Pgl.

"Heteroaryl Group"

As used herein, the term "heteroaryl group" means a monocyclic- or polycyclic aromatic ring comprising carbon atoms, hydrogen atoms, and one or more heteroatoms, preferably 1 to 4 heteroatoms, independently selected from nitrogen, oxygen, and sulfur. Illustrative examples of heteroaryl groups include, but are not limited to, pyridyl, pyridazinyl, pyrazyl, indolyl, triazinyl, pyrrolyl, pyrazolyl, imidazolyl, (1,2,3,)-triazolyl, (1,2,4)-triazolyl, pyrazinyl, pyrimidinyl, tetrazolyl, furyl, thienyl, isoxazolyl, thiazolyl, thiadiazolyl, furyl, phienyl, isoxazolyl, oxazolyl, pyrazolyl, tetrazolyl, triazolyl, oxadiazolyl, thiadiazolyl, isoxazolyl, triazinyl, and pyrazinyl. Bicyclic heteroaromatic rings include, but are not limited to, benzothiadiazolyl, indolyl, benzothiophenyl, benzofuryl, benzimidazolyl, benzisoxazolyl, benzothiazolyl, quinolinyl, benzotriazolyl, benzoxazolyl, isoquinolinyl, purinyl, furopyridinyl and thienopyridinyl. A heteroaryl can be unsubstituted or optionally substituted with one or two suitable substituents as defined below. A heteroaryl group optionally may be fused to another heteroaryl group, fused to an aryl group, fused to a cycloalkyl group, or fused to a heterocycloalkyl group.

"Cycloalkyl Group"

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or optionally substituted with one or two suitable substituents as defined below. A cycloalkyl group optionally may be fused to another cycloalkyl group, fused to an aryl group, fused to a heteroaryl group, or fused to a heterocycloalkyl group.

"Heterocycloalkyl Group"

As used herein, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur. A heterocycloalkyl group may be fused to an aryl or heteroaryl group. Examples of heterocycloalkyl groups include, but are not limited to, pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or optionally substituted with one or two suitable substituents as defined below. A heterocycloalkyl group optionally may be fused to a cycloalkyl group, fused to an aryl group, fused to a heteroaryl group, or fused to another heterocycloalkyl group.

For example, a heterocycloalkyl group can be fused to or substituted with an aryl group or heteroaryl group, for example, but not limited to, 1,2,3,4-tetrahydroisoquinolinyl and 1,2,3,4-tetrahydroquinolinyl, tetrahydronaphthyridinyl, phenylpiperidinyl, and piperidinylpyridinyl.

In a preferred embodiment, a heterocycloalkyl group is a monocyclic or bicyclic ring, more preferably, a monocyclic ring, wherein the ring comprises from 3 to 6 carbon atoms and form 1 to 3 heteroatoms, referred to herein as ($C_3$-$C_6$) heterocycloalkyl. In another preferred embodiment, a heterocycloalkyl group is fused to or substituted with an aryl group or a heteroaryl group.

"Heterocyclic Radical" or "Heterocyclic Ring"

As used herein, the terms "heterocyclic radical" or "heterocyclic ring" mean a heterocycloalkyl group or a heteroaryl group.

"Cyclic Radical"

As used herein, the term "cyclic radical" means an aryl group, a cycloalkyl group, a heterocycloalkyl group or a heteroaryl group.

"Alkoxy Group"

As used herein, the term "alkoxy group" means an —O-alkyl group, wherein alkyl is as defined above. An alkoxy group can be unsubstituted or optionally substituted with one or two suitable substituents. Preferably, the alkyl chain of an alkyloxy group is from 1 to 6 carbon atoms in length, referred to herein as "($C_1$-$C_6$)alkoxy".

"Aryloxy Group"

As used herein, the term "aryloxy group" means an —O-aryl group, wherein aryl is as defined above. An aryloxy group can be unsubstituted or optionally substituted with one or two suitable substituents. Preferably, the aryl ring of an aryloxy group is a monocyclic ring, wherein the ring comprises 6 carbon atoms, referred to herein as "(C₆)aryloxy.

"Alkoxycarbonyl"

As used herein, the term "alkoxycarbonyl" group means a monovalent group of the formula —C(=O)-alkoxy. Preferably, the hydrocarbon chain of an alkoxycarbonyl group is from 1 to 8 carbon atoms in length, referred to herein as a "lower alkoxycarbonyl" group.

"Carbamoyl"

As used herein, the term "carbamoyl" group means the radical —C(=O)N(R')₂, wherein R' is chosen from the group consisting of hydrogen, alkyl, and aryl.

"Carbonyl"

As used herein, a "carbonyl" group is a divalent group of the formula C(=O).

"Oxo"

As used herein, an "oxo" group is a group of the formula (=O).

"Acyl"

The term "acyl" includes a group R—C(=O)—, where R is an organic group. An example is the acetyl group CH₃—C(=O)—, referred to herein as "Ac".

A peptide or aliphatic moiety is "acylated" when an aryl, alkyl or substituted alkyl group as defined above is bonded through one or more carbonyl {—(C=O)—} groups. A peptide is most usually acylated at the N-terminus.

"Amide"

An "amide" includes compounds that have a trivalent nitrogen attached to a carbonyl group (—C(=O)—NH₂), such as for example methylamide, ethylamide, propylamide, and the like.

"Imide"

An "imide" includes compounds containing an imido group (—C(=O)—NH—C(=O)—).

"Amine"

An "amine" includes compounds that contain an amino group (—NH₂).

"Nitrile"

A "nitrile" includes compounds that are carboxylic acid derivatives and contain a (—CN) group bound to an organic group.

"Halogen"

As used herein, the term "halogen" means fluorine, chlorine, bromine, or iodine. Correspondingly, the meaning of the terms "halo" and "Hal" encompass fluoro, chloro, bromo, and iodo.

"Peptide Solid Support"

As used herein, the term "peptide solid support" means a synthetic polymer for use in peptide synthesis that bears reactive groups (free hydroxyl or amino groups), generally through a linker, that can react with the carboxyl group of an N-protected amino acid functionality or a surrogate of formula I, thereby covalently binding the amino acid or surrogate of formula I to the polymer. At the end of the peptide synthesis, the bond between the C-terminal amino acid or surrogate and the polymer support can be chemically cleaved. The peptide or compound including one or surrogates of formula I then goes into solution and can be isolated from the solution. Examples of peptide solid supports include, but are not limited to, polyamide resins and polystyrene resins with a suitable linker for solid phase synthesis. Examples of resins include Merrifield resins, BHA resins, MBHA resins, Wang resins, oxime resins and the like. Linkers that may be employed include Fmoc-Rink, Sieber linker, Weinreb linker, and the like.

"Nitrogen Protecting Group"

As used herein, the term "nitrogen protecting group" means a group that replaces an amino hydrogen for the purpose of protecting against side reactions and degradation during a reaction sequence, for example, during peptide synthesis. Solid phase peptide synthesis involves a series of reaction cycles comprising coupling the carboxy group of an N-protected amino acid or surrogate with the amino group of the peptide substrate, followed by chemically cleaving the nitrogen protecting group so that the next amino-protected synthon may be coupled. Nitrogen protecting groups useful in the invention include nitrogen protecting groups well known in solid phase peptide synthesis, including, but not limited to, t-Boc (tert-butyloxycarbonyl), Fmoc (9-flourenylmethyloxycarbonyl), 2-chlorobenzyloxycarbonyl, allyloxycarbonyl (alloc), benzyloxycarbonyl, 2-(4-biphenylyl)propyl-2-oxycarbonyl (Bpoc), 1-adamantyloxycarbonyl, trityl (triphenylmethyl), and toluene sulphonyl.

"Suitable Substituent"

As used herein, the term "suitable substituent" means a group that does not nullify the synthetic, therapeutic or pharmaceutical utility of the compounds of the invention or the intermediates useful for preparing them. Examples of suitable substituents include, but are not limited to: alkyl; alkenyl; alkynyl; aryl; heteroaryl; heterocycloalkyl; cycloalkyl; O-alkyl; O-alkenyl; O-alkynyl; O-aryl; CN; OH; oxo; halo; C(=O)OH; C(=O)halo; OC(=O)halo; CF₃; N₃; NO₂; NH₂; NH(alkyl); N(alkyl)₂; NH(aryl); N(aryl)₂; C(=O)NH₂; C(=O)NH(alkyl); C(=O)N(alkyl)₂; C(=O)NH(aryl); C(=O)N(aryl)₂; OC(=O)NH₂; C(=O)NH(heteroaryl); C(=O)N(heteroaryl)₂; NHOH; NOH(alkyl); NOH(aryl); OC(=O)NH(alkyl); OC(=O)N(alkyl)₂; OC(=O)NH(aryl); OC(=O)N(aryl)₂; CHO; C(=O)(alkyl); C(=O)(aryl); C(=O)O(alkyl); C(=O)O(aryl); OC(=O)(alkyl); OC(=O)(aryl); OC(=O)O(alkyl); OC(=O)O(aryl); S-alkyl; S-alkenyl; S-alkynyl; SC(=O)₂-aryl, SC(=O)₂-alkyl; SC(=O)₂-alkenyl; SC(=O)₂-alkynyl; and SC(=O)₂-aryl. One of skill in art can readily choose a suitable substituent based on the synthesis, stability and pharmacological activity of the compound of the invention.

The "∿∿∿"

As used herein in the chemical structure drawings, the above "wavy line" indicates a bond at the point that a chemical group is attached to another chemical group. Thus, according to this definition, the chemical formula "A" below:

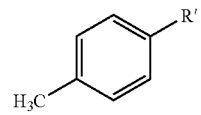

A wherein R' is a group of the formula "B",

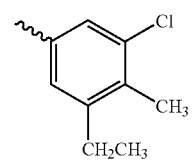

B represents the compound below

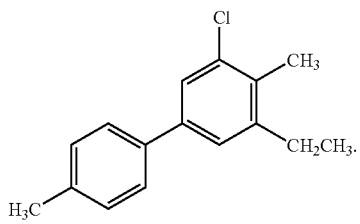

"Composition"

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"$EC_{50}$"

The term "$EC_{50}$" is intended to include the molar concentration of an agonist which produced 50% of the maximum possible response for that agonist. By way of example, a compound which, at a concentration of 72 nM, produces 50% of the maximum possible response for that compound as determined in a cGMP assay, has an $EC_{50}$ of 72 nM. Unless otherwise specified, the molar concentration associated with an $EC_{50}$ determination is in nanomoles (nM).

"Ki (nM)"

The term "Ki (nM)" is intended to include the equilibrium receptor binding affinity representing the molar concentration of a competing compound that binds to half the binding sites of a receptor at equilibrium in the absence of a competitor. In general, the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{EC_{50}}{1 + \frac{[\text{ligand}]}{K_d}}$$

where "ligand" is the concentration of ligand, which may be a radioligand, and $K_d$ is an inverse measure of receptor affinity which produces 50% receptor occupancy. Unless otherwise specified, the molar concentration associated with a Ki determination is nM.

"Peptide"

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, and the like. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

"Amino Acid Side Chain Moiety"

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative of an amino acid side chain moiety" as hereafter defined is included within the definition of an amino acid side chain moiety.

"Derivative of an Amino Acid Side Chain Moiety"

A "derivative of an amino acid side chain moiety" is a modification to or variation in any amino acid side chain moiety, including a modification to or variation in either a naturally occurring or unnatural amino acid side chain moiety, wherein the modification or variation includes: (a) adding one or more saturated or unsaturated carbon atoms to an existing alkyl, aryl, or aralkyl chain; (b) substituting a carbon in the side chain with another atom, preferably oxygen or nitrogen; (c) adding a terminal group to a carbon atom of the side chain, including methyl (—$CH_3$), methoxy (—$OCH_3$), nitro (—$NO_2$), hydroxyl (—OH), or cyano (—C≡N); (d) for side chain moieties including a hydroxy, thio or amino groups, adding a suitable hydroxy, thio or amino protecting group; or (e) for side chain moieties including a ring structure, adding one or ring substituents, including hydroxyl, halogen, alkyl, or aryl groups attached directly or through an ether linkage. For amino groups, suitable amino protecting groups include, but are not limited to, Z, Fmoc, Boc, Pbf, Pmc and the like.

"Amino Acids"

The "amino acids" used in embodiments of the present invention, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York (1992), the teachings of which are incorporated herein by reference, including the text and table set forth at pages 11 through 24. An "amino acid" includes conventional α-amino acids and further includes both β-amino acids and α,α-disubstituted amino acids wherein at least one side chain is an amino acid side chain moiety as defined herein. An "amino acid" further includes N-alkyl α-amino acids, wherein the N-terminus amino group has a $C_1$ to $C_6$ linear or branched alkyl substituent. It may thus be seen that the term "amino acid" includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F., Kazmierski W., *Biochem. J.* 268: 249-262 (1990); and Toniolo C., *Int. J. Peptide Protein Res.*

35:287-300 (1990); the teachings of all of which are incorporated herein by reference. In addition, the following abbreviations, including amino acids and protecting and modifying groups thereof, have the meanings given:

Abu—gamma-amino butyric acid
12-Ado—12-amino dodecanoic acid
Aib—alpha-aminoisobutyric acid
6-Ahx—6-amino hexanoic acid
Amc—4-(aminomethyl)-cyclohexane carboxylic acid
8-Aoc—8-amino octanoic acid
Bip—biphenylalanine
Boc—t-butoxycarbonyl
Bzl—benzyl
Bz—benzoyl
Dab—diaminobutyric acid
Dap—diaminopropionic acid
Dip—3,3-diphenylalanine
Disc-1,3-dihydro-2H-isoindolecarboxylic acid
Et—ethyl
Fmoc—fluorenylmethoxycarbonyl
Hept—heptanoyl($CH_3$—$(CH_2)_5$—C(=O)—)
Hex—hexanoyl($CH_3$—$(CH_2)_4$—C(=O)—)
HArg—homoarginine
HCys—homocysteine
HLys—homolysine
HPhe—homophenylalanine
HSer—homoserine
Me—methyl
Met(O)—methionine sulfoxide
Met($O_2$)—methionine sulfone
Nva—norvaline
Pgl-phenylglycine
Pr—propyl
Pr-i—isopropyl
Sar—sarcosine
Tle—tert-butylalanine
z—benzyloxycarbonyl In the listing of compounds according to the present invention, conventional amino acid residues have their conventional meaning as given in Chapter 2400 of the *Manual of Patent Examining Procedure*, 8th Ed. Thus, "Nle" is norleucine; "Asp" is aspartic acid; "His" is histidine; "Arg" is arginine; "Trp" is tryptophan; "Lys" is lysine; "Gly" is glycine; "Pro" is proline; "Tyr" is tyrosine, "Ser" is serine and so on. All residues are in the L-isomer configuration unless the D-isomer is specified, as in "D-Ala" for D-alanine.

A single amino acid, including stereoisomers and modifications of naturally occurring protein amino acids, non-protein amino acids, post-translationally modified amino acids, enzymatically synthesized amino acids, derivatized amino acids, an α,α-disubstituted amino acid derived from any of the foregoing (i.e., an α,α-disubstituted amino acid wherein at least one side chain is the same as that of the residue from which it is derived), a β-amino acid derived from any of the foregoing (i.e., a β-amino acid which other than for the presence of a β-carbon is otherwise the same as the residue from which it is derived) and the like, including all of the foregoing, is sometimes referred to herein as a "residue."

"α,α-Disubstituted Amino Acid"

An "α,α-disubstituted amino acid" includes any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α,α-disubstituted amino acid. While α,α-disubstituted amino acids can be referred to using conventional L- and D-isomeric references, it is to be understood that such references are for convenience, and that where the substituents at the α-position are different, such amino acid can interchangeably be referred to as an α,α-disubstituted amino acid derived from the L- or D-isomer, as appropriate, of a residue with the designated amino acid side chain moiety. Thus (S)-2-Amino-2-methylhexanoic acid can be referred to as either an α,α-disubstituted amino acid derived from L-Nle or as an α,α-disubstituted amino acid derived from D-Ala. Similarly, Aib can be referred to as an α,α-disubstituted amino acid derived from Ala. Whenever an α,α-disubstituted amino acid is provided, it is to be understood as including all (R) and (S) configurations thereof.

"N-Substituted Amino Acid"

An "N-substituted amino acid" includes any amino acid wherein an amino acid side chain moiety is covalently bonded to the backbone amino group, optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl.

"C-Terminus Capping Group"

The term "C-terminus capping group" includes any terminal group attached through the terminal ring carbon atom or, if provided, terminal carboxyl group, of the C-terminus of a compound. The terminal ring carbon atom or, if provided, terminal carboxyl group, may form a part of a residue, or may form a part of an amino acid surrogate. In a preferred aspect, the C-terminus capping group forms a part of an amino acid surrogate which is at the C-terminus position of the compound. The C-terminus capping group includes, but is not limited to, —$(CH_2)_n$—OH, —$(CH_2)_n$—C(=O)—OH, —$(CH_2)_m$—OH, —$(CH_2)_n$—C(=O)—N($v_1$)($v_2$), —$(CH_2)_n$—C(=O)—$(CH_2)_m$—N($v_1$)($v_2$), —$(CH_2)_n$—O—$(CH_2)_m$—$CH_3$, —$(CH_2)$—C(=O)—NH—$(CH_2)_m$—$CH_3$, —$(CH_2)_n$—C(=O)—NH—$(CH_2)_m$—N($v_1$)($v_2$), —$(CH_2)_n$—C(=O)—N—(($CH_2)_m$—N($v_1$)($v_2$))$_2$, —$(CH_2)_n$—C(=O)—NH—CH(—C(=O)—OH)—$(CH_2)_m$—N($v_1$)($v_2$), —C(=O)—NH—$(CH_2)_m$—NH—C(=O)—CH(N($v_1$)($v_2$))(($CH_2)_m$—N($v_1$)($v_2$)), or —$(CH_2)_n$—C(=O)—NH—CH(—C(=O)—$NH_2$)—$(CH_2)_m$—N($v_1$)($v_2$), including all (R) or (S) configurations of the foregoing, where $v_1$ and $v_2$ are each independently H, a $C_1$ to $C_{17}$ linear or branched alkyl chain, m is 0 to 17 and n is 0 to 2; or any omega amino aliphatic, terminal aryl or aralkyl, including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or any single natural or unnatural α-amino acid, β-amino acid or α,α-disubstituted amino acid, including all (R) or (S) configurations of the foregoing, optionally in combination with any of the foregoing non-amino acid capping groups. In the foregoing, it is to be understood that, for example, —C(=O)—NH—$(CH_2)_m$—NH—C(=O)—CH(N($v_1$)($v_2$))(($CH_2)_m$—N($v_1$)($v_2$)) is:

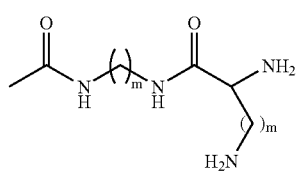

"N-Terminus Capping Group"

The term "N-terminus capping group" includes any terminal group attached through the terminal amine of the N-terminus of a compound. The terminal amine may form a part of a residue, or may form a part of an amino acid surrogate. In a preferred aspect, the N-terminus capping group forms a part of an amino acid surrogate which is at the N-terminus position of the compound. The N-terminus capping group includes, but is not limited to, any omega amino aliphatic, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7-amino heptanoyl, 6-Ahx, Amc or 8-Aoc, or alternatively an N-terminus capping group is —$(CH_2)_m$—$NH(v_3)$, —$(CH_2)_m$—$CH_3$, —$C(=O)$—$(CH_2)_m$—$CH_3$, —$C(=O)$—$(CH_2)_m$—$NH(v_3)$, —$C(=O)$—$(CH_2)_m$—$C(=O)$—OH, —$C(=O)$—$(CH_2)_m$—$C(=O)$-$(v_4)$, —$(CH_2)_m$—$C(=O)$—OH, —$(CH_2)_m$—$C(=O)$-$(v_4)$, $C(=O)$—$(CH_2)_m$—$C(v_3)$, —$(CH_2)_m$—$O(v_3)$, $C(=O)$—$(CH_2)_m$—$S(v_3)$, or —$(CH_2)_m$—$S(v_3)$, where $v_3$ is H or a $C_1$ to $C_{17}$ linear or branched alkyl chain, and $v_4$ is a $C_1$ to $C_{17}$ linear or branched alkyl chain and m is 0 to 17.

The chemical naming protocol and structure diagrams used herein employ and rely on the chemical naming features as utilized by the ChemDraw program (available from Cambridgesoft Corp., Cambridge, Mass.). In particular, certain compound names were derived from the structures using the Autonom program as utilized by Chemdraw Ultra or ISIS base (MDL Corp.). In general, structure diagrams do not depict hydrogen atoms associated with carbon atoms other than in terminal groups and other special circumstances.

Certain compounds are depicted herein with the surrogates identified by structure diagrams and the amino acid residues identified by a three letter abbreviation. Unless otherwise specified, it is understood that the bond between the surrogate and residue, or between the residue and surrogate, or between a surrogate and residues on both the N-terminus and C-terminus side thereof, is a conventional peptide bond, —$C(=O)$—NH— or, in the case where the peptide bond is to the ring nitrogen on the N-terminus of the surrogate, —$C(=O)$—N—. In general, in the depiction of such bonds the atoms of the amino acid surrogate are depicted (e.g., —$C(=O)$— or —N), but atoms of the amino acid residue are not depicted.

2. Isomeric Purity and Isolation

The surrogates of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass the racemic form of compounds of the invention as well as all enantiomers and stereoisomers, that is, both the stereomerically pure form (e.g., geometrically pure, enantiomerically pure, or diastereomerically pure) and enantiomeric and stereoisomeric mixtures.

A surrogate of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically enriched form when the compound has an enantiomeric excess of greater than about 80% ee, preferably greater than about 85% ee. As used herein, a racemic mixture means about 50% of one enantiomer and about 50% of its corresponding enantiomer relative to all chiral centers in the molecule. Thus, the invention encompasses all enantiomerically pure, enantiomerically enriched, and racemic mixtures of compounds of the invention.

Thus in one aspect, the surrogate has the general structure:

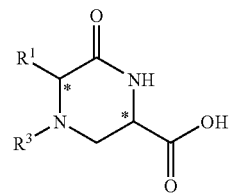

where the asterisk indicates any possible stereochemical conformation. This thus includes the following enantiomeric forms:

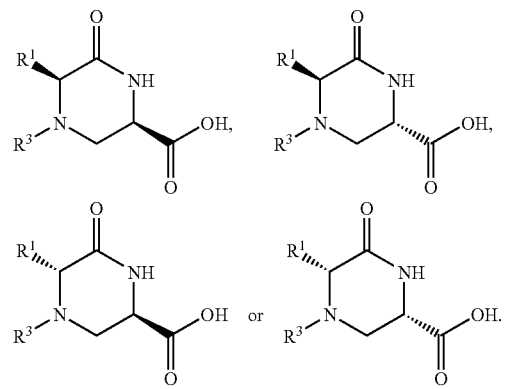

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

3. Compounds of the Invention

The invention provides ring-constrained amino acid surrogates of the formula I and linear or cyclic compounds comprising ring-constrained amino acid surrogates of formula I:

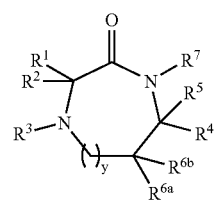

I or an enantiomer, stereoisomer or diastereoisomer thereof, or a synthetically acceptable salt thereof, wherein:

$R^1$ is H, alkyl, aryl, alkylaryl, alkyl-$N(R^8)_2$, alkyl-$OR^8$, alkyl-$C(=O)OR^8$, $C(=O)OR^8$, alkyl-$NH_2$, alkyl-S—$R^8$ alkyl-$C(=O)N(R^8)_2$, or a group of a formula:

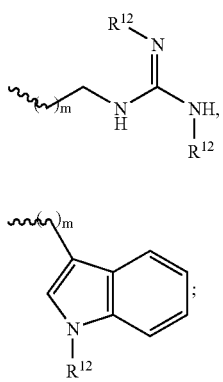

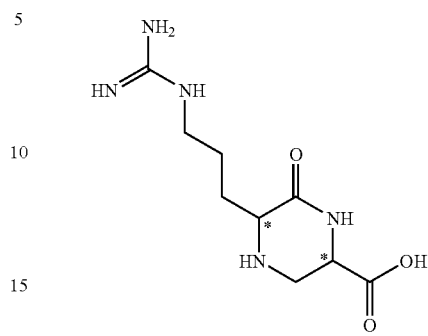

where the $R^1$ or $R^2$ group is an amino acid side chain moiety of Arg, the compound may be generically shown as:

$R^2$ is H or alkyl, provided that $R^1$ and $R^2$ are not both H;
$R^3$ is H or a first nitrogen protecting group;
$R^4$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_q$Oallyl, $(CH_2)_mC(=O)N(R^8)_2$, or $(CH_2)_mC(=O)N(R^8)(CH_2)_pN(R^8)_2$;
$R^5$ is H or alkyl;
$R^{6a}$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_q$Oallyl, $(CH_2)_mC(=O)N(R^8)_2$, or $(CH_2)_mC(=O)N(R^8)(CH_2)_pN(R^8)_2$;
$R^{6b}$ is H or alkyl;
provided that both of $R^4$ and $R^{6a}$ are not $(CH_2)_mC(=O)OH$, $(CH_2)_mC(=O)N(H)R^{11}$, $(CH_2)_mC(=O)OR^{11}$, $(CH_2)_qH$, $(CH_2)_qOBn$, $(CH_2)_q$Oallyl, $(CH_2)_mC(=O)N(R^8)_2$, or $(CH_2)_mC(=O)N(R^8)(CH_2)_pN(R^8)_2$;
$R^7$ is H, $C(=O)$alkyl, $C(=O)(CH_2)_m(NR^8)_2$, alkyl, aralkyl, or aryl;
each occurrence of $R^8$ is independently H, aryl, or alkyl;
$R^{11}$ is a peptide solid support;
$R^{12}$ is H or a second nitrogen protecting group;
each occurrence of m is an independent integer having a value between 0 and 6;
each occurrence of q is an independent integer having a value between 1 and 6;
p is an integer having a value between 1 and 10; and
y is 0 or 1.

Ring-constrained amino acid surrogates of the formula I may be employed for substitution of one or more amino acid residues of polypeptide compounds made of a plurality of amino acid residues.

The ring-constrained amino acid surrogates of formula I is preferably such that it may be made with a conventional amino protected N-terminus, using a protecting group such as Fmoc, and a reactive carboxyl C-terminus, and may thus be employed in conventional peptide synthesis methodologies. It is understood that if the amino acid surrogate of formula I is to be coupled at the C-terminus position of the compound, that other than a carboxyl terminus may be employed on such surrogate.

Thus in a preferred embodiment the invention provides ring-constrained amino acid surrogates for incorporation, by way of peptide synthesis methodologies, modified as appropriate, into polypeptide compounds, which compounds comprise a plurality of amino acid residues.

Except where both $R^1$ and $R^2$ are H, it is to be appreciated that each surrogate of the invention can be in one of four different enantiomeric forms. Thus, by way of example, where each asterisk represents a chiral center which may be in any stereochemical configuration. Thus, it is to be understood that each of the following is possible, contemplated and intended:

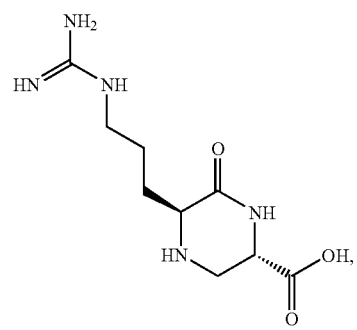

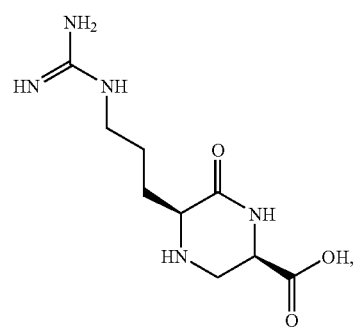

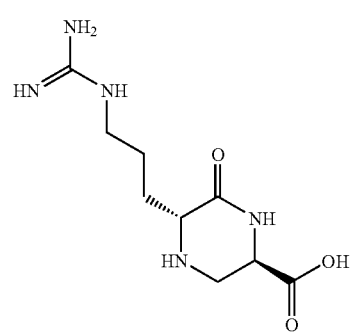

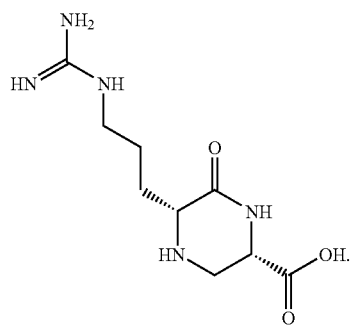

Similarly, with respect to each surrogate, for use in the synthesis of compounds using conventional peptide synthetic methodologies, it is understood that if a surrogate is other than at the N-terminal position that the $R^3$ position will include a nitrogen protecting group rather than H, and thus will be of the following general structure:

where PRG is a nitrogen protecting group, such as, by way of example and not limitation, a group of the formula:

where $R^9$ is tert-butyl, allyl, or a group of a formula:

Thus it may be seen, in the example where the $R^1$ or $R^2$ group is an amino acid side chain moiety of Arg and $R^3$ is the nitrogen protecting group Fmoc, that each of the following is possible, contemplated and intended:

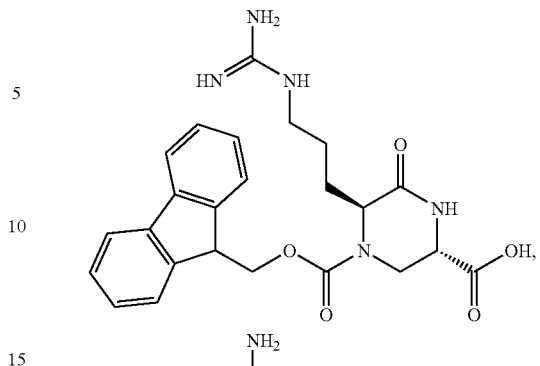

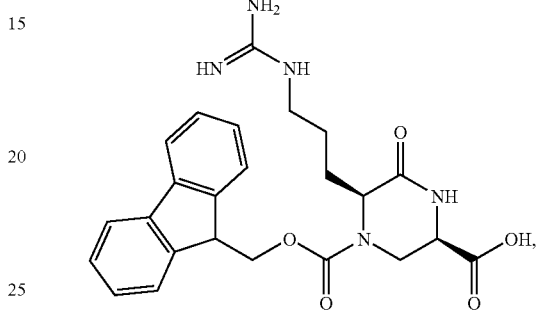

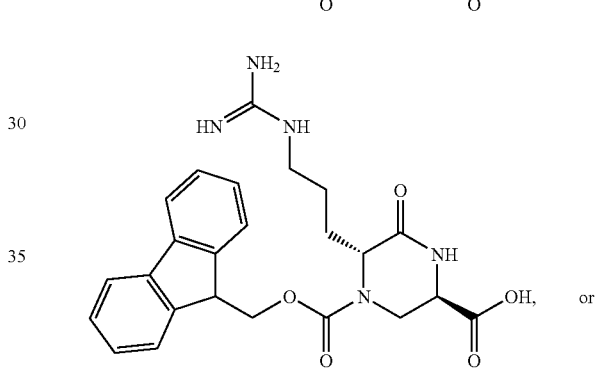

In the specific example above, it is also possible and contemplated that a nitrogen protecting group, such as for example Pbf, would be employed in the guanidino group. It may also be seen that analogous surrogates are possible and contemplated employing another group as the nitrogen protecting group or another amino acid side chain moiety or derivative of an amino acid side chain moiety as the $R^1$ or $R^2$ group, or alternatively, where at least one thereof is alkyl, aryl, alkylaryl, alkyl-N($R^8$)$_2$, alkyl-OR$^8$, alkyl-C(=O)OR$^8$, C(=O)OR$^8$, alkyl-NH$_2$, alkyl-S—R$^8$, alkyl-C(=O)N($R^8$)$_2$, or a group of a formula:

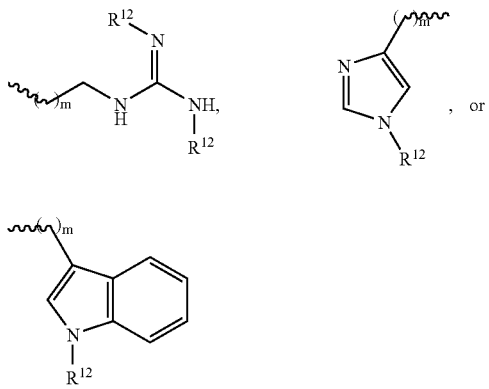

where $R^8$ is H, aryl, or alkyl and $R^{12}$ is H or a second nitrogen protecting group.

If a surrogate is employed in the synthesis of compounds using conventional peptide synthetic methodologies and is at the C-terminal position, then the surrogate may be a compound that is bonded to a peptide solid support, such as a resin. In this instance the surrogate may be of the following general structure:

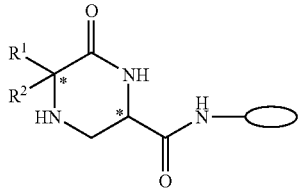

where the oval depicts resin and a linker or another peptide solid support. Here too the $R^1$ or $R^2$ group may be any amino acid side chain moiety or derivative of an amino acid side chain moiety, or alternatively, at least one thereof may be alkyl, aryl, alkylaryl, alkyl-$N(R^8)_2$, alkyl-$OR^8$, alkyl-$C(=O)OR^8$, $C(=O)OR^8$, alkyl-$NH_2$, alkyl-S—$R^8$, alkyl-$C(=O)N(R^8)_2$, or a group of a formula:

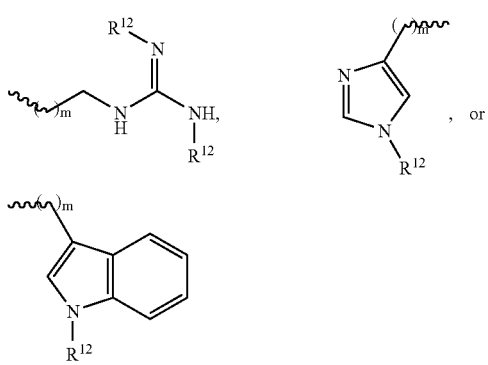

where $R^8$ is H, aryl, or alkyl and $R^{12}$ is H or a second nitrogen protecting group.

In one aspect, the invention thus provides surrogates of the following general structure:

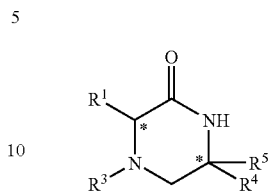

where $R^1$ is one of the following:

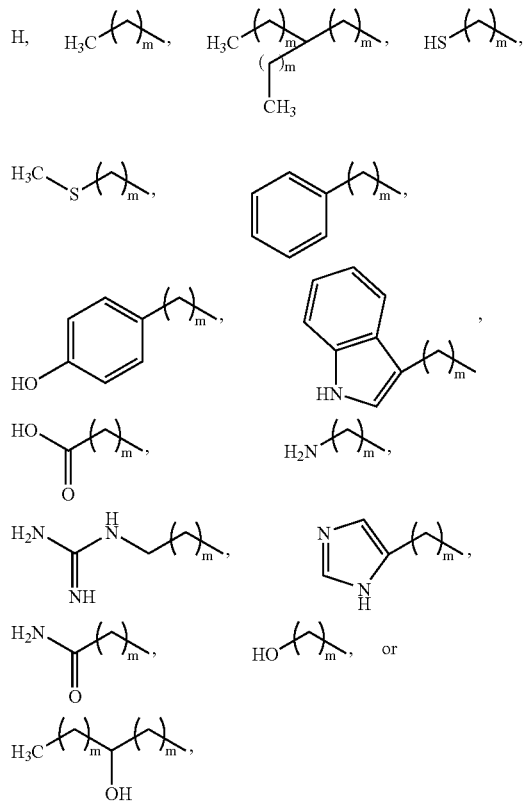

where $R^3$ is H or a first nitrogen protecting group; $R^4$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$; $R^5$ is H or alkyl; $R^8$ is H, aryl, or alkyl; $R^{11}$ is a peptide solid support; each occurrence of m is an independent integer having a value between 0 and 6; each occurrence of q is an independent integer having a value between 1 and 6; p is an integer having a value between 1 and 10; and any aryl group may be substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Thus in one aspect there are provided surrogates with an $R^1$ group which is an amino acid side chain moiety of one of the following nineteen naturally-coded amino acid residues (omitting Pro), including the following:

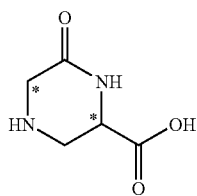

6-Oxo-piperazine-2-carboxylic acid

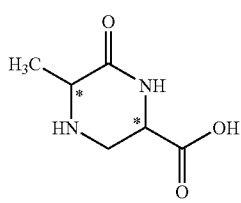

5-Methyl-6-oxo-piperazine-2-carboxylic acid

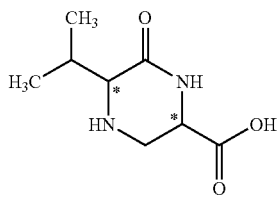

5-Isopropyl-6-oxo-piperazine-2-carboxylic acid

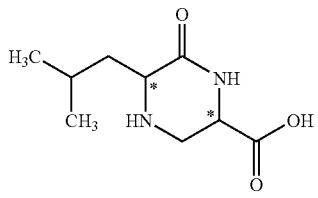

5-Isobutyl-6-oxo-piperazine-2-carboxylic acid

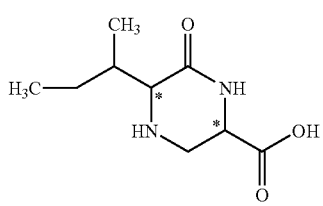

5-sec-Butyl-6-oxo-piperazine-2-carboxylic acid

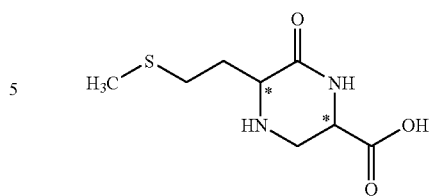

5-(2-Methylsulfanyl-ethyl)-6-oxo-piperazine-2-carboxylic acid

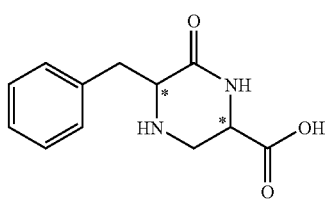

5-Benzyl-6-oxo-piperazine-2-carboxylic acid

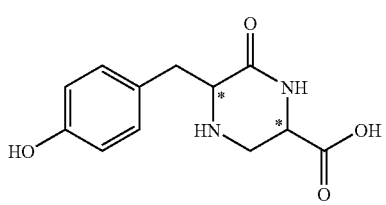

5-(4-Hydroxy-benzyl)-6-oxo-piperazine-2-carboxylic acid

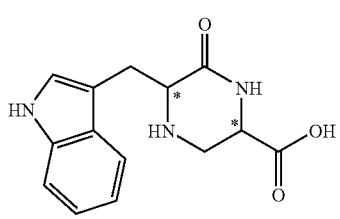

5-(1H-Indol-3-ylmethyl)-6-oxo-piperazine-2-carboxylic acid

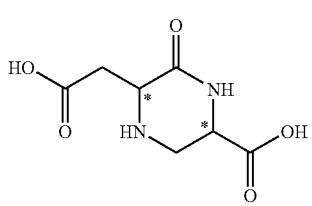

5-Carboxymethyl-6-oxo-piperazine-2-carboxylic acid

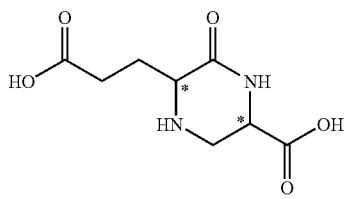

5-(2-Carboxy-ethyl)-6-oxo-piperazine-2-carboxylic acid

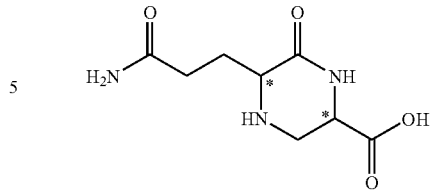

5-(2-Carbamoyl-ethyl)-6-oxo-piperazine-2-carboxylic acid

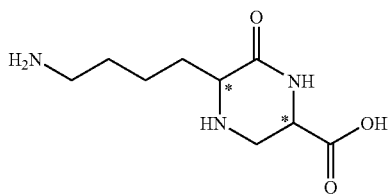

5-(4-Amino-butyl)-6-oxo-piperazine-2-carboxylic acid

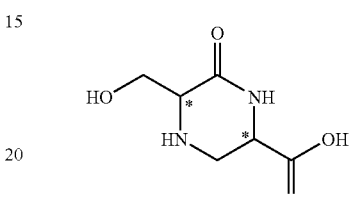

5-Hydroxymethyl-6-oxo-piperazine-2-carboxylic acid

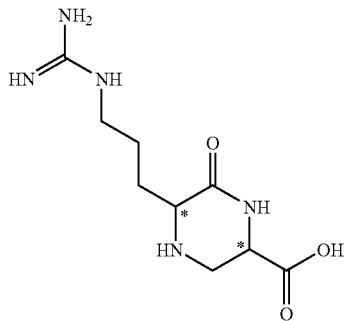

5-(3-Guanidino-propyl)-6-oxo-piperazine-2-carboxylic acid

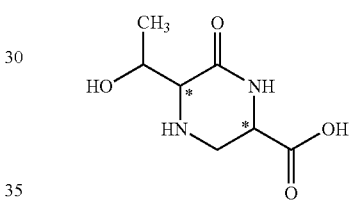

5-(1-Hydroxy-ethyl)-6-oxo-piperazine-2-carboxylic acid

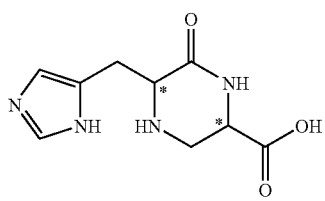

5-(3H-Imidazol-4-ylmethyl)-6-oxo-piperazine-2-carboxylic acid

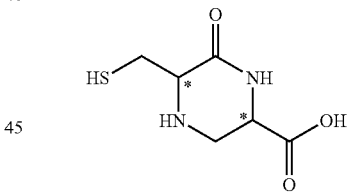

5-Mercaptomethyl-6-oxo-piperazine-2-carboxylic acid

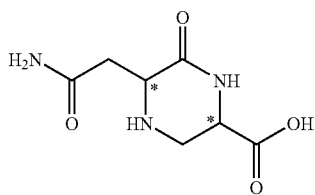

5-Carbamoylmethyl-6-oxo-piperazine-2-carboxylic acid

In each of the foregoing, rather than H in the $R^3$ position there may be any nitrogen protecting group; rather than —C(=O)OH the $R^4$ position may be alkyl, $(CH_2)_qC(=O)OH$, $(CH_2)_mC(=O)N(H)R^{11}$, $(CH_2)_mC(=O)OR^{11}$, $(CH_2)_q$ OH, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$ where $R^8$ is H, aryl, or alkyl, $R^{11}$ is a peptide solid support, m is an independent integer having a value between 0 and 6, q is an independent integer having a value between 1 and 6 and p is an integer having a value between 1 and 10; rather than H the $R^5$ position may be alkyl; and rather than H the $R^7$ position may be C(=O)alkyl or $C(=O)(CH_2)_m(NR^8)_2$—Similarly, rather than one of the foregoing amino acid side chain moieties, $R^1$ may be alkyl, aryl, alkylaryl, alkyl-$N(R^8)_2$, alkyl-$OR^8$, alkyl-C(=O)$OR^8$, C(=O)$OR^8$, alkyl-$NH_2$, alkyl-S—$R^8$ alkyl-C(=O)$N(R^8)_2$, or a group of a formula:

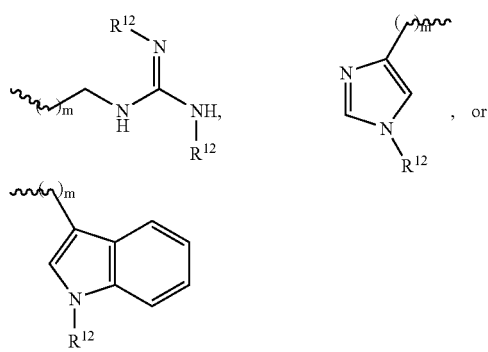

where $R^8$ is H, aryl, or alkyl and $R^{12}$ is H or a second nitrogen protecting group.

4. Use of Compounds of the Invention

In accordance with one aspect of the present invention there is provided a method of making a compound including a surrogate, which compound is based on a known parent polypeptide that binds to a target of interest. The parent polypeptide may be a peptide, a polypeptide or a protein.

In another aspect of the present invention, there is provided a method for identifying a secondary structure of a parent polypeptide which secondary structure is involved in or responsible for binding to a target of interest. Such method includes (a) providing a known parent polypeptide that binds to a target of interest with a known primary structure, such primary structure consisting of n amino acid residues; (b) constructing a plurality of compounds wherein a surrogate is substituted for an amino acid residue in the parent polypeptide, the substituted surrogate preferably having an $R^1$ or $R^2$ group that is the same as the amino acid side chain moiety of the amino acid residue for which it is substituted, or which is a derivative of the amino acid side chain moiety of the amino acid residue for which it is substituted; (c) screening the plurality of compounds including a surrogate; and (d) selecting the compound exhibiting binding to the target of interest, whereby such compound comprises the secondary structure binding to the target of interest.

In a related aspect of the present invention, there is provided a method for identifying a secondary structure of a parent polypeptide which secondary structure is involved in or responsible for binding to a target of interest, the method including the step of constructing a plurality of compounds wherein a surrogate is substituted for an amino acid residue in the parent polypeptide, the substituted surrogate preferably having an $R^1$ and $R^2$ group limited to H in both positions or methyl in one position and H in the remaining position. In this manner the effect of the amino acid side chain moiety on efficacy or any other ascertainable parameter may readily be determined.

In one embodiment, the method of the invention provides for the systematic analysis of a parent polypeptide to determine at least one active sequence or domain in the parent polypeptide that is involved in the interaction, such as binding, of the parent polypeptide with a target substance. As used herein, "parent polypeptide" refers to any sequence of amino acid residues that exhibits interaction, such as binding, to a target substance, and which may thus constitute a peptide, a polypeptide or a protein. The parent polypeptide is generally a polypeptide as defined herein, with from about 3 to about 100 amino acid residues, but the term parent polypeptide can also include larger constructs, generally considered in the art to be large polypeptides or proteins. To employ the method of the invention, the primary structure, which is to say the sequence, of at least part, and preferably of all, of the parent polypeptide must be available. However, it is not necessary to have any information concerning the secondary or tertiary structure of the parent polypeptide in order to practice the method of the invention.

The parent polypeptide may be any sequence that exhibits binding to a receptor found on, for example, cells, tissues, organs or other biological materials. Examples of parent polypeptides include, without limitation, biologically active peptides, hormones, neurotransmitters, enzymes, antibodies and the like. Such parent polypeptides may transmit signals, directly or indirectly, as a result of binding to a receptor, and thus a parent polypeptide may be an agonist, an antagonist, or a mixed agonist-antagonist. Examples of suitable parent polypeptides of the invention include melanocortin-receptor specific peptides, urokinase-type tissue plasminogen activator protein, amyloid beta-protein related peptides, prion disease related peptides, vasopressin peptides, oxytocin peptides, natriuretic peptides, angiotensin peptides, calcitonin, calcitonin gene related peptide, opioid peptides, human growth hormone, human prolactin receptor ligands, various interferons, such as alpha-interferon, epidermal growth factor, tumor necrosis factor, and various hypotensive peptides, fibrinolytic peptides, chemotactic peptides, growth promoter peptides, cell adhesion peptides and polypeptides, mitogens, immunomodulators and the like.

In general, in order to employ the invention at least one assay or test to determine a parameter of a construct of the invention with respect to a receptor of interest. In one aspect, binding of the constructs of the invention to a receptor of interest is employed, and preferably with parallel determination of binding of the parent polypeptide to the receptor of interest. However, other parameters than binding may be employed, including various functional assay systems, efficacy assay systems, and the like. Such parameters may be determined with respect to any relevant unit of measure, including expression of one or more compounds in a functional assay system, Ki values, $EC_{50}$ values, and the like. Thus in one preferred embodiment of the invention, a competitive inhibition or similar assay is employed, whereby the binding or functional activity of a construct of the invention can be directly compared to the parent polypeptide, and relative binding or functional activity thus directly determined. In other embodiments other assays or tests may be employed. These assays may, but need not, be functional assays. Examples of assays include any of a variety of competitive inhibition assays, direct binding assays, functional assays, and the like. It is also possible and contemplated to employ assays that determine, for example, whether a construct of the invention is an agonist, antagonist or mixed agonist-antagonist, and further where binding and function can separately be determined, to independently determine both receptor affinity and specificity as well as functional activity. Examples of such assays and tests are well known and well documented in the art, and in general one or more such assays or tests are known for any parent polypeptide.

In one method of the invention, the parent polypeptide is employed as the template for generation of one or more, and preferably of a series, of compounds each including at least one surrogate substituted for at least one amino acid residue of the parent polypeptide. In one aspect, the compounds with at least one surrogate may omit one or more amino acid residues found in the parent polypeptide. In another aspect, the compounds with at least one surrogate contain the same amino acid residues, or homologs thereof, as found in the parent polypeptide, with one or more amino acid residues substituted with a surrogate. In one aspect the substituted surrogate preferably has an $R^1$ or $R^2$ group that is the same as the amino acid side chain moiety of the amino acid residue for which it is substituted, or which is a derivative of the amino acid side chain moiety of the amino acid residue for which it is substituted. In another aspect, the substituted surrogate preferably has an $R^1$ and $R^2$ group limited to H in both positions or methyl in one position and H in the remaining position.

Assume, for example, a parent polypeptide of six amino acid residues that binds to a specified and known receptor. The parent polypeptide may be described as:

$X^1$—$X^2$—$X^3$—$X^4$—$X^5$—$X^6$

A surrogate of this invention referred to as "S" is employed to synthesize a compound described as:

$X^1$—$X^2$—$X^3$—S—$X^5$—$X^6$

In one aspect of the compound $X^1$—$X^2$—$X^3$—S—$X^5$—$X^6$, where the amino acid residue $X^4$ is replaced by S, S has an $R^1$ or $R^2$ group that is the same as the amino acid side chain moiety of $X^4$, or which is a derivative of the amino acid side chain moiety of $X^4$. In another aspect, where $X^4$ is other than Gly or Ala, S has an $R^1$ and $R^2$ group H in both positions or methyl in one position and H in the remaining position. Binding of the compound $X^1$—$X^2$—$X^3$—S—$X^5$—$X^6$, or some other measure of efficacy, is determined and compared to the parent polypeptide $X^1$—$X^2$—$X^3$—$X^4$—$X^5$—$X^6$.

It is possible and contemplated that a systematic evaluation may be performed. Assume a peptide of fifteen amino acid residues binds to a specified known receptor. The peptide may be described as:

$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH

In this parent polypeptide, X may be any residue, which residue may repeat multiple times in any order or sequence. Thus the residue in position $X^1$ may be different from or the same as the residue in position $X^2$, which may be different from or the same as the residues in position $X^1$ or $X^3$, and so on. A series of compounds are made wherein a surrogate "S" is substituted for an amino acid residue in a sequential or step-wise fashion. Thus, for example the following may result:

S—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH
$NH_2$—$X^1$—S—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—COOH
$NH_2$—$X^1$—$X^2$—S—$X^4$—$X^5$—$X^6$—$X^7$—$X^8$—$X^9$—$X^{10}$—$X^{11}$—$X^{12}$—$X^{13}$—$X^{14}$—$X^{15}$—COOH
$NH_2$—$X^1$—$X^2$—$X^3$—S—$X^5$—$X^6$—$X^7$—$X^8$—$X^9$—$X^{10}$—$X^{11}$—$X^{12}$—$X^{13}$—$X^{14}$—$X^{15}$—COOH
$NH_2$—$X^1$—$X^2$—$X^3$—$X^4$S—$X^6$—$X^7$—$X^8$—$X^9$—$X^{10}$—$X^{11}$—$X^{12}$—$X^{13}$—$X^{14}$—$X^{15}$—COOH
$NH_2$—$X^1$—$X^2$—$X^3$—$X^4$—$X^5$—S—$X^7$—$X^8$—$X^9$—$X^{10}$—$X^{11}$—$X^{12}$—$X^{13}$—$X^{14}$—$X^{15}$—COOH
$NH_2$—$X^1$—$X^2$—$X^3$—$X^4$—$X^5$—$X^6$—S—$X^8$—$X^9$—$X^{10}$—$X^{11}$—$X^{12}$—$X^{13}$—$X^{14}$—$X^{15}$—COOH
$NH_2$—$X^1$—$X^2$—$X^3$—$X^4$—$X^5$—$X^6$—$X^7$—S—$X^9$—$X^{10}$—$X^{11}$—$X^{12}$—$X^{13}$—$X^{14}$—$X^{15}$—COOH
$NH_2$—$X^1$—$X^2$—$X^3$—$X^4$—$X^5$—$X^6$—$X^7$—$X^8$—S—$X^{10}$—$X^{11}$—$X^{12}$—$X^{13}$—$X^{14}$—$X^{15}$—COOH
$NH_2$—$X^1$—$X^2$—$X^3$—$X^4$—$X^5$—$X^6$—$X^7$—$X^8$—$X^9$—S—$X^{11}$—$X^{12}$—$X^{13}$—$X^{14}$—$X^{15}$—COOH
$NH_2$—$X^1$—$X^2$—$X^3$—$X^4$—$X^5$—$X^6$—$X^7$—$X^8$—$X^9$—$X^{10}$—S—$X^{12}$—$X^{13}$—$X^{14}$—$X^{15}$—COOH
$NH_2$—$X^1$—$X^2$—$X^3$—$X^4$—$X^5$—$X^6$—$X^7$—$X^8$—$X^9$—$X^{10}$—$X^{11}$—S—$X^{13}$—$X^{14}$—$X^{15}$—COOH
$NH_2$—$X^1$—$X^2$—$X^3$—$X^4$—$X^5$—$X^6$—$X^7$—$X^8$—$X^9$—$X^{10}$—$X^{11}$—$X^{12}$—S—$X^{14}$—$X^{15}$—COOH
$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—S—$X^{15}$—COOH
$NH_2$—$X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—S

In the foregoing, the surrogate S has, for each compound, an $R^1$ or $R^2$ group that is the same as the amino acid side chain moiety of the amino acid residue for which it is substituted, or which is a derivative of the amino acid side chain moiety of the amino acid residue for which it is substituted. Similarly, for each position all enantiomeric forms may be employed and evaluated. Additionally, for each position a "knock-out" approach may be evaluated, in which where X is other than Gly or Ala, S has an $R^1$ and $R^2$ group H in both positions or methyl in one position and H in the remaining position.

It is also possible and contemplated to substitute one or more amino acid residues in a parent polypeptide with another amino acid residue, while also substituting one or more amino acid residues in a parent polypeptide with a surrogate of the invention. In one aspect a D-isomer is substituted for an L-isomer in a naturally occurring parent polypeptide. The corresponding amino acid sequence comprising at least one surrogate of formula I may be identical to a known parent polypeptide, or may be homologous thereto, such as a corresponding amino acid sequence that is at least 60% homologous, or more preferably is at least about 80% homologous. For these purposes, homology is determined by reference to identity of the known amino acid sequence to the compound but for the substitution by or addition of one or more surrogates of formula I.

In another aspect, the invention provides ring-constrained amino acid surrogates of formula II useful to synthesize a compound that is modeled on a known peptide which binds to a receptor for a natriuretic peptide, but which includes one or more amino acid surrogates, such surrogates being either substituted for one or more amino acid residues contained in the known peptide, or in addition to the sequence comprising the known peptide. The known peptide may be any natriuretic peptide known in the art, including but not limited to those disclosed in any publication, patent, application or reference cited herein, including but not limited to the natriuretic peptides disclosed in U.S. Pat. Nos. 4,496,544; 4,609,725; 4,656,158; 4,673,732; 4,716,147; 4,757,048; 4,764,504; 4,804,650; 4,816,443; 4,824,937; 4,861,755; 4,904,763; 4,935,492; 4,952,561; 5,047,397; 5,057,495; 5,057,603; 5,091,366; 5,095,004; 5,106,834; 5,114,923; 5,159,061; 5,204,328; 5,212,286; 5,352,587; 5,376,635; 5,418,219; 5,665,704; 5,846,932; 5,583,108; 5,965,533; 6,028,055; 6,083,982; 6,124,430; 6,150,402; 6,407,211; 6,525,022; 6,586,396 or 6,818,619; in U.S. Patent Application Publications 2004/0002458; 2004/0063630; 2004/0077537; 2005/0113286; 2005/0176641; or 2006/0030004; or in various non-U.S. patents and patent applications, including WO 85/04870; WO 85/04872; WO 88/03537; WO 88/06596; WO 89/10935; WO 89/05654; WO 90/01940; WO 90/14362; WO 92/06998; WO 95/13296; WO 99/08510; WO 99/12576; WO 01/016295; WO 2004/047871; WO 2005/072055; EPO 0 291 999; EPO 0 323 740; EPO 0 341 603; EPO 0 350 318; EPO 0 356 124; EPO 0 385 476; EPO 0 497 368; or EPO 0 542 863. In one aspect, the known peptide is a peptide or homolog thereof disclosed in U.S. Pat. No. 4,656,158, 4,824,937, 4,935,492, 5,159,061, 5,204,328, 5,376,635, 5,665,704, 5,846,932, 6,028,055, 6,407,211, 6,525,022, 6,586,396, or 6,818,619, U.S. Patent Application Publications 2004/0002458, 2004/0063630, or 2005/0176641, or International Patent Application Publications WO 2004/047871 or WO 2005/072055. The teachings of each of the foregoing patents and patent applications are incorporated by reference as if set forth in full. In one aspect, the amino acid sequence which binds to a natriuretic peptide receptor is, prior to substitution, H-Met-cyclo(Cys-His-Phe-Gly-Gly-Arg-Met-Asp-Arg-Ile-Ser-Cys)-Tyr-Arg-NH$_2$ (SEQ ID NO:1). In another aspect the invention provides a ring-constrained amino acid surrogates of formula I useful to synthesize a compound that binds to a receptor for a natriuretic peptide, including a receptor for ANP or BNP.

Compounds made using one or more surrogates of formula I can be used for both medical applications and animal husbandry or veterinary applications. Typically, the compound, or a pharmaceutical composition including the compound, is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The compounds disclosed herein, or made by methods disclosed herein, may be used for the treatment of any condition, syndrome or disease, and in particular for any condition, syndrome or disease for which a parent polypeptide has some efficacy. The compounds disclosed herein, or made by methods disclosed herein, can have one or more advantages relative to the parent polypeptide, including but not limited to advantages such as increased resistance to enzymatic degradation, increased circulation half life, increased bioavailability, increased efficacy, prolonged duration of effect and combinations of the foregoing. Such advantages are due, in whole or part, to use of the surrogates of formula I of the invention.

In one aspect, the compounds disclosed herein are used in the treatment of early stage, such as class 1, congestive heart failure. In another aspect, the compounds disclosed herein are used in the treatment of chronic or decompensated congestive heart failure. In another aspect, the compounds disclosed herein are used in the treatment of acute congestive heart failure, including acutely decompensated congestive heart failure of patients with dyspnea at rest or with minimal activity.

Salt Form of Compounds. The compounds of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include salts of aluminum, ammonium, calcium, copper, ferric, ferrous, lithium, magnesium, manganic, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the compounds of this invention are prepared in a suitable solvent from the compound and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the compounds of embodiments of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. Another embodiment of the present invention provides a pharmaceutical composition that includes a compound of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The compounds of the several embodiments of the present invention may be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

In general, the actual quantity of compounds administered to a patient will vary between fairly wide ranges depending on the mode of administration, the formulation used, and the response desired.

In practical use, the compounds can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, a composition including a compound of this invention may be coated by standard aqueous or nonaqueous techniques. The amount of active compound in such therapeutically useful compositions is such that an effective dosage will be obtained. In another advantageous dosage unit form, sublingual pharmaceutical compositions may be employed, such as sheets, wafers, tablets or the like. The active compound can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds may also be administered parenterally. Solutions or suspensions of these active peptides can be prepared in water suitably mixed with a surfactant such as hydroxypropylcellulose. Dispersions can also be prepared in glycerol, liquid polyethylene glycols and mixtures thereof in oils. These preparations may optionally contain a preservative to prevent the growth of microorganisms. Lyophilized single unit formulations may also be employed, such as are reconstituted with saline prior to administration, and thus do not require a preservative.

The pharmaceutical forms suitable for injectable use include sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Compounds as disclosed herein may be therapeutically applied by means of nasal administration. By "nasal administration" is meant any form of intranasal administration of any of the compounds of this invention. The compounds may be in an aqueous solution, such as a solution including saline, citrate or other common excipients or preservatives. The compounds may also be in a dry or powder formulation.

In an alternative embodiment, compounds may be administered directly into the lung. Intrapulmonary administration may be performed by means of a metered dose inhaler, a device allowing self-administration of a metered bolus of a compound of this invention when actuated by a patient during inspiration. Both dry powder inhalation and nebulized aerosols may be employed.

According to another embodiment of the present invention, compounds of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, certain compounds of the present invention may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the compound may be in a dried and particulate form. In a preferred embodiment, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the compounds may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The compounds of this invention may be therapeutically administered by means of an injection, typically a deep intramuscular injection, such as in the gluteal or deltoid muscle, of a time release injectable formulation. In one embodiment, a compound of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment a compound of this invention is formulated with a poly(ortho ester), which may be an auto-catalyzed poly (ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a compound of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of compound, the biodegradation rate of the polymer, and other factors known to those of skill in the art.

Routes of Administration. If it is administered by injection, the injection may be intravenous, subcutaneous, intramuscular, intraperitoneal or other means known in the art. The compounds of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the compounds of this invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In one aspect, a compound of this invention is administered by means of a time release injectable formulation, such as a compound of this invention in a formulation with a PEG, poly(ortho ester) or PLGA polymer. In another aspect, a compound of this invention is administered by means of an automated delivery device providing subcutaneous delivery, either continuous or intermittent. Any of the foregoing methods and formulations are particularly applicable for treatment of chronic conditions or syndromes, including chronic congestive heart failure and particularly chronic decompensated congestive heart failure.

In one aspect, any compound of this invention may be administered by subcutaneous administration, including all the methods disclosed in U.S. Pat. No. 6,586,396. In another aspect, a patient, particularly a patient who is relatively compensated or is a patient with congestive heart failure in an outpatient setting, may be administered a compound of this invention by methods and in doses as disclosed in U.S. Patent Application Publication 2004/0077537 and International Patent Application Publication WO 2003/079979. In another aspect, a patient may be administered a compound of this invention by means of the methods as disclosed in U.S. Patent Application Publication 2005/0113286. In yet another aspect, a patient who has undergone myocardial injury may be treated for cardiac remodeling by means of the methods as disclosed in U.S. Patent Application Publication 2006/0019890.

A compound of this invention may also be administered by transdermal administration, including by means of the delivery system, including the apparatus, and the methods as disclosed in U.S. Patent Application Publication 2006/0034903. Similarly, the hydrogel formulations and solid state formulations disclosed therein may be adapted for use with the compounds of this invention.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce a desired effect. In one aspect where a natriuretic peptide is employed as the parent polypeptide in making a compound including one or surrogates of formula I, a therapeutically effective amount is an amount that results in desired natriuresis, diuresis and/or vasodilation.

In general, the compounds of this invention are highly active. For example, the compound can be administered at about 0.01, 0.05, 0.1, 0.5, 1, 5, 10, 50, or 100 µg/kg body weight, depending on the specific compound selected, the desired therapeutic response, the route of administration, the formulation and other factors known to those of skill in the art.

5. Synthetic Methods for Surrogates of Formula I

The surrogates of formula I of the invention can be obtained via standard, synthetic methodology. Some convenient methods are illustrated in the Schemes below. Starting materials useful for preparing the compounds of the invention and intermediates therefor, are commercially available or can be prepared from commercially available materials using known synthetic methods and reagents.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly, the precise structure of the protecting group is not critical.

Numerous reactions for the formation and removal of such protecting groups are described in a number of standard works including, for example, *Protective Groups in Organic Chemistry*, Plenum Press, London and New York, 1973; Greene, Th. W. *Protective Groups in Organic Synthesis*, Wiley, New York, 1981; *The Peptides*, Vol. I, Schroder and Lubke, Academic Press, London and New York, 1965; and *Methoden der organischen Chemie*, Houben-Weyl, 4th Edition, Vol. 15/I, Georg Thieme Verlag, Stuttgart 1974, the disclosures of which are incorporated herein by reference.

The following examples of methods of synthesis of amino acid surrogates of formula I of the invention are intended to be exemplary, and it is to be understood that variations thereon may be undertaken by one of skill in the art, and such variations are intended to be included herein.

The following examples of methods of synthesis of amino acid surrogates of the invention are intended to be exemplary, and it is to be understood that variations thereon may be undertaken by one of skill in the art, and such variations are intended to be included herein.

Synthesis of Ketopiperazine Scaffolds Mimicking Amino Acids without Functionalized R Side Chain Methods A and B The constructs were prepared by a variety of methods as described in Methods A and B.

Method A: The dipeptides (3) were formed by the mixed anhydride method, using Boc-serine (OBn)-OH (1), and an α-amino ester (2). The dipeptides were obtained in high yields, and usually no purification was required. Reduction of both the methyl ester and the amide group was done using diborane-tetrahydrofuran, with the secondary amines protected to give the di-Boc protected amino alcohol intermediates (4). Oxidation of the alcohols with pyridinium dichromate (PDC) with concomitant cyclization gave the piperazine-2-ones (5) in one step. Benzyl ether removal by hydrogenation, followed by protecting group exchange gave the Fmoc protected piperazine-2-ones (6). Finally, the primary alcohol was oxidized to the acid by any of a number of different methods (PDC, Jones oxidation, ruthenium chloride-sodium periodate, 2,2,6,6-tetramethyl-1-piperidinyloxy, free radical (TEMPO) oxidation) to give the final products (7).

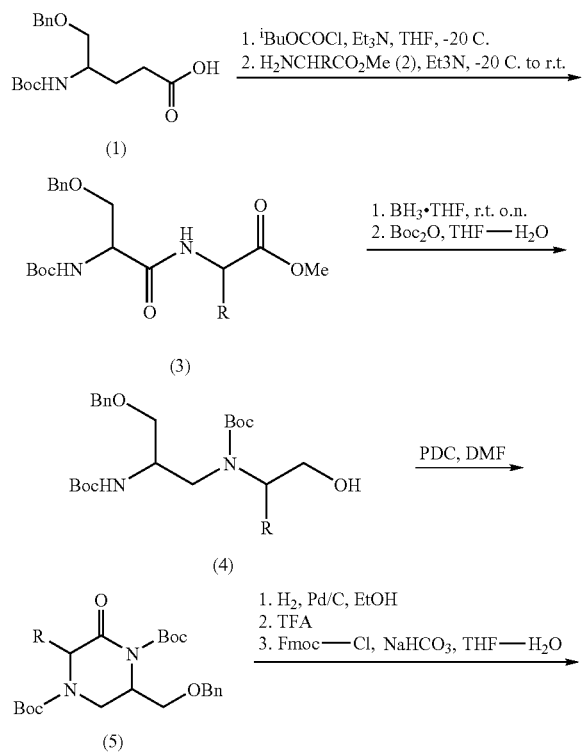

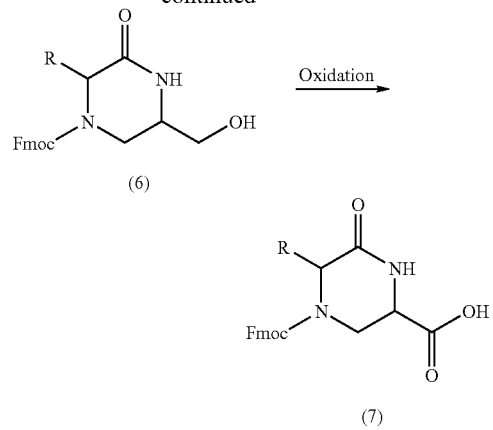

Synthesis of 2-(3-benzyloxy-2-tert-butoxycarbonylamino-propionylamino)-2-substituted acetic acid methyl ester (3): To a solution of 10 mmol of Boc serine benzyl ether (1) in 30 mL of dry tetrahydrofuran, kept at −20° C. under nitrogen, was added 22 mmol of triethylamine, followed by the slow addition of 11.4 mmol of isobutylchloroformate. A white solid precipitated out. The slurry was stirred for 15 minutes, and then 11.1 mmol of α-amino ester (2) was added in one portion. The slurry was stirred at −20° C. for 30 minutes, and then allowed to warm up to room temperature, stirred for 2 hours, and then concentrated to dryness. The mixture was then partitioned between 50 mL of ethyl acetate/30 mL of 1N hydrochloric acid solution. The layers were separated, and the organic layer washed with 1×20 mL of 1N hydrochloric acid, and 1×20 mL of saturated sodium bicarbonate solution, dried over magnesium sulfate and concentrated. Compounds (3) were usually obtained in yields above 90%, and no purification was required.

| R | Analytical Data for Compounds (3) |
|---|---|
| Ph | $^1$H NMR δ(CDCl$_3$): 1.43(s, 9H, $^t$Bu), 3.0-3.18(two sets of dd, 2H, CH$_2$—Ph), 3.50-3.57(t, 1H, CH$_2$O), 3.68(s, 3H, CH$_3$O), 3.87-3.96(br. d, 1H, CH$_2$O), 4.23-4.33(br. m, 1H, CHN), 4.45-4.57(dd, 2H, CH$_2$O), 4.80-4.88(m, 1H, CHN), 5.30-5.37(m, 1H, NH), 7.0-7.38(a series of m, 10H, Ph), yield = 96%, t$_R$ = 6.88 min, (M$^+$ + 1) = 456.99 |
| (isobutyl) | $^1$H NMR δ(CDCl$_3$): 0.81-0.96(a series of m, 6H, CH$_3$), 1.00-1.16(m, 1H, CH$_2$), 1.30-1.45(m, 1H, CH$_2$), 1.45(s, 9H, $^t$Bu), 1.80-1.96(m, 1H, CH), 3.54-3.64(dd, 1H, CH$_2$O), 3.70(s, 3H, CH$_3$O), 3.82-3.96(dd, 1H, CH$_2$O), 4.28-4.40(m, 1H, CHN), 4.51-4.61(m, and s, 3H, CH$_2$O and CHN), 5.51-5.61(br. d, 1H, NH), 7.12-7.37(br. m, 5H, Ph), yield = quant., t$_R$ = 6.93 min, (M$^+$ + 1) = 423.25 |
| H | $^1$H NMR δ(CDCl$_3$): 1.45(s, 9H, $^t$Bu), 3.73(s, 3H, CH$_3$O), 3.84-3.90(m, 2H, CH$_2$N), 4.01-4.17(m, 2H, CH$_2$O), 4.32-4.38(br. m, 1H, CHN), 4.54-4.58(d, 2H, CH$_2$O), 5.46-5.57(d, 1H, NH), 7.05-7.12(br. m, 1H, Ph), 7.24-7.40(m, 4H, Ph), yield = quant., t$_R$ = 5.51 min, (M$^+$ + 1) = 367.07 |

Synthesis of Di-Boc-2-substituted-(2-amino-3-benzyloxy-propyl-amino)-ethanol (4): To a solution of 35 mmol of (3) in 50 mL of dry tetrahydrofuran, kept at room temperature under nitrogen, was added 200 mL of 1N diborane solution in tetrahydrofuran. The solution was stirred at room temperature overnight, and then slowly poured over an ice-cold solution of 200 mL of 1N hydrochloric acid solution. The biphasic solution was then neutralized with solid sodium hydroxide. 140 mL of a saturated solution of sodium bicarbonate was added, followed by 70 mmol of di-tert-butyl-dicarbonate, and the mixture stirred for 2 days at room temperature, diluted with 200 mL of ethyl acetate and the layers separated. The organic layer was dried over magnesium sulfate, and concentrated. The products (4) were purified by silica gel column chromatography.

| R | Analytical Data Compounds (4) |
|---|---|
| ⌇⌇⌇-CH(⌇Ph)(⌇) | $^1$H NMR δ(CDCl$_3$): 1.42(s, 9H, $^t$Bu), 1.48(s, 9H, $^t$Bu), 2.48-3.02(a series of m, 2H, CH$_2$—Ph), 3.1-3.48(br. m, 1H, CH$_2$O), 3.25-3.48(br. m, 2H, CH$_2$N), 3.50-3.75(m, 2H, CH$_2$O), 3.80-3.97(m, 1H, CH$_2$O, and CHN), 4.25(br. m, 1H, CHN), 4.45(s 2H, CH$_2$O), 4.9(br. s, 1H, OH), 5.3(br. s, 1H, NH), 7.1-7.4(m, 10H, Ph), yield = 76%, $t_R$ = 8.04 min, (M$^+$ + 1) = 515.25 |
| ⌇⌇⌇-CH(iPr)(Bn) | $^1$H NMR δ(CDCl$_3$): 0.84-0.96(m, CH, CH$_2$, CH$_3$), 1.42(s, 9H, $^t$Bu), 1.45(s, 9H, $^t$Bu), 1.42-1.44(m, 1H, CH), 2.88-3.11(br. m, 2H, CH$_2$N), 3.42-3.57(m, 2H, CH$_2$O), 3.62-4.10(two m, 4H, CH$_2$O, and CHN), 4.51(s, 2H, CH$_2$O), 7.27-7.38(m, 5H, Ph), yield = 80%, $t_R$ = 8.19 min, (M$^+$ + 1) = 481.26 |
| ⌇⌇⌇-C(CH$_3$)$_3$, H | $^1$H NMR δ(CDCl$_3$): 1.35-1.43(m, 18H, $^t$Bu), 3.20-3.32(m, 1H, CH$_2$N), 3.55-3.84(a series of m, 8H, CH$_2$N, CH$_2$O), 3.90-4.05(m, 1H, CHN), 4.45(s, 2H, CH$_2$O), 4.9-5.02(m, 1H, NH), 7.2-7.35(m, 5H, Ph), yield = 56%, $t_R$ = 6.40 min, (M$^+$ + 1) = 425.21 |

Synthesis of 1,4-di-Boc-6-benzyloxymethyl-3-substituted-piperazin-2-one (5): A solution of 70 mmol of (4), and 400 mmol of pyridinium dichromate in 300 mL of dry dimethylformamide was stirred at 48° C. under nitrogen for 6 hours, cooled to room temperature, poured into 1500 mL of water, and extracted with 4×500 mL of ethyl ether. The ethereal layers were combined, dried over magnesium sulfate, and concentrated. The products (5) were purified by silica gel column chromatography.

| R | Analytical Data for Compounds (5) |
|---|---|
| ⌇⌇⌇-CH(Ph)(⌇) | $^1$H NMR δ(CDCl$_3$): 1.4(s, 9H, $^t$Bu), 1.5(s, 9H, $^t$Bu), 3.05-3.58(a series of m, CH$_2$—Ph, and CH$_2$N), 4.1-4.32(a series of m, 2H, CH$_2$N), 4.47(s, 2H, CH$_2$O), 4.78-4.86(br. m, 1H, CHN), 7.12-7.42(m, 10H, Ph), yield = 42%, $t_R$ = 8.65 min, (M$^+$ + 1) = 511.05. |
| ⌇⌇⌇-CH(iPr)(Bn) | $^1$H NMR δ(CDCl$_3$): 0.82-1.56(four s, and four m, 27H, $^t$Bu, CH, CH$_2$, and CH$_3$), 3.20-3.52(a series of m, 2H, CH$_2$N), 3.60-3.88(a series of m, 2H, CH$_2$O), 4.20-4.60(a series of m, one s, 4H, CH$_2$O, CHN), 7.21-7.37(m, 5H, Ph), yield = 24%, $t_R$ = 9.23 min, (M$^+$ + 1) = 477.32. |

Synthesis of 4-Fmoc-6-hydroxymethyl-3-substituted-piperazin-2-one (6): A suspension of 19 mmol of (5) and 2 g of 10% palladium on carbon in 200 mL of ethanol was hydrogenated at room temperature and atmospheric pressure overnight. The suspension was filtered through celite, and concentrated. The residue was redissolved in 40 mL of 50% trifluoroacetic acid in dichloromethane. The solution was stirred at room temperature for 2 hours, and then concentrated. The residue was redissolved in 60 mL of tetrahydrofuran/40 mL of water, and neutralized with solid sodium bicarbonate, followed by the addition of 40 mmol of solid sodium bicarbonate, and 20 mmol of Fmoc chloride. The mixture was then stirred at room temperature for 2 hours, diluted with 300 mL of ethyl acetate, and the layers separated. The organic layer was dried over magnesium sulfate, concentrated, and purified by silica gel column chromatography.

| R | Analytical Data for Compound (6) |
|---|---|
| ⌇⌇⌇-CH(Ph)(⌇) | $^1$H NMR (CDCl$_3$): 2.15-2.32(br. m, 1H, CH$_2$—Ph), 2.70-2.81(br. m, 1H, CH$_2$—Ph), 3.0-3.32(br. m, 3H, CHN, and CH$_2$N), 3.47-3.65(br. m, 3H, CH$_2$O, and CHN), 3.95-4.22(two m, 2H, CH, and CHN), 4.32-4.48(br. m, 2H, CH$_2$O), 4.84-4.92(br. m, 1H, NH), 6.73-6.83(br. m, 1H, Ph), 6.92-7.01(m, 1H, Ph), 7.08-7.82(a series of m, 11H, Ph, and fulvene), yield = 65%, $t_R$ = 5.78 min, (M$^+$ + 1) = 443.07. |
| ⌇⌇⌇-CH(iPr)(⌇) | $^1$H NMR δ (CDCl$_3$): 0.6-1.5(br. peaks, 7H, CH$_2$, and CH$_3$), 1.20-1.42(br. m, 1H, CH$_2$), 1.72-2.02(two br. peaks, 1H, CH), 2.74-2.86(t, ½H, CHN), 2.74-3.74(a series of br. peaks, 5H, CH$_2$O, CH$_2$N, and CHN), 4.16-4.22(br. m, 1H, CH), 4.52-4.74(br. m, 2H, CH$_2$O), 7.24-7.82(a series of m, 8H, fulvene), yield = 34%, $t_R$ = 5.72 min, (M$^+$ + 1) = 408.95 |
| ⌇⌇⌇-C(CH$_3$)$_3$ | $^1$H NMR δ (CDCl$_3$): 0.73-1.00(m, 7H, CH$_3$), 2.2-2.3(br. m, 0.5H, CH), 2.74-4.62(a series of br. peaks, 12H, CH$_2$N, CH$_2$O and CHN), 3.68(s, 3H, CH$_3$O), 7.26-7.77(m, 9H, fulvene), yield = 45% (3 steps), $t_R$ = 5.34 min, (M$^+$ + 1) = 394.93 |

Synthesis of 4-Fmoc-5-substituted-6-oxo-piperazine-2-carboxylic acid (7): Compounds (7) were prepared by several methods.

(a) To a biphasic solution of 10 mmol of (6) in 180 mL of acetonitrile, 180 mL of carbon tetrachloride, and 240 mL of water, cooled to 0° C., was added 112 mmol of solid sodium periodate, followed by 340 mg of ruthenium chloride. The reaction was allowed to warm up to room temperature, stirred for 2 hours, and then filtered through celite. The layers were separated, and the aqueous layer re-extracted with 2×75 mL of ethyl acetate. The organic layers were combined, dried over magnesium sulfate, and concentrated.

(b) A solution of 12 mmol of (6), and 59 mmol of PDC in 60 mL of dry dimethylformamide was stirred at 48° C. under nitrogen for ~5 hours, cooled to room temperature, and poured over 600 mL of water, and extracted with 3×200 mL of dichloromethane. The organic layers were combined, dried over magnesium sulfate, and concentrated.

(c) To a solution of 17 mmol of (6) in 350 mL of acetone kept at room temperature was added 25 mL of Jones reagent (prepared from 8.0 g of chromic acid, 17.4 mL of water, and 6.9 mL of concentrated sulfuric acid). The mixture was stirred for 1 hour, 150 mL of isopropanol was added, and the mixture filtered through celite. The celite was washed with ethyl acetate. The organic layers were combined and concentrated. The residue was dissolved in 250 mL of ethyl acetate and washed with 2×50 mL of water, dried over magnesium sulfate, and concentrated.

(d) To a solution of 81 mmol alcohol (6) in 810 mL of acetonitrile kept at room temperature, was added phosphate buffer solution (prepared with 7.2 g of sodium phosphate monobasic, and 14.3 g of sodium phosphate dibasic in 295 mL of water), followed by the addition of 3.3 g (20.7 mmol) of TEMPO, and 18.6 g (164.4 mmol) of sodium chlorite, and the biphasic solution placed in an oil bath kept at 43° C., and then a solution of 43.3 mL (25.9 mmol) of sodium hypochlorite solution (prepared by mixing 19.3 mL of 10-13% sodium hypochlorite solution, and 24 mL of water) was added slowly. The reaction was stirred at 43° C. for 4 hours. The solution was cooled to room temperature, and a solution of 200 mL of 10% sodium hydrogen sulfite solution was added, stirred for 10 minutes, diluted with 500 mL of ethyl acetate, and the layers separated. The organic layer was washed with 1×100 mL of brine, 1×160 mL of 1N hydrochloric acid solution, dried over sodium sulfate, and concentrated.

The products (7) were purified by silica gel column chromatography.

| R | Analytical Data for Compounds (7) |
|---|---|
| Ph | $^1$H NMR δ(CDCl$_3$): 2.36-2.45(dd, 1H, CH$_2$—Ph), 2.62-2.76(m, ½H, CH$_2$—Ph), 2.82-2.98(m, ½H CH$_2$—Ph), 3.13-3.25(m, 1H, CH$_2$N), 3.98-4.64(a series of m, 6H, CHN, CH$_2$O, CH$_2$, and CH), 4.87(br. m, fra ½H, NH), 6.85(br. s, 1H, Ph), 7.0-7.40(a series of m, 12H, Ph and fulvene), 9.18-9.40(br. d, 1H, CO$_2$H), $t_R$ = 5.91 min, (M$^+$ + 1) = 457.37. |
|  | $^1$H NMR δ(CDCl$_3$): 0.64-1.02(overlapping t, 6H, CH$_3$), 1.02-1.68(three br. m, 2H, CH$_2$), 1.96-2.16(br. m, 1H, CH), 2.88-3.18(m, 1H, CH$_2$N), 3.85-4.12(three m, 2H, CH$_2$N, and CHN), 4.18-4.35(m, 1H, CH), 4.55-4.72(m, 2H, CH$_2$), 4.75-4.86(br. m, 1H, NH), 7.28-7.82(a series of m, 8H, fulvene), 9.1-9.26(two br. s, 1H, CO$_2$H), $t_R$ = 5.86 min, (M$^+$ + 1) = 423.20. |
|  | $^1$H NMR δ(CDCl$_3$): 0.62-1.03(m, 7H, CH$_3$), 1.90-2.05(br. m, 1H, CH), 2.87-4.60(a series of br. peaks, 8H, CH$_2$N, CH$_2$O and CHN and CH), 7.29-7.80(m, 9H, fulvene), yield = 61%, $t_R$ = 5.52 min, (M$^+$ + 1) = 409.11 |

Method B: Intermediates Di-Boc-2-substituted-(2-amino-3-benzyloxy-propyl-amino)-ethanols (4), prepared as described in method A, were oxidized to the acid using TEMPO/isocyanuric acid reagent, and then esterified with iodomethane to give fully protected reduced dipeptide analogs (8). Deprotection of the Boc groups, and the benzyl ether, gave 3-substituted 5-hydroxymethyl-piperazin-2-ones, which were protected as the Fmoc derivatives to give (6), which were oxidized to the final product as described in method A.

Synthesis of Di-Boc-(2-amino-3-benzyloxy-propylamino)-2-substituted acetic acid methyl ester (8): To a suspension of 76 mmol of (4) in 680 mL of acetone, and 210 mL of a saturated sodium bicarbonate solution, kept at 0° C., was added 21 mmol of solid sodium bromide, and 2.9 mmol of TEMPO, followed by the slow addition of 156 mmol of trichloroisocyanuric acid. The reaction was stirred for 30 minutes at 0° C., and then at room temperature overnight, acidified with a solution of 1N hydrochloric acid, and extracted with 2×300 mL of ethyl acetate. The organic layer was washed with 3×50 mL of 1N hydrochloric acid, dried over magnesium sulfate, and concentrated. The residue was redissolved in 40 mL of dry dimethylformamide and 95 mmol of solid sodium bicarbonate, and 112 mmol of iodomethane was added, and the mixture stirred at room temperature under nitrogen until HPLC showed the reaction was complete; the solution was then diluted with 200 mL of ethyl ether, and washed with 2×100 mL of water, dried over magnesium sulfate, and concentrated. The products (8) were purified by silica gel column chromatography.

| R | Analytical Data for Compounds (8) |
|---|---|
| Ph | $^1$H NMR δ(CDCl$_3$): 1.41(s, 9H, $^t$Bu), 1.46(s, 9H, $^t$Bu), 2.44-2.58 (d, ½H, CH$_2$—PH), 2.66-2.88(d, ½H, CH$_2$—Ph), 3.16-3.46(three sets of m, 5H, CH$_2$—Ph, CH$_2$N, and CH$_2$O), 3.72(s, 3H, CH$_3$O), 3.75-4.05(two m, 1H, CHN), 4.42(s, CH$_2$O), 4.95-5.10(d, ½H, NH), 5.30-5.38(d, ½H, NH), 7.10-7.38(m, 10H, Ph), yield = 62%, $t_R$ = 7.75 min, (M$^+$ + 1) = 529.03. |
| H | $^1$H NMR δ(CDCl$_3$): 1.41(s, 9H, $^t$Bu), 1.42(s, 9H, $^t$Bu), 3.30-3.60(br. m, 4H, CH$_2$N, CH$_2$O), 3.70(s, 3H, CH$_3$O), 3.75-3.95(m, 2H, CH$_2$N), 4.51(s, 2H, CH$_2$O), 5.0-5.08(br. s, 1H, NH), 7.25-7.37(m, 5H, Ph), yield = 47% $t_R$ = 7.28 min, (M$^+$ + 1) = 453.17. |

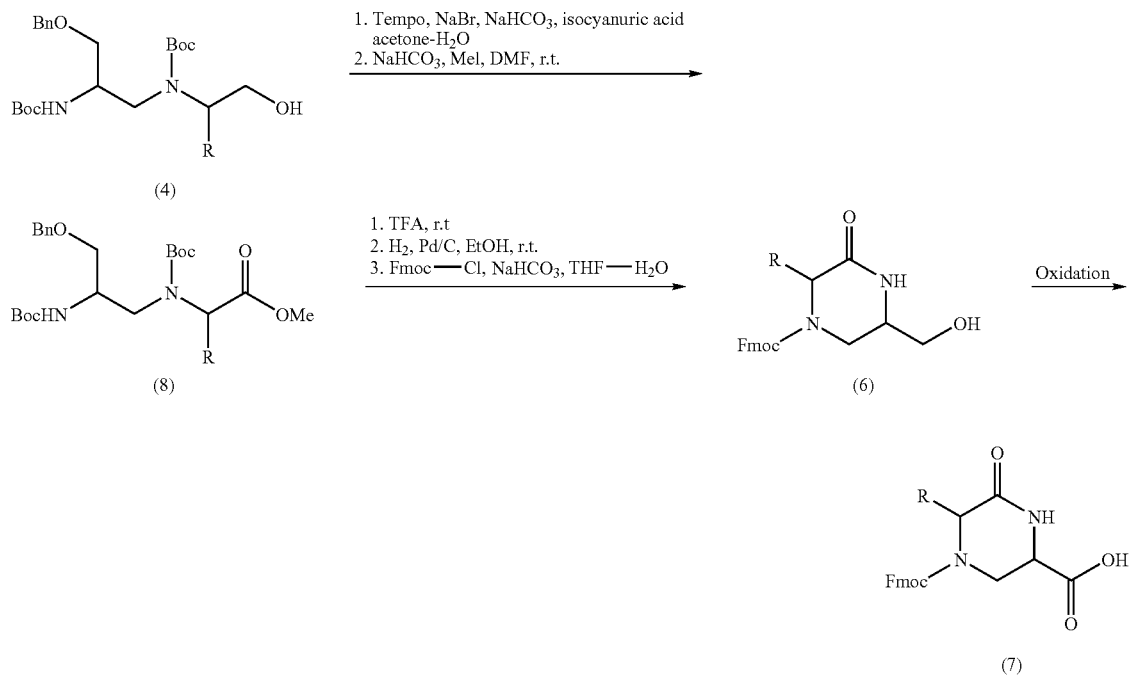

Synthesis of 4-Fmoc-6-hydroxymethyl-3-substituted-piperazin-2-one (6): A solution of 36 mmol of (8) in 40 mL of 50% trifluoroacetic acid in dichloromethane was stirred at room temperature for 2 hours, and then poured in 200 mL of saturated sodium bicarbonate solution. The layers were separated, and the organic layer concentrated. The residue was redissolved in 100 mL of ethyl acetate, and washed with 2×50 mL of water, dried over magnesium sulfate, and concentrated. The residue was dissolved in 100 mL of ethanol, and 5 g of 10% palladium on carbon and 35 mL of a 1N hydrochloric acid solution was added, and the mixture hydrogenated at room temperature and atmospheric pressure until HPLC showed the reaction was complete; the solution was then filtered through celite and concentrated. The residue was redissolved in 80 mL of ethyl acetate, 70 mmol of sodium bicarbonate in 30 mL of water was added, and the mixture stirred at room temperature overnight. The ethyl acetate was removed and 100 mL of tetrahydrofuran was added, followed by 178 mmol of solid sodium bicarbonate and 43 mmol of Fmoc chloride, and the mixture was stirred until HPLC showed it was complete, diluted with 300 mL of ethyl acetate, and the layers separated. The organic layer was washed with 2×50 mL of water, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

General Common Synthetic Scheme for the Preparation of Ketopiperazine Scaffolds Applicable to Compounds With or Without Functionalized R sidechains Methods C, E, F Method C: (2-Fmoc-amino-3-R'—O-propylamino)-2-substituted acetic acid methyl esters (10) were prepared by reductive amination of Fmoc O-protected serinal (9) with α-amino esters (2), using either sodium cyanoborohydride or sodium triacetoxyborohydride as the reducing agent. The Fmoc O-protected serinal (9) required for the reductive amination was prepared according to method D, either by reduction of the ester (12) by di-isobutylaluminun hydride, by oxidation of Fmoc O-protected serinol (13) with Dess-Martin periodinane, or by reduction of the Fmoc O-protected serine Weinreb amide (14) with lithium aluminum hydride. The preferred method for the preparation of Fmoc O-protected serinals (9) was the reduction of the Weinreb amide analog. (2-Fmoc-amino-3-R'—O-propylamino)-2-substituted acetic acid methyl esters (10) were then N and O deprotected, cyclized, and Fmoc protected to give 3-substituted 6-hydroxymethyl-piperazin-2-ones (6), which were then oxidized to the final product as described in method A.

The protecting group (R') on the hydroxyl group of Fmoc-O-protected serinal (9) used in the synthesis depends on the nature of the side chain R of the amino ester. When R contained no functional groups, the side chain of Fmoc serine was protected as the 'Bu ether. When R contained functional groups, the side chain of Fmoc serine was protected as the trityl ether.

Method C

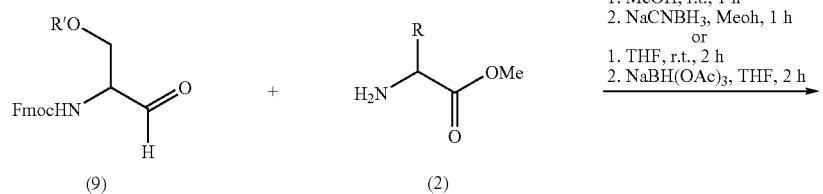

1. MeOH, r.t., 1 h
2. NaCNBH$_3$, Meoh, 1 h
   or
1. THF, r.t., 2 h
2. NaBH(OAc)$_3$, THF, 2 h

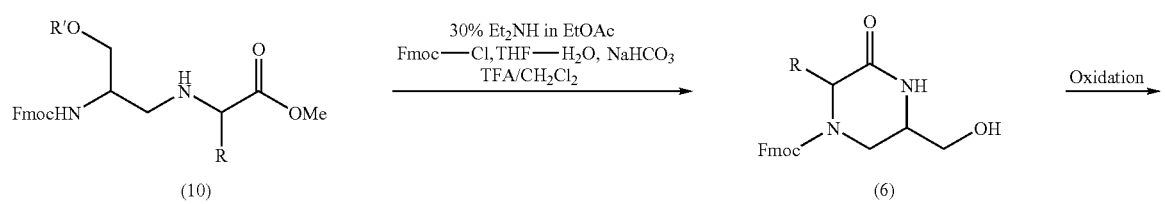

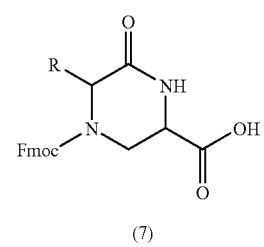

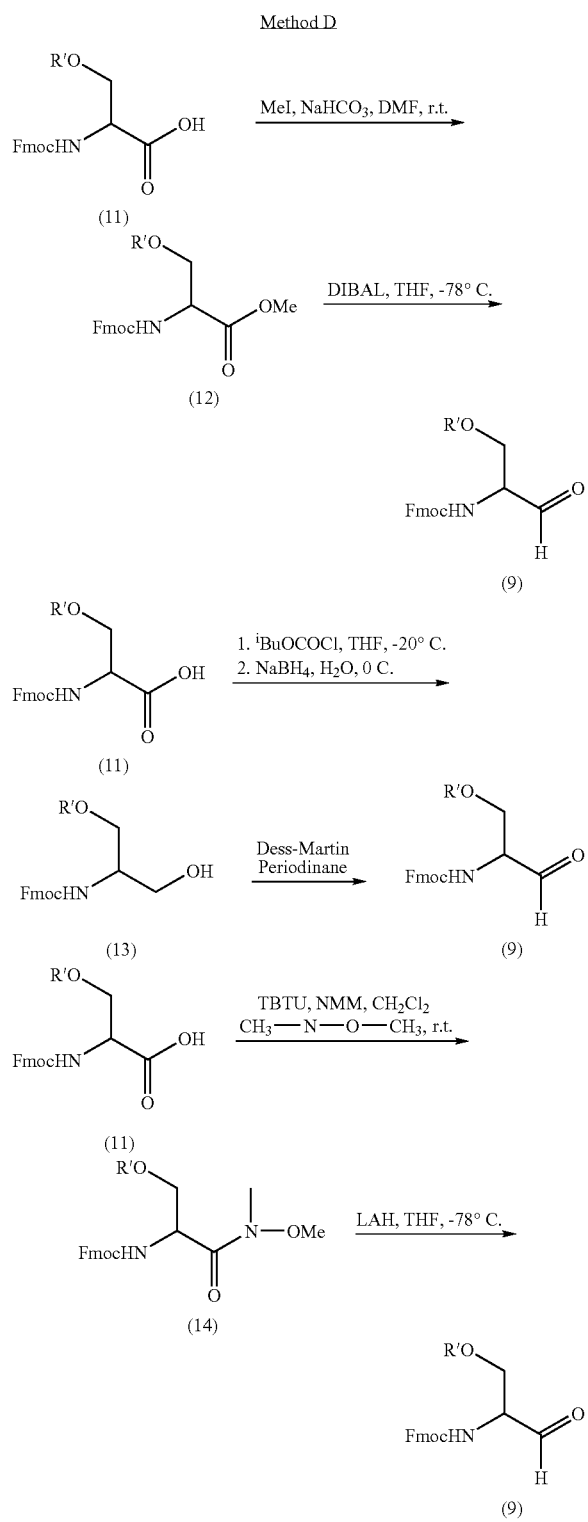

Method D: Synthesis of various Fmoc-O-protected serinals (9). Synthesis of Fmoc-O—R' serine methyl ester (12): A slight suspension of 80 mmol of Fmoc O—R' serine (11), 10.0 g (120 mmol) of solid sodium bicarbonate, and 10.0 mL (160 mmol) of iodomethane in 80 mL of dry dimethylformamide, kept under nitrogen, was stirred at room temperature overnight. The reaction mixture was then poured over 500 mL of water, and the solid filtered. The solid was redissolved in 800 mL of ethyl acetate, and washed with 1×200 mL of water, dried over magnesium sulfate, and concentrated. No purification was required.

| R' | Analytical Data for Compounds (12) |
|---|---|
| $^t$Bu | $^1$H NMR δ (CDCl$_3$): 1.14 (s, 9H, $^t$Bu), 3.57-3.70 (m, 1H, CH$_2$—O), 3.75 (s, 3H, O—CH$_3$), 3.79-3.83 (m, 1H, CH$_2$—O), 4.01-4.50 (a series of multiples, 4H), 5.64-5.68 (d, 1H, NH), 7.28-7.78 (8H, fulvene), yield = 93% $t_R$ = 7.8 min. |
| Trt | $^1$H NMR δ (CDCl$_3$): 3.42-3.48 (m, 1H, CH$_2$—O), 3.59-3.66 (m, 1H, CH$_2$—O), 3.81 (s, 3H, CH$_3$—O), 4.10-4.18 (m, 1H, CH), 4.36-4.42 (m, 2H, CH$_2$—O), 4.50-4.57 (m, 1H, CH—N), 5.73-5.78 (d, 1H, NH), 7.22-7.82 (8H, fulvene), yield = quant., $t_R$ = 9.04 min. |

Synthesis of Fmoc-O—R' serinol (13): To a solution of 10.0 mmol of Fmoc O—R' serine (11) in 50 mL of dry tetrahydrofuran, kept at −20° C. under nitrogen, was added 1.77 mL (12.7 mmol) of triethyl amine, followed by the slow addition of 1.57 mL (12.0 mmol) of isobutylchloroformate. The mixture was stirred for 30 minutes, and then poured slowly over an ice-cold solution of 3.77 g (99.6 mmol) of sodium borohydride in 10 mL of water, keeping the temperature below 5° C. The reaction was stirred at 0° C. for minutes, and then quenched with 1N hydrochloric acid solution. The reaction mixture was diluted with 100 mL of ethyl acetate, and the layers separated. The organic layer was washed with 2×25 mL of 1N hydrochloric acid solution, 2×25 mL of water, dried over magnesium sulfate and concentrated. The compounds were purified by silica gel column chromatography.

| R' | Analytical Data for Compounds (13) |
|---|---|
| $^t$Bu | $^1$H NMR δ (CDCl$_3$): 1.14 (s, 9H, $^t$Bu), 2.90-2.95 (d, 1/2H, CH$_2$—O), 3.63 (d, 2H, CH$_2$—O), 3.65-3.93 (m, 3H, CH$_2$—O), 4.20-4.35 (t, 1H, CH), 4.35-4.45 (d, 2H, CH$_2$), 5.50-5.57 (d, 1H, NH), 7.26-7.8 (8H, fulvene), yield = 85%, $t_R$ = 6.42 min. |
| Trt | $^1$H NMR δ (CDCl$_3$): 3.24-3.32 (br. d, 1H, CH$_2$—O), 3.30-3.45 (br. m, 1H, CH$_2$—O), 3.60-3.987 (br. m, 3H, CH$_2$—O, and CH—N), 4.13-4.22 (br. m, 1H, CH), 4.32-4.40 (br. d, 2H, CH$_2$), 5.24-5.32 (br. d, 1H, NH), 7.16-7.76 (23H, fulvene, and Trt), yield = 92%, $t_R$ = 8.39 min. |

Synthesis of Fmoc-O—R' serine Weinreb amide (14): A suspension of 20.2 mmol of Fmoc O—R' serine (11), 6.98 g (21.6 mmol) of 2-(1H-benzotriazol-1-yl)-1,1,3,3-tetramethyluronium tetrafluoroborate (TBTU), and 2.5 mL (22.7 mmol) of N-methyl-morpholine in 80 mL of dry dichloromethane was stirred at room temperature under nitrogen for 20 minutes, and then 3.02 g (31 mmol) of N,O-di-methyl-hydroxylamine hydrochloride and 3.3 mL (30 mmol) of N-methyl-morpholine were added, and the suspension stirred at room temperature overnight. The solution formed was then concentrated to dryness, repartitioned between 200 mL of ethyl acetate and 100 mL of water, washed with 2×40 mL of 1N hydrochloric acid solution and then 2×40 mL of saturated sodium bicarbonate solution, dried over magnesium sulfate, and concentrated. No purification was required.

| R' | Analytical Data for Compounds (14) |
|---|---|
| $^t$Bu | $^1$H NMR δ (CDCl$_3$): 1.45 (s, 9H, $^t$Bu), 3.30 (s, 3H, CH$_3$—N), 3.55-3.7 (m, 2H, CH$_2$—O), 3.76 (s, 3H, CH$_3$—O), 4.19-4.26 (m, 1H, CH), 4.30-4.38 (m, 2H, CH$_2$—O), 4.82-4.91 (broad m, 1H, CHN), 5.68-5.75 (d, 1H, NH), 7.2-7.8 (8H, fulvene), yield = quant., $t_R$ = 6.59 min. |

-continued

| R' | Analytical Data for Compounds (14) |
|---|---|
| Trt | $^1$H NMR δ (CDCl$_3$): 3.24 (s, 3H, CH$_3$N), 3.34-3.46 (m 2H, CH$_2$O), 3.62 (s, 3H, CH$_3$O), 4.15-4.37 (two m, CH$_2$, CH), 4.86-4.98 (m 1H, CHN), 5.80-5.86 (d, 1H, NH), 7.18-7.8 (a series of m, 23H, Trt and fulvene), yield = quant., $t_R$ = 8.0 min. |

Synthesis of Fmoc-O—R' serinal (9) from ester (12): To a solution of 3.5 mmol of (12) in 5 mL of tetrahydrofuran, kept at −78° C. under nitrogen, was added slowly 10 mL of 1N diisobutyl aluminum hydride (DIBAL) solution, stirred for 15 minutes, and quenched by the slow addition of a saturated solution of sodium and potassium tartrate. The reaction was allowed to warm up to room temperature, diluted with 50 mL of ethyl acetate, and 50 mL of a saturated solution of sodium and potassium tartrate was added. The layers were separated, and the aqueous layer re-extracted with 1×50 mL of ethyl acetate. The organic layers were combined, dried over magnesium sulfate, and concentrated. Compounds (9) were used without further purification in the next step.

| R' | Analytical Data for Compounds (9) |
|---|---|
| $^t$Bu | $^1$H NMR δ (CDCl$_3$): 1.16 (s, 9H, $^t$Bu), 3.59-3.66 (dd, 1H, CH$_2$O), 3.90-3.98 (dd, 1H, CH$_2$O), 4.20-4.27 (t, 1H, CH), 4.32-4.45 (two m, 3H, CHN, and CH$_2$O), 5.64-5.74 (br. d, 1H, NH), 7.28-7.35 (m, 2H, fulvene), 7.36-7.44 (m, 2H, fulvene), 7.58-7.65 (d, 2H, fulvene), 7.73-7.78 (d, 2H, fulvene), 9.62 (s, 1H, CHO). |
| Trt | $^1$H NMR δ (CDCl$_3$): 3.53-3.61 (dd, 1H, CH$_2$O), 3.66-3.75 (dd, 1H, CH$_2$O), 4.33-4.47 (two m, 4H, CHN, CH, and CH$_2$), 5.66-5.75 (d, 1H, NH), 7.20-7.81 (a series of m, 23H, Trt, and fulvene), 9.6 (s, 1H, CHO). |

Synthesis of Fmoc-O—R' serinal (9) from alcohol (13): To a solution of 80 mmol of Fmoc-O—R' serinol (13) in 200 mL of dry dichloromethane, kept at room temperature under nitrogen, was added 88 mmol of Dess-Martin periodinane, and the reaction was stirred for 2.5 hours and quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated.

Synthesis of Fmoc-O—R' serinal (9) from Weinreb amide (14): To a solution of 8.8 g (20.2 mmol) of crude Fmoc-O—R' serine Weinreb amide intermediate (14) in 60 mL of dry tetrahydrofuran, cooled to −78° C. under nitrogen, was added 30 mL of 1N lithium aluminum hydride solution in tetrahydrofuran. The solution was stirred for 15 minutes and then quenched by the slow addition of 30 mL of a 1.4N solution of potassium hydrogen sulfate. After warming up to room temperature, the solid was filtered and the filtrate concentrated to dryness. The residue was repartitioned between 50 mL of ethyl acetate and 25 mL of 1N hydrochloric acid solution. The layers separated, and the organic layer was dried over magnesium sulfate, filtered, and concentrated.

Synthesis of (2-Fmoc-amino-3-R'-O-propylamino)-2-substituted acetic acid methyl ester (10): compounds (10) were prepared by reductive amination using sodium cyanoborohydride or sodium triacetoxyborohydride as the reducing agent.

Sodium cyanoborohydride method: To a solution of 8.5 mmol of (2) hydrochloride salt in 20 mL of methanol, kept at room temperature under nitrogen, was added 2.3 mmol of solid potassium hydroxide, and the mixture stirred for 25 minutes. A solution of Fmoc-O—R' serinal (9) in 10 mL of methanol was added to the above suspension, and the reaction mixture was stirred for 1 hour. A solution of 8.5 mL of 1N sodium cyanoborohydride in tetrahydrofuran was added slowly, and the reaction stirred for another 1 hour, filtered, and concentrated. The residue was partitioned between ethyl acetate and water, and the organic layer washed with 1×20 mL of saturated sodium bicarbonate, dried over sodium sulfate, and concentrated.

Sodium triacetoxyborohydride method: A suspension of 21 mmol of (2) hydrochloride salt, and 2.9 mL (21 mmol) of triethyl amine in 50 mL of dry tetrahydrofuran, was stirred at room temperature for 45 min, and then a solution of ~20 mmol crude Fmoc-(O—R')-serinal (9) in 30 mL of tetrahydrofuran was added, followed by 1.7 g of 4 A powdered molecular sieves, and the suspension was stirred for an additional 2 h. 6.4 g (30 mmol) of solid sodium triacetoxyborohydride was added, and the suspension stirred at room temperature overnight. The suspension was diluted with methanol, the molecular sieves filtered, and the filtrate concentrated. The residue was partitioned between 100 mL of ethyl acetate and 50 mL of water. The organic layer was dried over sodium sulfate, filtered, and concentrated.

Compounds (10) were purified by silica gel column chromatography.

| R' | R | Analytical Data Compounds (10) |
|---|---|---|
| $^t$Bu | 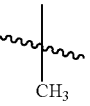 | $^1$H NMR δ(CDCl$_3$): 1.17(s, 9H, $^t$Bu), 1.26-1.32(d, 3H, CH$_3$), 2.68-2.80(br. m, 2H, CH$_2$N), 3.32-3.56(two br. m, 2H, CH$_2$O), 3.72(s, 3H, CH$_3$O), 3.66-3.82(m, 1H, CHN), 4.18-4.28(t, 1H, CH), 4.30-4.46(d, 2H, CH$_2$), 5.34-5.44(br. d, 1H, NH), 7.25-7.44(two m, 4H, fulvene), 7.59-7.64(d, 2H, fulvene), 7.74-7.79(d, 2H, fulvene), yield = 57%, $t_R$ = 4.93 min, (M$^+$ + 1) = 455.67. |
| $^t$Bu | 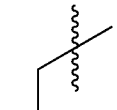 | $^1$H NMR δ(CDCl$_3$): 0.88-0.98(br. t, 6H, CH$_3$), 1.21(s, 9H, $^t$Bu), 1.26-1.34(m, 2H, CH$_2$), 1.44-1.54(m, 1H, CH), 2.58-2.86(two m, 1H, CH$_2$N), 3.25-3.35(m, 1H, CH$_2$N), 3.37-3.58(two m, 2H, CH$_2$O), 3.72-3.80(br. m, 1H, CHN), 4.14-4.31(m, 1H, CH), 4.32-4.45(br. d, 2H, CH$_2$O), 5.34-5.44(br. d, 1H, NH), 7.30-7.84(a series of m, 8H, fulvene), yield = 50%, $t_R$ = 5.66 min, (M$^+$ + 1) = 511.67. |
| $^t$Bu | 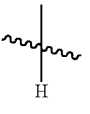 | $^1$H NMR δ(CDCl$_3$): 1.17(s, 9H, $^t$Bu), 2.68-2.78(m, 1H, CH$_2$N), 2.82-2.92(m, 1H, CH$_2$N), 3.35-3.55(m, 4H, CH$_2$N, and CH$_2$O), 3.73(s, 3H, CH$_3$O), 3.75-3.85(m, 1H, CHN), 4.20-4.28(m, 1H, CH), 4.32-4.48(m, 2H, CH$_2$), 5.40-5.50(d, 1H, NH), 7.28-7.8(a series of m, 8H, fulvene), yield = 44%, $t_R$ = 5.02 min, (M$^+$ + 1) = 441.50. |
| $^t$Bu | 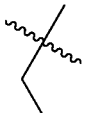 | $^1$H NMR δ(CDCl$_3$): 0.84-0.92(br. t, 3H, CH$_3$), 1.17(s, 9H, $^t$Bu), 1.28-1.35(m, 4H, CH$_2$), 1.48-1.84(two m, 2H, CH$_2$), 2.62-2.82(m, 2H, CH$_2$N), 3.20-3.33(m, 1H, CHN), 3.35-3.54(two m, 2H, CH$_2$O), 3.72(s, 3H, CH$_3$O), 3.64-3.80(m, 1H, CHN), 4.20-4.28(t, 1H, CH), 4.32-4.42(m, 2H, CH$_2$O), 5.34-5.44(br.d, 1H, NH), 7.25-7.79 (a series of m, 8H, fulvene), yield = 65%, $t_R$ = 5.85 min, (M$^+$ + 1) = 441.27. |

| R' | R | Analytical Data Compounds (10) |
|---|---|---|
| Trt | [structure with C(=O), NHTrt] | $^1$H NMR δ(CDCl$_3$): 2.67-2.63(br. m, 2H, CH$_2$CO), 2.65-2.90(br. m, 2H, CH$_2$N), 3.05-3.20(br. m, 2H, CH$_2$O), 3.50-3.64(br. m, 1H, CHN), 3.68 & 3.69(two s, 3H, CH$_3$O), 3.82-3.94(br. m, 1H, CHN), 4.12-4.21(br. m, 1H, CH), 4.24-4.43(br. m, 2H, CH$_2$O), 4.90-4.98(br. d, 1H, NH), 7.15-7.80(a series of m, 23H, fulvene and Trt), yield = 39%, t$_R$ = 8.13 min, (M$^+$ + 1) = 926.99. |
| Trt | [structure with NHTrt] | $^1$H NMR δ(CDCl$_3$): 1.68-1.82(m, 1H, CH$_2$), 1.85-1.99(m, 1H, CH$_2$), 2.12-2.37(m, 2H, CH$_2$CO), 2.58-2.96(a series of four m, 2H, CH$_2$N), 3.08-3.28(br. m, 2H, CH$_2$O), 3.66 & 3.67(two s, 3H, CH$_3$O), 3.76-3.89(br. m, 1H, CHN), 4.15-4.24(br. m, 1H, CH), 4.28-4.41(br. d, 2H, CH$_2$O), 5.10-5.22(br. d, ½H, NH), 5.28-5.35(br. d, ½H, NH), 7.15-7.80(a series of m, 23H, fulvene, and Trt), yield = 43%, t$_R$ = 8.10 min, (M$^+$ + 1) = 940.97. |
| Trt | [structure with HN, =NH, NHPbf] | $^1$H NMR δ(CDCl$_3$): 1.43(s, 6H, CH$_3$), 1.46-1.56(m, 4H, CH$_2$), 2.06(s, 3H, CH$_3$), 2.50(s, 3H, CH$_3$), 2.57(s, 3H, CH$_3$), 2.75-2.80(m, 1H, CH$_2$N), 2.91(s, 2H, CH$_2$), 3.12-3.32 (three br. m, 4H, CH$_2$N), 3.68(s, 3H, CH$_3$O), 4.13-4.21(t, 1H, CH), 4.28-4.38(d, 2H, CH$_2$), 5.12-5.23(br. d, 1H, NH), 5.80-6.12(two br. m, 2H, NH), 7.18-7.80(a series of m, 23H, fulvene, and Trt), yield = 68%, t$_R$ = 7.52 min, (M$^+$ + 1) = 997.91. |
| Trt | [structure with imidazole, N-H] | $^1$H NMR δ(CDCl$_3$): 2.75-2.98(two m, 2H, CH$_2$N), 3.06-3.18(m, 1H, CH$_2$N), 3.22-3.33(m, 1H, CH$_2$N), 3.57 & 3.60(two s, 3H, CH$_3$O), 3.80-3.92(m, 1H, CHN), 4.00-4.08(m, 1H, CH), 4.18-4.30(br. d, 2H, CH$_2$), 7.00-7.80(a series of m, 25H, fulvene, Trt, and Imidazole), yield = 57%, t$_R$ = 7.59 min, (M$^+$ + 1) = 949.79. |
| Trt | [structure with phenyl, O$^t$Bu] | $^1$H NMR δ(CDCl$_3$): 1.26 & 1.27(two s, 9H, $^t$Bu), 2.50-2.61(dd, 1H, CH$_2$—Ph), 2.76-2.86(m, 2H, CH$_2$—Ph, and CH$_2$N), 2.92-3.20(m, 1H, CH$_2$N), 2.92-3.20(m, 2H, CH$_2$O), 3.32-3.46(m, 1H, CH$_2$O), 3.59(s, 3H, CH$_3$O), 3.79-3.88(m, 1H, CHN), 4.18-4.28 (m, 1H, CH), 4.30-4.37(br. d, 2H, CH$_2$O), 5.18-5.26(br. d, 1H, NH), 6.80-6.88(d, 2H, Ph), 6.96-7.02(d, 2H, Ph), 7.18-7.80(a series of m, 23H, fulvene, and Trt), yield = 23%. |
| Trt | [structure with OtBu] | $^1$H NMR δ(CDCl$_3$): 1.11(s, 9H, $^t$Bu), 2.54-2.74(two m, 2H, CH$_2$N), 3.02-3.58(six m, 6H, CH$_2$O, CH$_2$N, and CHN), 3.70(s, 3H, CH$_3$O), 3.83-3.93(m, 1H, CHN), 4.15-4.28(m, 1H, CH), 4.34-4.37(d, 2H, CH$_2$), 5.46-5.53(br. d, 1H, NH), 7.18-7.79(a series of m, 23H, fulvene, and Trt), yield = 45%, (M$^+$ + 1) = 713.42. |
| Trt | [isopropyl structure] | $^1$H NMR δ(CDCl$_3$): 0.80-0.92(m, 7H, CH$_3$), 1.75-1.90(br. m, 1H, CH), 2.6-4.36(a series of m, 9H, CH$_2$O, CH$_2$N, CHN), 3.68(s, 3H, CH$_3$O), 5.5(d, 0.5H, CH), 7.23-7.77(m, 24H, fulvene and Trt), yield = 72%(3 steps), t$_R$ = 6.68 min, (M$^+$ + 1) = 669.10. |

Synthesis of 4-Fmoc-6-hydroxymethyl-3-substituted-piperazin-2-one (6): For the preparation of compounds (6) three steps were required: (a) Fmoc deprotection with concomitant cyclization, (b) Fmoc protection, and (c) hydroxyl group deprotection.

Fmoc group removal and cyclization: A solution of 10 mmol of cyclic compound in 30 mL of 30% diethyl amine in ethyl acetate solution was stirred at room temperature overnight, and then concentrated to dryness.

(a) Fmoc protection: To a biphasic solution of 10 mmol of compound in 20 mL of tetrahydrofuran and 10 mL of water, was added 2.52 g (30 mmol) of solid sodium bicarbonate, followed by 3.36 g (13 mmol) of Fmoc-Cl. The mixture was stirred for 3 hours, diluted with ethyl acetate, the layers separated, and the organic layer washed with water, dried over magnesium sulfate, and concentrated.

(b) Hydroxyl group deprotection: For compounds containing a $^t$Bu ether protecting group: The compounds were deprotected with a solution of 90% trifluoroacetic acid in dichloromethane for 1-2 hours, and then concentrated to dryness. The residue was dissolved in ethyl acetate and washed with a saturated solution of sodium bicarbonate, dried over magnesium sulfate, and then concentrated. For compounds containing a Trt ether protecting group: the compounds were deprotected by adding a solution of 1-10% trifluoroacetic acid in dichloromethane containing 2-10% tri-isopropyl silane. The reaction was instantaneous. The solution was then neutralized by pouring it into a saturated solution of sodium bicarbonate. The layers were separated, dried over sodium sulfate, and concentrated.

Compounds (6) were purified by silica gel column chromatography.

| R | Analytical Data for Compounds (6) |
|---|---|
| [CH$_3$ structure] | $^1$H NMR δ(CDCl$_3$): 1.17-1.35(br. m, 3H, CH$_3$), 2.64-2.85(t, 1H, CH$_2$N), 3.2-3.8(two br. m, 3H, CH$_2$O, and CH$_2$N), 4.18-4.44(br. t, 1H, CH), 4.64-4.90(br. d, 2H, CH$_2$O), 6.70-6.86(br. s, 1H, NH), 7.22-7.82(a series of m, 8H, fulvene), yield = 72%, t$_R$ = 4.64 min, (M$^+$ + 1) = 367.32. |
| [isobutyl structure] | $^1$H NMR δ(CDCl$_3$): 0.64-1.02(m, 6H, CH$_3$), 1.45-1.63(m, 3H, CH$_2$, and CH), 2.65-2.84(m, 1H, CH$_2$N), 2.89-3.76(a series of br. m, 5H, CH$_2$O, and CHN), 4.17-4.28(br. m, 1H, CH), 4.48-4.82(three br. m, CH$_2$O, NH, and OH), 6.95-7.82(a series of br. m, 8H, fulvene), yield = 51%, t$_R$ = 5.43 min, (M$^+$ + 1) = 409.08. |
| [H structure] | $^1$H NMR δ(CDCl$_3$): 3.17-3.78(a series of br. m, 5H, CH$_2$O, CH$_2$N, and CHN), 421-4.27(t, 1H, CH), 4.42-4.68(br. peak, 2H, CH$_2$O), 6.62(br. s, 1H, NH), 7.28-7.81(a series of m, 8H, fulvene), yield = 67%, t$_R$ = 4.50 min, (M$^+$ + 1) = 353.45. |
| [sec-butyl structure] | $^1$H NMR δ(CDCl$_3$): 0.72-0.90(br. peak, 3H, CH$_3$), 1.0-1.40(br. peak, 4H, CH$_2$), 1.48-1.90(three br. peaks, 2H, CH$_2$), 2.68-2.80(t, 1H, CH$_2$N), 3.10-3.70(four br. peaks, 4H, CH$_2$O, CHN, and CH$_2$N), 4.15-4.25(br. peak, 1H, CH), 4.54-4.62(br. d, 2H, CH$_2$O), 7.25-7.80(a series of m, 8H, fulvene), yield = 72%, t$_R$ = 5.77 min, (M$^+$ + 1) = 408.95. |
| [structure with NHTrt, C=O] | $^1$H NMR δ(CDCl$_3$): 2.50-3.38(four overlapping br. m, 7H, CH$_2$—CO, CH$_2$N, CH$_2$O, and CHN), 3.42-3.64(m, ½H, CHN), 3.70-3.88(m, ½H, CHN), 4.16-4.23(br. d, 1H, CH), 4.48-4.68(br. m, 2H, CH$_2$O), 4.95-5.05(br. d, 1H, NH), 6.95-7.80(a series of m, 23H, fulvene and Trt, yield = 83%, t$_R$ = 7.04 min, (M$^+$ + 1) = 652.61. |

| R | Analytical Data for Compounds (6) |
|---|---|
| 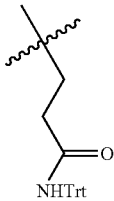 NHTrt | $^1$H NMR δ(CDCl$_3$): 1.67-1.78(br. m, 1H, CH$_2$), 1.81-2.0(br. m, 1H, CH$_2$), 2.10-2.43(br. m, 2H, CH$_2$—CO), 2.58-2.81(br. m, 2H, CH$_2$N), 3.02-3.66(a series of br. m, 4H, CH$_2$O, and CHN), 4.17-4.23(br. m, 1H, CH), 4.40-4.80(br. m, 2H, CH$_2$O), 7.15-7.80(a series of m, 23H, fulvene, and Trt), yield = 80%, $t_R$ = 7.04 min,(M$^+$ + 1) = 666.66. |
| 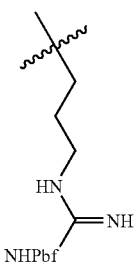 HN NH NHPbf | $^1$H NMR δ(CDCl$_3$): 1.43(s, 6H, CH$_3$), 1.50-1.60(br. m, 4H, CH$_2$), 2.10(s, 3H, CH$_3$), 2.48(s, 3H, CH$_3$), 2.55(s, 3H, CH$_3$), 2.92(s, 2H, CH$_2$), 3.08-3.47(two m, 3H, CH$_2$O, and CH$_2$N), 3.57-3.97(a series of m, 3H, CH$_2$O, and CH$_2$N), 4.15-4.25(br. m, 1H, CH), 4.44-4.74(br. m, 2H, CH$_2$), 7.20-7.80(a series of br. m, 8H, fulvene), yield = 91%, $t_R$ = 6.05 min, (M$^+$ + 1) = 704.71. |
| 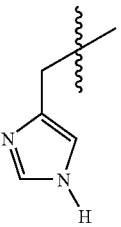 | $^1$H NMR δ(CDCl$_3$): 2.14-2.56(two m, 2H, CH$_2$—Im), 2.90-3.90(a series of m, 4H, CH$_2$N, and CH$_2$O), 4.0-4.74(a series of m, 4H, CHN, CH, CH$_2$), 7.0-7.80(a series of multiples, 25H, fulvene, Im, Trt), yield = 64%, $t_R$ = 5.27 min, (M$^+$ + 1) = 675.08. |
| 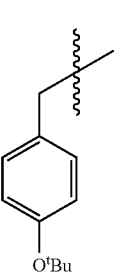 O$^t$Bu | $^1$H NMR δ(CDCl$_3$): 1.29(s, 9H, $^t$Bu) 2.47-2.74(a series of m, 2H, CH$_2$Ph), 2.90-3.04(m, 1H, CH$_2$Ph), 3.06-3.45(three m, 6H, CH$_2$O, and CH$_2$N), 3.89-4.29(three m, 2H, CH, and CHN), 4.32-4.42(m, 1H, CHN), 4.56-4.66(m, 2H, CH$_2$), 6.81-7.80(a series of m, 12H, fulvene, and Ph), yield = 71%, (M$^+$ + 1) = 515.81. |
| 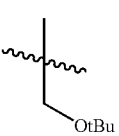 OtBu | $^1$H NMR δ(CDCl$_3$): 1.00 & 1.10(two s, 9H, $^t$Bu), 3.0-3.74(four br. m, 7H, CH$_2$O, CH$_2$N, and CHN), 3.86-4.26(a series of m, 2H, CHN, and CH), 4.42-4.68(br. d, 2H, CH$_2$), 7.26-7.80(a series of br. m, 8H, fulvene), yield = 55%, (M$^+$ + 1) = 439.08. |

Synthesis of 4-Fmoc-5-substituted-6-oxo-piperazine-2-carboxylic acid (7): Compounds (7) were prepared as described in method A. Compounds (7) were purified by silica gel column chromatography.

| R | Analytical Data for Compounds (7) |
|---|---|
| 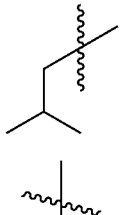 CH$_3$ | $^1$H NMR δ(CDCl$_3$): 1.08-1.20(br. peak, 1.5H, CH$_3$), 1.30-1.38(br. peak, 1.5H, CH$_3$), 2.86-3.07(br. m, 1H, CH$_2$N), 3.83-3.97(br. m, 1H, CH$_2$N), 4.18-4.37(a series of br. peaks, 2H, CH and CHN), 4.40-4.74(two br. peaks, 3H, CH$_2$O, and CHN), 7.28-7.82(a series of m, 8H, fulvene), 8.92-9.10(br. s, 1H, CO$_2$H),yield = 51%, $t_R$ = 4.80 min, (M$^+$ + 1) = 381.57. |
| 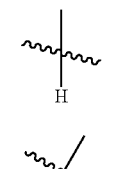 | $^1$H NMR δ(CDCl$_3$): 0.40-1.60(a series of br. peaks, 9H, CH, CH$_2$, and CH$_3$), 2.81-3.09(br. peak, 1H, CH$_2$N), 3.68-3.80(br. peak, 2H, CHN), 3.96-4.32(br. peaks, 2H, CH, and CNH), 4.48-4.68(br. peak, CH$_2$O), 7.26-7.84(a series of m, 8H, fulvene), yield = 50%, $t_R$ = 5.57 min, (M$^+$ + 1) = 423.15. |
| 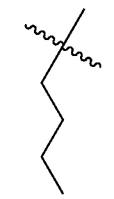 H | $^1$H NMR δ(CDCl$_3$): 3.77-3.99(m, 1H, CHN), 3.90-4.35(a series of m, 5H, CH$_2$N, CH), 4.44-4.57(d, 2H, CH$_2$), 7.3-7.82(a series of m, 8H, fulvene), yield = 48%, $t_R$ = 4.58 min, (M$^+$ + 1) = 367.30. |
| 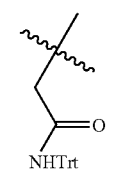 | $^1$H NMR δ(CDCl$_3$): 0.69-1.90(a series of br. peaks, CH$_2$, and CH$_3$), 2.85-3.05(br. peak, 2H, CH$_2$N), 3.65-3.95(two br. peaks, 1H, CHN), 4.00-4.40(two br. peaks, CH$_2$N, and CH), 4.41-4.74(br. peak, 3H, CH$_2$O, and CHN), 7.20-7.80(a series of br. m, 8H, fulvene), yield = 70%, $t_R$ = 5.93 min, (M$^+$ + 1) = 423.42. |
| 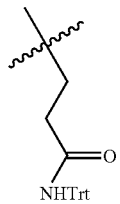 NHTrt | $^1$H NMR δ(CDCl$_3$): 2.51-3.06(a series of m, 2H, CH$_2$—CO), 3.85-4.86(a series of m, 7H, CH$_2$N, CHN, CH, and CH$_2$O), 7.0-7.78(a series of br. m, 23H, fulvene and Trt), yield = 30%, $t_R$ = 7.04 min, (M$^+$ + 1) = 666.79. |
| 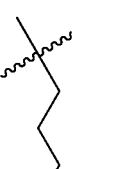 NHTrt | $^1$H NMR δ(CDCl$_3$): 1.74-2.46(a series of br. m, 4H, CH$_2$—CO, and CH$_2$), 3.78-4.06(two m, 2H, CH$_2$N), 4.16-4.68(a series of br. m, 5H, CHN, CH, and CH$_2$O), 7.14-7.82(a series of br. m, 23H, fulvene, and Trt), yield = 47%, $t_R$ = 7.11 min, (M$^+$ + 1) = 680.33. |
| 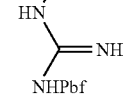 HN NH NHPbf | $^1$H NMR δ(CDCl$_3$): 1.08-1.60(a series of br. peaks, 8H, CH$_2$, and CH$_3$), 2.12(s, 3H, CH$_3$), 2.48(s, 3H, CH$_3$), 2.57(s, 3H, (CH$_3$)), 2.92(s, 2H, CH$_3$), 3.10-3.25(br. m, 2H, CH$_2$N), 3.82-4.28(a series of br. m, 4H, CH$_2$N, CHN, CH), 4.40-4.70(br. m, 3H, CHN, and CH$_2$O), 7.20-7.80(a series of br. m, 8H, fulvene), yield = 42%, $t_R$ = 6.15 min,(M$^+$ + 1) = 718.69. |
| 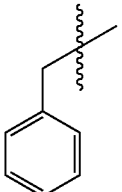 O$^t$Bu (benzyl with OtBu) | $^1$H NMR δ(CDCl$_3$): 1.28 & 1.34(two s, 9H, $^t$Bu), 2.42-3.64(a series of br. m, 5H, CH$_2$N, CHN, and CH$_2$Ph), 4.0-4.76(a series of br. m, 4H, CHN, CH, and CH$_2$O), 6.60-6.96(br. m, 4H, Ph), 7.20-7.80(a series of br. m, 8H, fulvene), yield = 67%, (M$^+$ + 1) = 529.17. |
| OtBu | $^1$H NMR δ(CDCl$_3$): 0.96 & 1.10(two s, 9H, $^t$Bu), 3.04-3.18(br. m, 0.5H, CH$_2$N), 3.30-3.94(four br. m, 3.5H, CH$_2$N, and CH$_2$O), 3.98-4.32(br. m, 2H, CH, and CHN), 4.33-4.74(two br. m, 3H, CHN, CH$_2$O), 7.28-7.80(a series of m, 8H, fulvene), yield = 60%, (M$^+$ + 1) = 453.37. |

Method E: (2-Fmoc-amino-3-hydroxy-propyl-Cbz-amino)-2-substituted acetic acid methyl ester (15) were prepared by reductive amination of Fmoc serinal (OR') (9) with an (x amino ester (2), using either sodium cyanoborohydride or sodium triacetoxyborohydride as the reducing agent. The secondary amine was protected with benzylchloroformate, and then the hydroxyl group deprotected with trifluoroacetic acid solution. Compounds (15) were then Fmoc deprotected. The amino ester intermediates cyclized immediately to form 4-Cbz-3-substituted 6-hydroxymethyl-piperazin-2-ones (16). Fmoc 3-substituted 6-hydroxymethyl-piperazin-2-ones (6) were prepared by protecting group exchange, and then oxidized to the desired products (7) as described in method A.

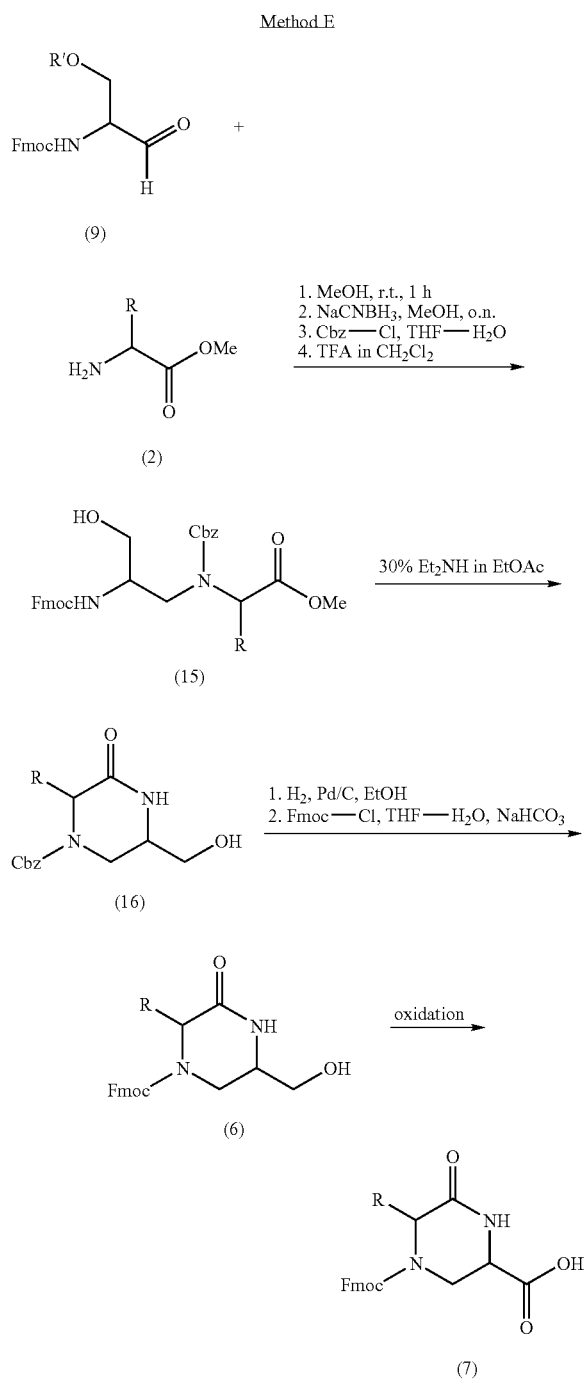

Synthesis of (2-Fmoc-amino-3-hydroxy-propyl-Cbz-amino)-2-substituted acetic acid methyl ester (15): A suspension of 67 mmol of amino ester hydrochloride (2), and 20.9 mmol of solid potassium hydroxide in 80 mL of methanol was stirred at room temperature for 25 minutes, and then added to a suspension of (9) in 250 mL of methanol. The reaction mixture was stirred for 1.5 hours, followed by the slow addition of 70 mL of 1N sodium cyanoborohydride solution in tetrahydrofuran. The reaction was stirred overnight, and then concentrated. The residue was partitioned between 300 mL of tetrahydrofuran and 50 mL of 1N hydrochloric acid solution. The layers were separated, and the organic layer neutralized with a solution of 239 mmol of sodium bicarbonate in 50 mL of water, and then 66 mmol of benzyl chloroformate was added slowly, and the reaction was stirred for 3 hours, diluted with 200 mL of ethyl acetate, and the layers separated. The organic layer was dried over magnesium sulfate, and concentrated. The residue was dissolved in a solution of trifluoroacetic acid in dichloromethane, and stirred at room temperature for 2 hours. The solution was poured over 200 mL of saturated sodium bicarbonate solution. The layers separated, and the organic layer was dried over magnesium sulfate, and concentrated. Compounds (15) were purified by silica gel column chromatography.

| R | Analytical Data Compounds (15) |
|---|---|
| ![structure with O$^t$Bu] | $^1$H NMR δ(CDCl$_3$): 1.38-1.45(d, 9H, $^t$Bu), 2.68-2.78(m, ½H, CH$_2$—CO), 3.0-3.20(m, and s together, 3.5H, CH$_2$—CO, CH$_3$—O, and CH$_2$—O), 3.52-3.60(m, 1H, CH$_3$—O), 3.96-4.40(a series of multiples, 4H), 4.96-5.10(m, 2H, CH$_2$—O), 5.77-5.83 (m, ½H, NH), 7.14-7.79, (a series of m, 23H, Trt and fulvene), yield = 70%, t$_R$ = 9.82 min. |

Synthesis of 4-Cbz-6-hydroxymethyl-3-substituted-piperazin-2-ones (16): A solution of 24 mmol of (15) in 100 mL of 30% diethyl amine in ethyl acetate was stirred at room temperature overnight, and then concentrated to dryness. The compounds were purified by silica gel column chromatography.

| R | Analytical Data for Compounds (16) |
|---|---|
| ![structure with O$^t$Bu] | $^1$H NMR δ (CDCl$_3$): 1.36 (d, 9H, $^t$Bu), 2.60-2.90 (m, 2H, CH$_2$—CO), 2.94-3.20 (br. m, 2H, CH$_2$N), 3.38-3.50 (br. m, 2H, CH$_2$—O), 3.86-4.20 (m, 1H, CH—N), 4.74-4.84 (br, 1H, OH), 5.10-5.15 (s, 2H, CH$_2$—O), 7.26-7.36 (s, 5H, Ph), 7.87-7.95 (s, 1H, NH), yield = 70%, t$_R$ = 4.66 min, (M$^+$ + 1) = 379.41. |

Synthesis of 4-Fmoc-6-hydroxymethyl-3-substituted-piperazin-2-ones (6): A suspension of 15 mmol of (16), and 1.8 g of 10% palladium on carbon in 50 mL of ethanol was hydrogenated at room temperature and atmospheric pressure until HPLC showed that the reaction was complete. The mixture was then filtered through celite, concentrated, and the residue was dissolved in 35 mL of tetrahydrofuran, and 10 mL of water, and then 62 mmol of solid sodium bicarbonate was added, followed by 16 mmol of Fmoc-Cl, and the mixture was stirred for 3 hours, diluted with 100 mL of ethyl acetate and 10 mL of water. The layers were separated, and the organic layer dried over magnesium sulfate, and concentrated. Compounds (6) were purified by silica gel column chromatography.

| R | Analytical Data for Compounds (6) |
|---|---|
| ![structure with OtBu] | $^1$H NMR δ (CDCl$_3$): 1.41 (s, 9H, $^t$Bu), 2.20-2.40 (m, 1/2H, CH$_2$-CO), 2.64-2.96 (m, 1.5H, CH$_2$-CO), 2.98-3.16 (m, 1H, CH$_2$O), 3.2-3.8 (a series of br. m, 4H, CH$_2$O, and CH$_2$N), 4.20-4.38 (two m, CHN, and CH), 4.5-4.67 (br. m, 2H, CH$_2$O), 4.70-4.83 (br. m, 1/2H, NH), 7.27-7.84 (a series of m, 8H, fulvene), yield = 77%, $t_R$ = 5.78 min, (M$^+$ + 1) = 467.82. |

Synthesis of 4-Fmoc-5-substituted-6-oxo-piperazine-2-carboxylic acid (7): Compounds (7) were prepared as described in method A, and purified by silica gel column chromatography.

| R | Analytical Data for Compounds (7) |
|---|---|
| ![structure with OtBu] | $^1$H NMR δ (CDCl$_3$): 1.4 (s, 9H, $^t$Bu), 2.20-2.33 (br. d, 1H, CH$_2$—CO), 2.55-2.67 (br. d, 1H, CH$_2$—CO), 3.25-3.52 (br. m, 2H, CH$_2$N), 3.82-3.94, and 4.07-4.18 (br. peaks, 1H, CHN), 4.20-4.42 (m, 2H, CHN, CH), 4.50-4.72 (m, 2H, CH$_2$—O), 7.30-7.82 (8H, fulvene), 9.20-9.35 (br. s, 1H CO$_2$H), yield = 63%, $t_R$ = 6.60 min, (M$^+$ + 1) = 481.17. |

Method F: (2-Cbz-amino-3-benzyloxy-propylamino)-2-substituted acetic acid methyl esters (20) were prepared by reductive amination of Cbz serinal (OBn) (19) with an α-amino ester (2), using either sodium cyanoborohydride or sodium triacetoxyborohydride as the reducing agent. The Cbz O-Benzyl serinal (19) required for the reductive amination was obtained by oxidation of Cbz serinol (OBn) (18) with Dess-Martin periodinane. Hydrogenation of (20) followed by cyclization gave 3-substituted 6-hydroxymethyl-piperazin-2-ones which was then Fmoc protected to 4-Fmoc-3-substituted 6-hydroxymethyl-piperazin-2-ones (6). The final products (7) were obtained as described in method A.

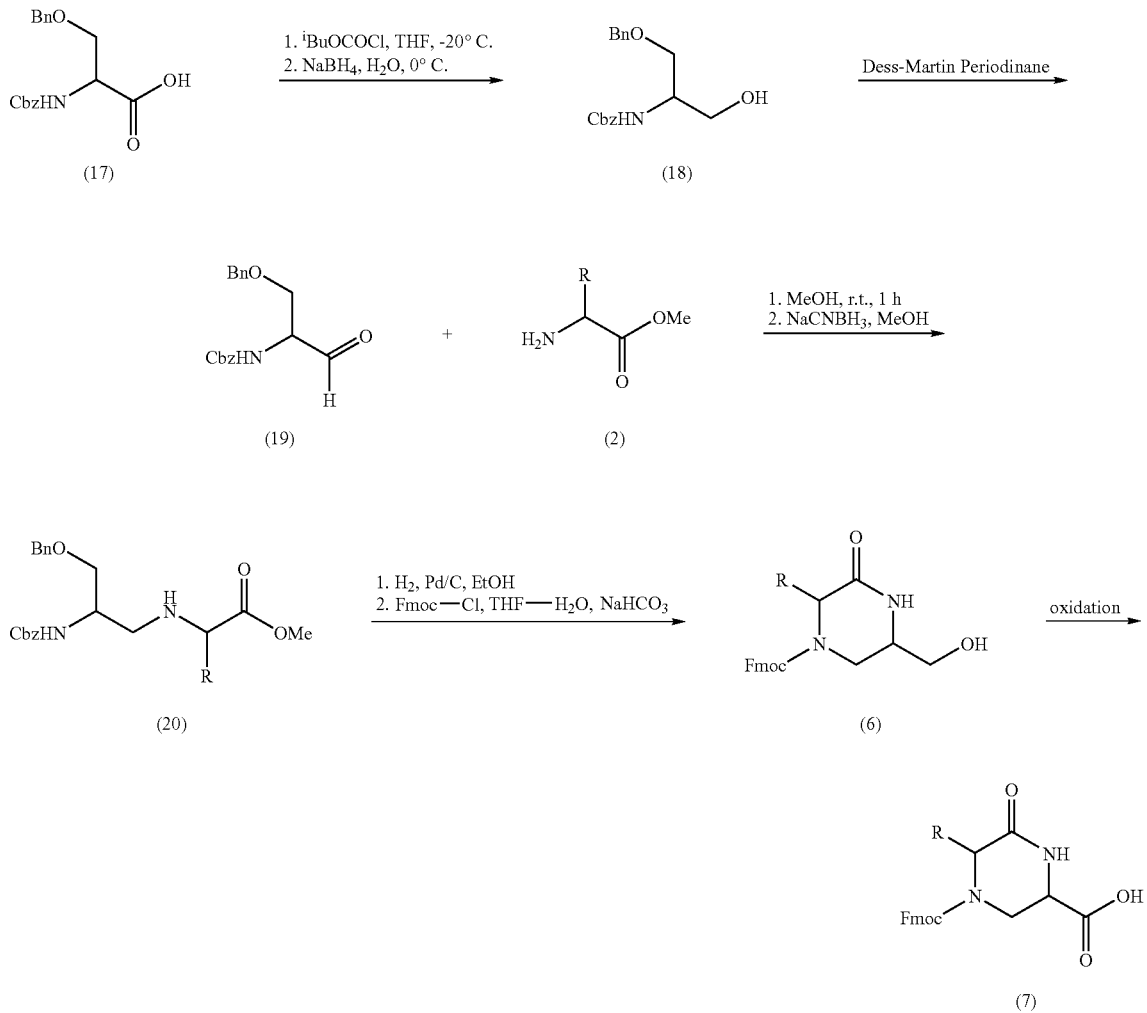

Synthesis of Cbz-serinol (OBn) (18): Compound (18) was prepared as described for compound (13). Compound (18) was obtained in 79% yield after silica gel column chromatography purification. $^1$H NMR δ (CDCl$_3$) 3.57-3.74 (two m, 3H, CHN, and CH$_2$O), 3.76-3.96 (two m, 2H, CH$_2$O), 4.50 (s, 2H, CH$_2$O), 5.10 (s, 2H, CH$_2$O), 5.40-5.50 (br. d, 1H, NH), 7.22-7.38 (m, 10H, Ph); HPLC t$_R$=5.33 min, (M$^+$+Na$^+$)=337.64.

Synthesis of Cbz serinal (OBn) (19): Compound (19) was prepared as described for compound (9). To a solution of 80 mmol of Cbz-O-Bn serinol (18) in 200 mL of dry dichloromethane, kept at room temperature under nitrogen, was added 88 mmol of Dess-Martin periodinane, and the reaction stirred for 2.5 hours, and then quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated. Compound (19) was obtained in 99% crude yield, and used without further purification. $^1$H NMR δ (CDCl$_3$) 3.69-3.78 (dd, 1H, CH$_2$O), 3.99-4.06 (dd, 1H, CH$_2$O), 4.37-4.46 (m, 1H, CHN), 4.47-4.52 (d, 2H, CH$_2$O), 5.14 (s, 2H, CH$_2$O), 5.65-5.75 (br. d, 1H, NH), 7.14-7.48 (a series of m, 9H, Ph), 7.98-8.08 (dd, 1H, Ph), 9.63 (s, 1H, CHO).

Synthesis of (2-Cbz-amino-3-benzyloxy-propylamino)-2-substituted acetic acid methyl esters (20): Compounds (20) were prepared as described for compound (10), but using Cbz serinal (19) as the aldehyde. Compounds (20) were purified by silica gel column chromatography.

| R | Analytical Data for Compounds (20) |
|---|---|
| 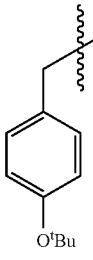 | $^1$H NMR δ (CDCl$_3$): 1.30 (s, 9H, $^t$Bu), 2.50-2.96 (m, 3H, CH$_2$Ph, and CH$_2$N), 3.28-3.54 (m, 3H, CH$_2$N, and CH$_2$O), 3.59 and 3.61 (two s, 3H, CH$_3$O), 3.68-3.86 (m, 1H, CHN), 4.41-4.45 (d, 2H, CH$_2$O), 5.08 (s, 2H, CH$_2$O), 5.25-5.37 (br. t, 1H, NH), 6.84-6.88 (d, 2H, Ph), 6.98-7.04 (d, 2H, Ph), 7.24-7.37 (m, 10H, Ph), yield = 50%, (M$^+$ + 1) = 549.35. |

Synthesis of 4-Fmoc-6-hydroxymethyl-3-substituted-piperazin-2-ones (6): A suspension of 38 mmol of (20) in 160 mL of ethanol, 38 mL of 1N hydrochloric acid, and 20 g of 10% palladium on carbon was hydrogenated at room temperature and atmospheric pressure until HPLC showed that the reaction was complete. The mixture was then filtered through celite, and concentrated to dryness. The residue was diluted with 75 mL of tetrahydrofuran and neutralized with a saturated sodium bicarbonate solution. 106 mmol of solid sodium bicarbonate, and 53 mmol of Fmoc chloride were added, and the reaction stirred at room temperature until HPLC showed the reaction was complete, diluted with 300 mL of ethyl acetate and 300 mL of brine. The layers were separated, and the organic layer washed twice with brine, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

Synthesis of 2,2-disubstituted Ketopiperazine Scaffolds Mimicking Amino Acids Without Functionalized Side Chains Method G The syntheses of 4-Fmoc-5-substituted-6-oxo-piperazine-2-methyl-2-carboxylic acid scaffolds mimicking amino acids without functionalized side chains was carried out using method G. 2-Boc-amino-3-(methoxycarbonyl-1-substituted-methylamino-2-methyl-propionic acid tert-butyl esters (23) were prepared by reductive amination of 2-Boc-amino-2-methyl-3-oxo-propionic acid methyl ester (22) with an α-amino ester (2), using either sodium cyanoborohydride or sodium triacetoxyborohydride as the reducing agent. Compound (22) required for the reductive amination was obtained by oxidation of α-methyl-Boc serine tert-butyl ester (21) with Dess-Martin periodinane. The Boc group of (23) was removed with 2N hydrogen chloride in dioxane, and the amino esters cyclized to unprotected 5-substituted-6-oxo-piperazine-2-methyl-2-carboxylic acid tert-butyl esters (24), which were protected with Fmoc chloride to give 4-Fmoc-5-substituted-6-oxo-piperazine-2-methyl-2-carboxylic acid tert-butyl esters, which were deprotected with trifluoroacetic acid to give the final products (25).

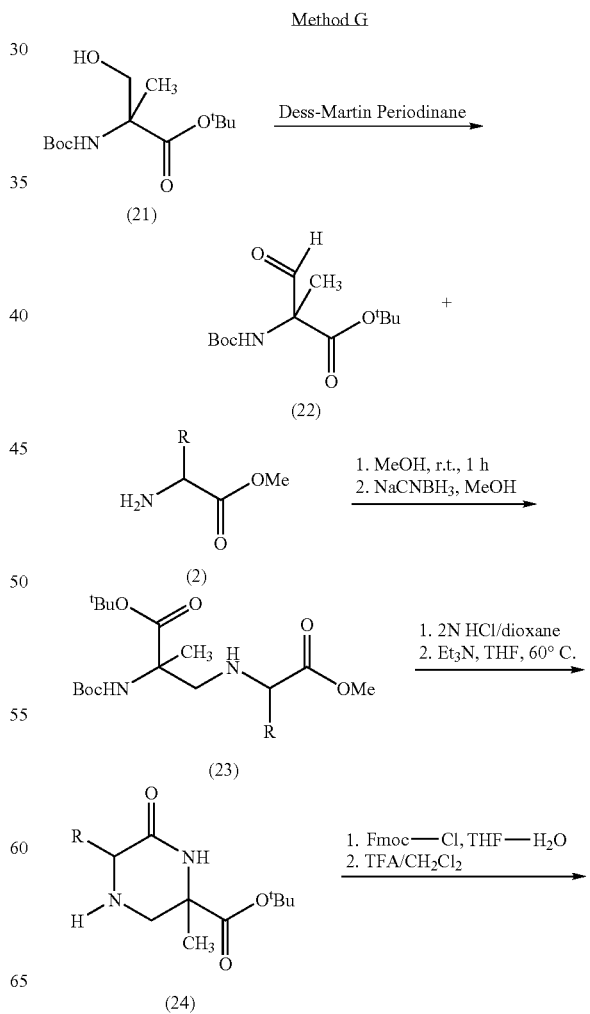

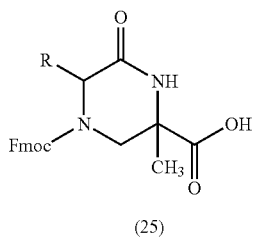

(25)

| R | Analytical Data for Compounds (25) |
|---|---|
| 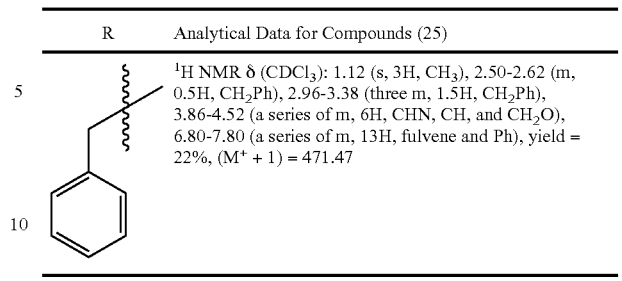 | $^1$H NMR δ (CDCl$_3$): 1.12 (s, 3H, CH$_3$), 2.50-2.62 (m, 0.5H, CH$_2$Ph), 2.96-3.38 (three m, 1.5H, CH$_2$Ph), 3.86-4.52 (a series of m, 6H, CHN, CH, and CH$_2$O), 6.80-7.80 (a series of m, 13H, fulvene and Ph), yield = 22%, (M$^+$ + 1) = 471.47 |

Synthesis of 2-Boc-amino-2-methyl-3-oxo-propionic acid tert-butyl ester (22): Oxidation of Boc α-Methyl serine tert-butyl ester (21) was done using Dess-Martin periodinane as describe before gave the desired product (22) in 96% crude yield. The compound was used without further purification in the next step. $^1$H NMR δ (CDCl$_3$): 1.44 (s, 18H, $^t$Bu), 1.46 (s, 3H, CH$_3$), 5.63-5.70 (br. s, 1H, NH), 9.5 (s, 1H, CHO)

Synthesis of 2-Boc-amino-3-(methoxycarbonyl-1-substituted-methylamino-2-methyl-propionic acid tert-butyl ester (23): Compounds (23) were prepared using a procedure similar to the one described for compound (10), but using compound (22) as the aldehyde. Compounds (23) were purified by silica gel column chromatography.

| R | Analytical Data for Compounds (23) |
|---|---|
| 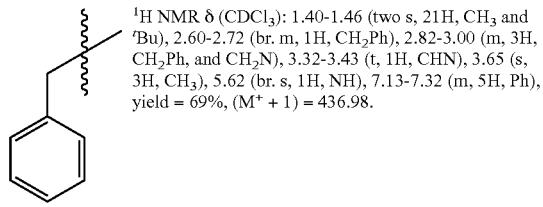 | $^1$H NMR δ (CDCl$_3$): 1.40-1.46 (two s, 21H, CH$_3$ and $^t$Bu), 2.60-2.72 (br. m, 1H, CH$_2$Ph), 2.82-3.00 (m, 3H, CH$_2$Ph, and CH$_2$N), 3.32-3.43 (t, 1H, CHN), 3.65 (s, 3H, CH$_3$), 5.62 (br. s, 1H, NH), 7.13-7.32 (m, 5H, Ph), yield = 69%, (M$^+$ + 1) = 436.98. |

Synthesis of 2-methyl-6-oxo-5-substituted-piperazine-2-carboxylic acid (25): A solution of 4 mmol of (23) in 8 mL of 2N hydrogen chloride in dioxane was stirred at room temperature for 5 hours, and then concentrated to dryness. The residue was suspended in 20 mL of tetrahydrofuran, neutralized with 10 mmol of triethylamine, and stirred at 60° C. for 2 days. It was then concentrated to dryness, resuspended in 20 mL of tetrahydrofuran and 10 mL of water, solid sodium bicarbonate was added to adjust the pH to basic, followed by 5.6 mmol of solid Fmoc chloride, and the reaction mixture stirred overnight at room temperature, the pH adjusted to 1 with 1N hydrochloric acid solution, diluted with 100 mL of ethyl acetate, and the layers separated. The organic layer was washed with 2×100 mL of brine, dried over magnesium sulfate and concentrated. The residue was dissolved in 10 mL of 50% trifluoroacetic acid in dichloromethane, and the solution stirred at room temperature for 3 hours. The solvent was concentrated, and the products (25) purified by silica gel column chromatography.

Synthesis of 2,2-disubstituted Ketopiperazine Scaffolds Mimicking Amino Acids with Functionalized Side Chains Method H The syntheses of 4-Fmoc-5-substituted-6-oxo-piperazine-2-methyl-2-carboxylic acid scaffolds mimicking amino acids with functionalized side chains are performed using method H. 2-Alloc-amino-3-(methoxycarbonyl-1-substituted-methylamino-2-methyl-propionic acid methyl ester (30) is prepared by reductive amination of 2-Alloc-amino-2-methyl-3-oxo-propionic acid methyl ester (28) with an α-amino allyl ester (29), using either sodium cyanoborohydride or sodium triacetoxyborohydride as the reducing agent, followed by protection of the secondary amine with benzylchloroformate. Compound (28) required for the reductive amination is obtained by oxidation of (27) with Dess-Martin periodinane. The allyl ester and the alloc groups of analogs (30) are removed using tetrakistriphenyl phosphine palladium (0) and the amino acid cyclized by reaction with a peptide coupling reagent to give 5-substituted-6-oxo-piperazine-2-methyl-2-carboxylic acid methyl esters (31). 4-Fmoc-5-substituted-6-oxo-piperazine-2-methyl-2-carboxylic acids (25) are obtained by saponification of the methyl ester, followed by protecting group exchange.

Method H

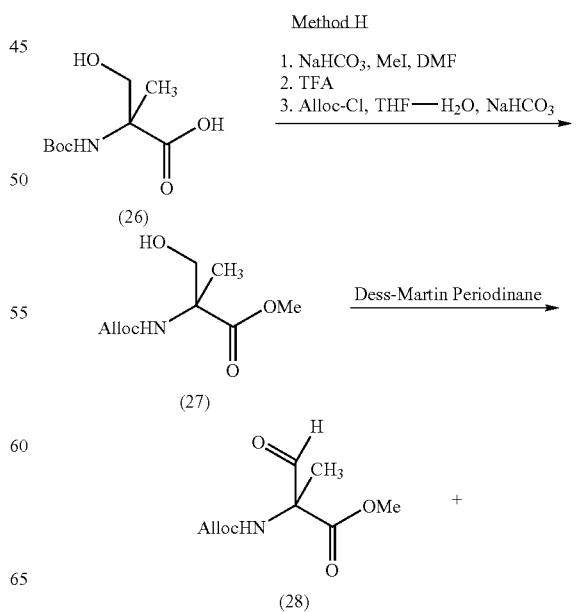

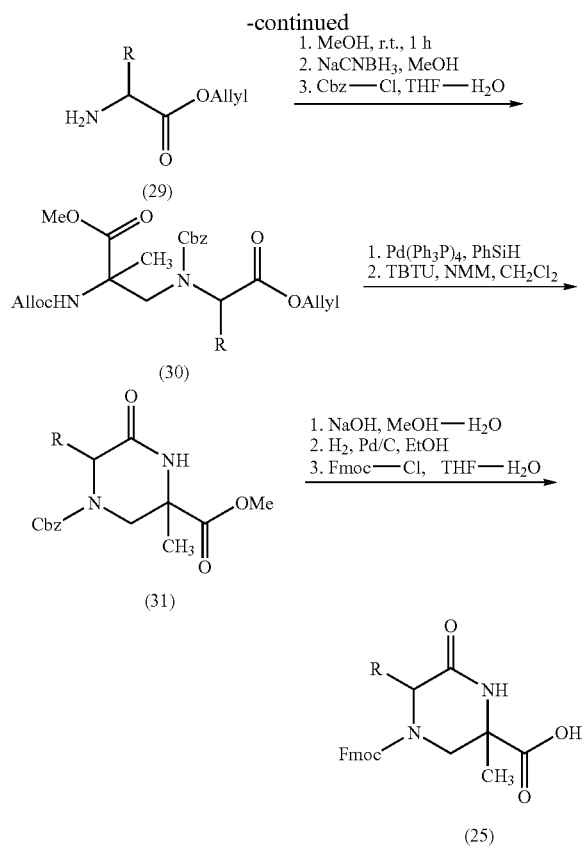

room temperature under nitrogen, is added 2 equivalents of phenylsilane and 0.3 equivalents of tetrakistriphenylphosphine palladium (0), and the solution stirred for 2 hours, and then 11 mmol of TBTU, and 14 mmol of N-methyl-morpholine are added, and the solution stirred at room temperature for 2 hours, and then concentrated to dryness.

Synthesis of 4-Fmoc-2-methyl-6-oxo-5-substituted-piperazine-2-carboxylic acid (25): To a solution of 10 mmol of compound (31) in 25 mL of methanol, kept at room temperature under nitrogen, is added slowly 11 mmol of 1N sodium hydroxide solution, and the reaction is stirred at room temperature overnight, neutralized with 21 mL of 1N hydrochloric acid solution, 1 g of 10% palladium on carbon is added, and the suspension hydrogenated at room temperature and atmospheric pressure for 3 hours. The suspension is filtered through celite and concentrated. The residue is redissolved in 25 mL of tetrahydrofuran, and 10 mL of water, followed by the addition of 30 mmol of solid sodium bicarbonate, and 10 mmol of Fmoc chloride, and the reaction is stirred at room temperature under nitrogen for 2 hours. The reaction is then diluted with 50 mL of ethyl acetate, and acidified with 1N hydrochloric acid solution. The layers are then separated, and the organic layer is washed with 1×20 mL of water, dried over magnesium sulfate, and concentrated. Compounds (25) are purified by silica gel column chromatography.

Synthesis of
(5-substituted-6-oxo-piperazin-2-yl)-acetic acid
Scaffolds

Methods I, J, K

The syntheses of (5-substituted-6-oxo-piperazin-2-yl)-acetic acid scaffolds were carried out by several methods.

Method I: (tert-butyl 3-protected-amino-4-(methoxycarbonyl-substituted-methylamino)-butyrates (35) were prepared by reductive amination of tert-butyl 3-protected-amino-4-oxo-butyrate (34) with α-amino esters (2), using either sodium cyanoborohydride or sodium triacetoxyborohydride as the reducing agent. The tert-butyl 3-protected-amino-4-oxo-butyrate (34) required for the reductive amination was prepared by lithium aluminum hydride (LAH) reduction of the Weinreb amide derivatives (33). Tert-butyl (3-protected-amino-4-(methoxycarbonyl-substituted-methylamino)-butyrate analogs (35) were then deprotected, cyclized, and Fmoc protected to give tert-butyl (5-substituted-6-oxo-piperazin-2-yl)-acetates (36), which were then deprotected to give the final products (37).

Synthesis of Alloc α-methyl serine methyl ester (27): A solution of 8 mmol of Boc (X-methyl serine (26), 1.0 g (12 mmol) of solid sodium bicarbonate, and 1.0 mL (16 mmol) of iodomethane in 8 mL of dry dimethylformamide, kept under nitrogen is stirred overnight. The reaction mixture is then poured over 50 mL of water, and extracted with 50 mL of diethyl ether, and washed with 1×20 mL of water, dried over magnesium sulfate, and concentrated. The residue is dissolved in 20 mL of 90% trifluoroacetic acid in dichloromethane, and the solution is stirred at room temperature for 3 hours, and then concentrated to dryness. The residue is dissolved in 35 mL of tetrahydrofuran, and 10 ml of water, followed by addition of 30 mmol of solid sodium bicarbonate, and the slow addition of 12 mmol of allyl chloroformate. The mixture is stirred at room temperature for 2 hours, diluted with 50 mL of ethyl acetate, and the layers separated. The organic layer is then washed with 1×10 mL of saturated sodium bicarbonate, and 1×10 ml of 1N hydrochloric acid, and 1×10 mL of water, dry over magnesium sulfate, and concentrated. Compound (27) is purified by silica gel column chromatography.

Synthesis of 2-Alloc-amino-2-methyl-3-oxo-propionic acid methyl ester (28): Oxidation of Alloc α-methyl serine methyl ester (27) is done using Dess-Martin periodinane as described above to yield the desired product (28).

Synthesis of 2-Alloc-amino-3-(methoxycarbonyl-1-substituted-methyl-Cbz-amino-2-methyl-propionic acid allyl ester (30): Compounds (30) are prepared using a procedure similar to the one described for compounds (15), but using compound (28) as the aldehyde.

Synthesis of 4-Cbz-2-methyl-6-oxo-5-substituted-piperazine-2-carboxylic acid methyl ester (31): To solution of 10 mmol of compound (30) in 30 mL of dichloromethane, kept at Method I

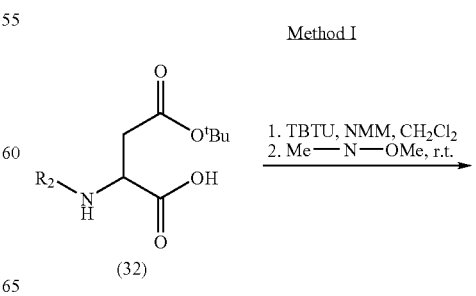

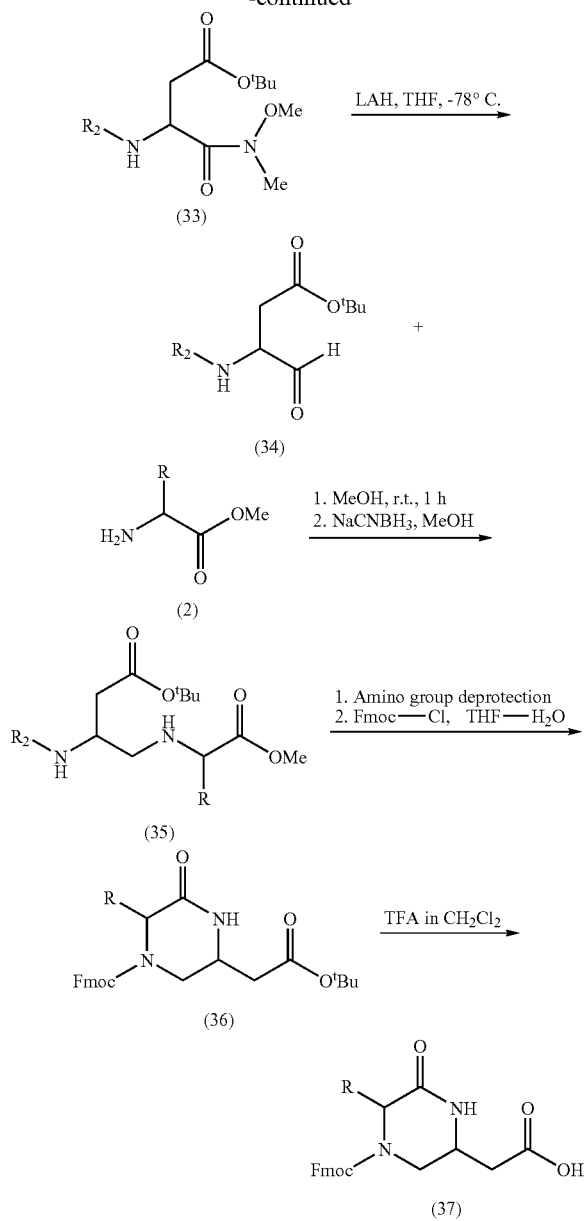

R₂ Analytical Data for Compounds (34)

Cbz ¹H NMR δ (CDCl₃): 1.40 (s, 9H, ᵗBu), 2.69-2.81 (dd, 1H, CH₂CO), 2.89-3.01 (dd, 1H, CH₂CO), 4.33-4.42 (m 1H, CHN), 5.12 (s, 2H, CH₂O), 5.83-5.88 (br. d, 1H, NH), 7.31-7.39 (br. m, 5H, Ph), 9.64 (s, 1H, CHO)

Fmoc ¹H NMR δ (CDCl₃): 1.45 (s, 9H, ᵗBu), 2.58-3.02 (a series of m, 2H, CH₂CO), 4.20-4.28 (t, 1H, CH), 4.35-4.49 (m, 3H, CH₂O, and CHN), 5.85-5.92 (br. d, 1H, NH), 7.27-7.80 (a series of m, 8H, fulvene), 9.65 (s, 1H, CHO)

Synthesis of tert-butyl 3-Protected-amino-4-(methoxycarbonyl-substituted-methylamino)-butyrate (35): Compounds (35) were prepared using a procedure similar to the one described for compounds (10), but using compounds (34) as the aldehyde.

| R₂ | R | Analytical Data for Compounds (35) |
|---|---|---|
| Cbz | 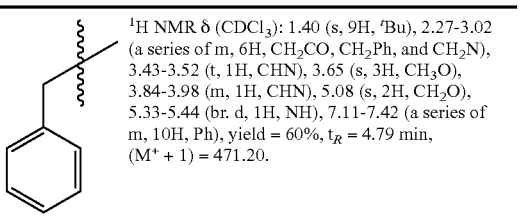 | ¹H NMR δ (CDCl₃): 1.40 (s, 9H, ᵗBu), 2.27-3.02 (a series of m, 6H, CH₂CO, CH₂Ph, and CH₂N), 3.43-3.52 (t, 1H, CHN), 3.65 (s, 3H, CH₃O), 3.84-3.98 (m, 1H, CHN), 5.08 (s, 2H, CH₂O), 5.33-5.44 (br. d, 1H, NH), 7.11-7.42 (a series of m, 10H, Ph), yield = 60%, t_R = 4.79 min, (M⁺ + 1) = 471.20. |
| Cbz | 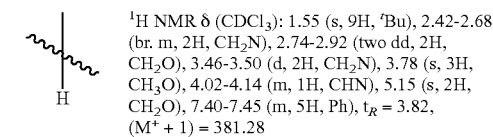 | ¹H NMR δ (CDCl₃): 1.55 (s, 9H, ᵗBu), 2.42-2.68 (br. m, 2H, CH₂N), 2.74-2.92 (two dd, 2H, CH₂O), 3.46-3.50 (d, 2H, CH₂N), 3.78 (s, 3H, CH₃O), 4.02-4.14 (m, 1H, CHN), 5.15 (s, 2H, CH₂O), 7.40-7.45 (m, 5H, Ph), t_R = 3.82, (M⁺ + 1) = 381.28 |
| Cbz | 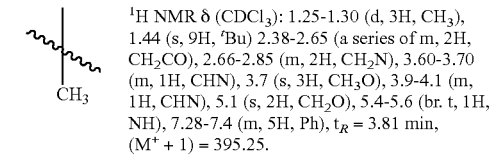 | ¹H NMR δ (CDCl₃): 1.25-1.30 (d, 3H, CH₃), 1.44 (s, 9H, ᵗBu) 2.38-2.65 (a series of m, 2H, CH₂CO), 2.66-2.85 (m, 2H, CH₂N), 3.60-3.70 (m, 1H, CHN), 3.7 (s, 3H, CH₃O), 3.9-4.1 (m, 1H, CHN), 5.1 (s, 2H, CH₂O), 5.4-5.6 (br. t, 1H, NH), 7.28-7.4 (m, 5H, Ph), t_R = 3.81 min, (M⁺ + 1) = 395.25. |
| Cbz | 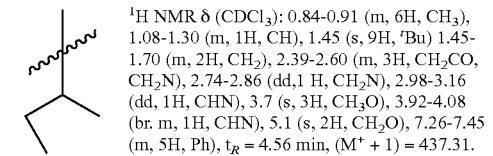 | ¹H NMR δ (CDCl₃): 0.84-0.91 (m, 6H, CH₃), 1.08-1.30 (m, 1H, CH), 1.45 (s, 9H, ᵗBu) 1.45-1.70 (m, 2H, CH₂), 2.39-2.60 (m, 3H, CH₂CO, CH₂N), 2.74-2.86 (dd,1 H, CH₂N), 2.98-3.16 (dd, 1H, CHN), 3.7 (s, 3H, CH₃O), 3.92-4.08 (br. m, 1H, CHN), 5.1 (s, 2H, CH₂O), 7.26-7.45 (m, 5H, Ph), t_R = 4.56 min, (M⁺ + 1) = 437.31. |

Synthesis of tert-butyl (4-Fmoc-5-substituted-6-oxo-piperazin-2-yl)-acetate (36): For compounds containing Fmoc amino protecting group, a solution of 10 mmol of compound (35) in 30 mL of 30% diethyl amine in ethyl acetate solution was stirred at room temperature overnight, and then concentrated to dryness. For compounds containing Cbz amino protecting group, a solution of 10 mmol of compound (35) in 30 mL of ethanol was hydrogenated at room temperature and atmospheric pressure for 2 hours, filtered through celite, and concentrated to dryness. For Fmoc protection, the residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours and diluted with ethyl acetate. The layers separated, and the organic layer was washed with water, dried over magnesium sulfate, and concentrated. Compounds (36) were purified by silica gel column chromatography.

Synthesis of amino protected Asp-(OᵗBu) Weinreb amide (33): Compounds (33) were prepared using a procedure similar to the one described for compound (14).

R₂ Analytical Data for Compounds (33)

Cbz ¹H NMR δ (CDCl₃): 1.40 (s, 9H, ᵗBu), 2.47-2.59 (dd, 1H, CH₂CO), 3.20 (s, 3H, CH₂N), 3.77 (s, 3H, CH₃O), 4.96-5.05 (br. m, 1H, CHN), 5.05-5.12 (br. d, 2H, CH₂O), 5.58-5.66 (br. d, 1H, NH), 7.30-7.36 (br. m, 5H, Ph), yield = 90%

Fmoc ¹H NMR δ (CDCl₃): 1.45 (s, 9H, ᵗBu), 2.55-2.64 (dd, 1H, CH₂CO), 2.69-2.80 (dd, 1H, CH₂O), 3.60 (s, 3H, CH₃N), 3.79 (s, 3H, CH₃O), 4.18-4.26 (t, 1H, CH), 4.32-4.40 (d, 2H, CH₂O), 4.98-5.19 (m, 1H, CHN), 5.70-5.76 (br. d, 1H, NH), 7.35-7.80 (a series of m, 8H, fulvene), yield = quant.

Synthesis of tert-butyl 3-amino protected-amino-4-oxo-butyrate (34): Compounds (34) were prepared using a procedure similar to the one described for compound (9).

| R | Analytical Data for Compounds (36) |
|---|---|
| benzyl | $^1$H NMR δ (CDCl$_3$): 1.44 (s, 9H, $^t$Bu), 1.71-2.10 (m, 2H, CH$_2$CO), 2.10-2.30 (br. d, 1H, CHN), 2.62-2.82 (br. d, 1H, CH$_2$Ph), 2.90-3.74 (a series of br. m, 3H, CH$_2$N, CHN), 3.80-4.07 (br. d, 1H, CHN), 4.10-4.50 (br. m, 3H, CH$_2$O, and CH), 6.74-7.80 (a series of m, 23H, fulvene, and Ph), yield = 75%, $t_R$ = 7.15 min, (M$^+$ + 1) = 527.20. |
| isobutyl | $^1$H NMR δ (CDCl$_3$): 0.77-1.94 (a series of m, and two s, 18H, $^t$Bu, CH$_2$, and CH$_3$), 2.07-2.76 (three m, 3H, CH$_2$CO, and CHN), 2.86-3.80 (four m, 2H, CH$_2$N), 4.16-4.27 (m, 1H, CH), 4.30-4.43 (m, 1H, CHN), 4.50-4.70 (br. m, 2H, CH$_2$O), 7.26-7.79 (a series of m, 8H, fulvene), yield = 40% for three steps, $t_R$ = 7.31 min, (M$^+$ + 1) = 493.47. |
| H | $^1$H NMR δ (CDCl$_3$): 1.45 (s, 9H, $^t$Bu), 1.9-2.5 (m 2H, CH$_2$CO), 3.02-4.7 (a series of m, 8H, CH, CH$_2$, CH$_2$N), 7.25-7.78 (three m, 8H, fulvene), $t_R$ = 6.42 min, (M$^+$ + 1) = 431.31. |
| CH$_3$ | $^1$H NMR δ (CDCl$_3$): 1.20-1.35 (br. m, 3H, CH$_3$), 1.45 (s, 9H, $^t$Bu) 2.1-2.80 (three m, 3H, CH$_2$CO, CH$_2$N), 3.1-4.1 (four m, 3H, CH$_2$N, CHN), 4.18-4.26 (br. t, 1H, CH), 4.28-4.46 (br. m, 1H, CHN), 4.50-4.68 (br. m, 2H, CH$_2$), 7.28-7.8 (three m, 8H, fulvene), $t_R$ = 6.29 min, (M$^+$ + 1) = 451.24. |
| sec-butyl | $^1$H NMR δ (CDCl$_3$): 1.20-1.60 (br. m, and s, 15H, CH$_3$, $^t$Bu) 2.21-2.80 (3 br. m, 2H, CH$_2$CO), 3.0-3.9 (four br. m, 2H, CH$_2$N), 4.18-4.26 (br. m, 2H, CH, CHN), 4.38-4.86 (br. m, 3H, CH$_2$, CHN), 7.26-7.86 (a series of m, 8H, fulvene), $t_R$ = 6.90 min, (M$^+$ + 1) = 493.31. |

Synthesis of (4-Fmoc-5-substituted-6-oxo-piperazin-2-yl)-acetate (37): Compounds (36) were deprotected with 90% trifluoroacetic acid solution in dichloromethane for 3 hours, and then concentrated to dryness. Final products (37) were purified by silica gel column chromatography.

| R | Analytical Data for Compounds (37) |
|---|---|
| benzyl | $^1$H NMR δ(CDCl$_3$): 1.82-2.13(br. t, 1H, CHN), 2.32-2.53(br. d, 1H, CH$_2$CO). 2.63-2.81(br. d, 1H, CH$_2$CO), 2.90-3.29(two br. m, CH$_2$Ph), 3.38-3.59(br. m, 1H, CH$_2$N), 3.66-3.85(br. m, 1H, CH$_2$N), 3.95-4.24(two overlapping br. peaks, 2H, CHN, CH), 4.30-4.93(br. d, 2H, CH$_2$O), 6.84-7.82(a series of m, 13H, fulvene, and Ph), 8.08-8.25(br. d,1H, CO$_2$H), yield = quant., $t_R$ = 5.57 min, (M$^+$ + 1) = 471.07. |
| isobutyl | $^1$H NMR δ(CDCl$_3$): 0.72-1.92(five br. m, 9H, CH$_2$, and CH$_3$), 2.14-2.70(two br. m, 3H, CH$_2$CO, and CHN), 3.26-3.62(two br. m, 1H, CH$_2$N), 3.70-3.90(br. m, 1H, CH$_2$N), 4.03-4.30(two m, 2H, CHN, and OH), 4.42-4.82(br. m, 2H, CH$_2$O), 7.28-7.82(a series of m, 8H, fulvene), 7.97(s, 1H, CO$_2$H), yield = 90%, $t_R$ = 5.61 min,(M$^+$ + 1) = 437.76. |

| R | Analytical Data for Compounds (37) |
|---|---|
| H | $^1$H NMR δ(CDCl$_3$): 2.10-2.66(m, 2H, CH$_2$CO), 3.2-3.92(four m, 3H, CH$_2$N, CHN), 3.97-4.06(m, 1H, CH), 4.2-4.3(m, 2H, CH$_2$), 4.48-4.62(m, 2H, CH$_2$N), 7.24-7.81(a series of m, 8H, fulvene), $t_R$ = 4.74 min, (M$^+$ + 1) = 381.13. |
| CH$_3$ | $^1$H NMR δ(CDCl$_3$): 1.15-1.37(br. m, 3H, CH$_3$), 2.22-2.78(three br. m, 2H, CH$_2$CO), 3.0-4.10(five br. m, 3H, CH$_2$N, CHN), 4.15-4.40(m, 1H, CH), 4.45-4.7 (br. m, 3H, CH$_2$, CHN), 7.26-8.10(a series of m, 8H, fulvene), $t_R$ = 4.66 min, (M$^+$ + 1) = 395.32. |
| sec-butyl | $^1$H NMR δ(CDCl$_3$): 0.6-1.2(m, 6H, CH$_3$), 1.22-2.8(four m, 4H, CH$_2$CO, CH$_2$), 3.1-4.0(five m, 3H, CH$_2$N, CHN), 4.18-4.32(m, 1H, CH), 4.41-4.84(m, 3H, CH$_2$, CHN), 7.26-8.2(a series of m, 8H, fulvene), $t_R$ = 5.46 min, (M$^+$ + 1) = 437.37. |

Method J: Diphenylmethyl 3-Fmoc-amino-4-(methoxy-carbonyl-substituted-methylamino)-butyrates (41) were prepared by reductive amination of diphenylmethyl 3-Fmoc-amino-4-oxo-butyrate (40) with α-amino esters (2), using either sodium cyanoborohydride or sodium triacetoxyborohydride as the reducing agent. The diphenylmethyl 3-Fmoc-amino-4-oxo-butyrate (40) required for the reductive amination was prepared by lithium aluminum hydride reduction of the Weinreb amide derivative (39), which was formed from commercially available Fmoc-aspartic acid α-allyl ester derivative (38) by protection of the β-ester under Mitsunobu conditions. The allyl ester was removed using palladium (0) catalyst, followed by Weinreb amide formation using TBTU as the coupling agent. Diphenylmethyl 3-Fmoc-amino-4-(methoxycarbonyl-substituted-methylamino)-butyrate (41) was then Fmoc deprotected, cyclized, diphenylmethyl ester removed by hydrogenation, followed by Fmoc protection to give the final product (4-Fmoc-5-substituted-6-oxo-piperazin-2-yl)-acetic acid (37).

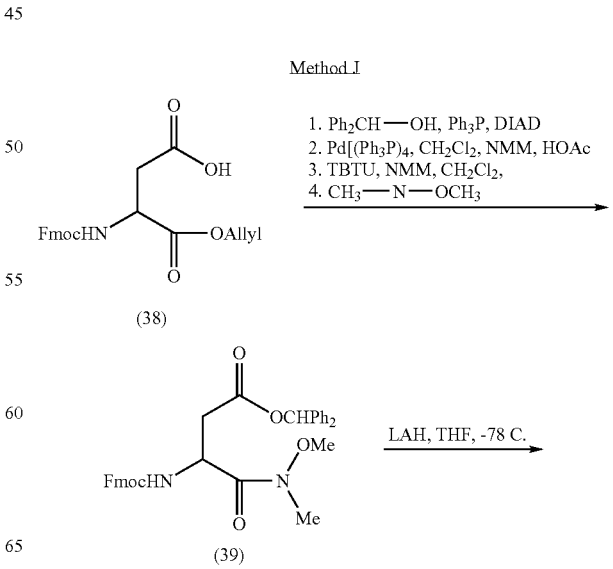

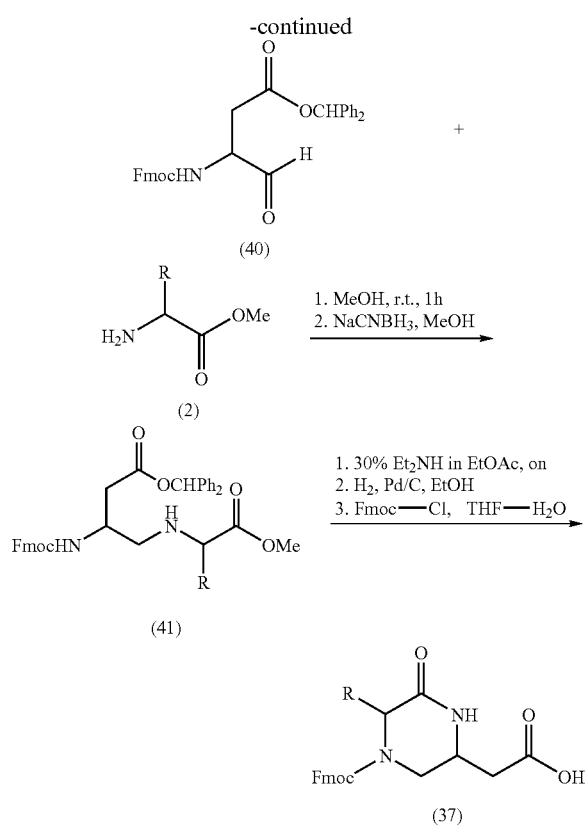

Synthesis of Fmoc-Asp-(OCHPh₂) Weinreb amide (39): To a solution of 5.1 g (13.0 mmol) of Fmoc-aspartic acid α-allyl ester (38) in 30 mL of dry tetrahydrofuran, containing 3.4 g (13 mmol) of triphenylphosphine, and 2.41 g (13.1 mmol) of diphenylmethanol, kept at 0° C. under nitrogen, was added slowly 2.6 mL (13.4 mmol) of diisopropyl azodicarboxylate. The ice bath was removed, and the reaction stirred at room temperature overnight, concentrated to dryness, and then purified by silica gel column chromatography. ¹H NMR δ (CDCl₃) 2.96-3.06 (dd, 1H, CH₂CO), 3.15-3.26 (dd, 1H, CH₂CO), 4.18-4.76 (a series of m, 3H, CH, CH₂), 5.14-5.32 (m, 1H, CHN), 5.76-5.86 (m, 1H, CHO), 7.20-7.80 (a series of m, 18H, fulvene, and Ph); HPLC t$_R$=7.68 min, (M⁺+Na⁺)=583.90.

The product (9.8 mmol) was then dissolved in 40 mL of a dichloromethane:acetic acid:N-methyl morpholine solution at 37:2:1, containing 1.5 g (1.3 mmol) of tetrakis triphenylphosphine palladium (0), and the solution stirred at room temperature overnight, concentrated to dryness, and partitioned between 100 mL of ethyl acetate and 30 mL of water. The layers were separated, and the organic layer washed with 1×50 mL of water, dried over sodium sulfate, and concentrated. The residue was suspended in 20 mL of dry dichloromethane, and 1.65 mL (15 mmol) of N-methyl morpholine, and 4.07 g (12.7 mmol) of TBTU were added, and the suspension stirred at room temperature for 20 minutes, followed by the addition of 1.65 mL (15 mmol) of N-methyl morpholine, and 1.52 g (15.6 mmol) of N,O-dimethyl hydroxylamine hydrochloride salt. The suspension was stirred at room temperature for 2 hours, concentrated, partitioned between 100 mL of ethyl acetate and 50 mL of water. The organic layer was washed with 1×30 mL of water, 1×30 mL of saturated sodium bicarbonate solution, and 1×30 mL of 1N hydrochloric acid solution, dried over sodium sulfate, and concentrated. The product was purified by silica gel column chromatography. ¹H NMR δ (CDCl₃) 2.76-2.88 (dd, 1H, CH₂CO), 2.89-3.00 (dd, 1H, CH₂CO), 3.16 (s, 3H, CH₃N), 3.70 (s, 3H, CH₃O), 4.14-4.22 (dd, 1H, CH), 4.28-4.40 (t, 2H, CH₂), 5.07-5.16 (dd, 1H, CHN), 5.69-5.76 (d, 1H, CHO), 7.24-7.8 (a series of m, 18H, fulvene, and Ph); HPLC t$_R$=7.08, (M⁺+Na⁺)=587.03.

Synthesis of Diphenylmethyl 3-Fmoc-amino-4-oxo-butyrate (40): Compound (40) is prepared using a procedure similar to the one described for compound (9).

Synthesis of Diphenylmethyl 3-Fmoc-amino-4-(methoxycarbonyl-substituted-methylamino)-butyrate (41): Compounds (41) were prepared using a procedure similar to the one described for compound (10), but using compound (40) as the aldehyde.

| R | Analytical Data for Compounds (41) |
|---|---|
| ![R group with NHPbf and guanidine] HN–C(=NH)–NHPbf | ¹H NMR δ(CDCl₃) 1.2-1.7(m, 4H, CH₂), 1.42(s, 3H, CH₃Ph), 1.60(s, 6H, CH₃—Ph), 2.07(s, 2H, CH₂), 2.52(s, 3H, CH₃—Ph), 2.58(s, 3H, CH₃—Ph), 2.08-2.80(a series of m, 2H, CH₂CO), 3.0-3.2(m, 2H, CH₂N), 3.64(s, 3H, CH₃O), 3.96-4.10(m, 1H, CHN), 4.20-4.28(m, 1H, CH), 4.28-4.40(br. m, 2H, CH₂),5.82-6.18(m, 1H, CHO), 7.24-7.80(a series of m, 18H, fulvene, and Ph), HPLC t$_R$ = 6.53, (M⁺ + 1) = 930.56. |

Synthesis of (4-Fmoc-5-substituted-6-oxo-piperazin-2-yl)-acetic acid (37): A solution of 10 mmol of compound (41) in 30 mL of 30% diethylamine in ethyl acetate was stirred at room temperature for 3 hours. The solution was then concentrated to dryness, redissolved in 2×30 mL of ethyl acetate, and reconcentrated. The residue dissolved in 50 mL of ethanol, and 20 mL of 1N hydrochloric acid solution, and hydrogenated at room temperature and atmospheric pressure overnight, filtered through celite, and concentrated to dryness. The residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours, diluted with 100 mL of ethyl acetate, the layers separated, and the organic layer washed with 2×50 mL of water, dried over magnesium sulfate, and concentrated. The product was purified by silica gel column chromatography.

| R | Analytical Data for Compounds (37) |
|---|---|
| HN–C(=NH)–NHPbf | ¹H NMR δ(CDCl₃) 1.2-1.6(m, and s, 7H, CH₂, CH₃Ph), 2.10(s, 2H, CH₂), 2.46(s, 3H, CH₃—Ph), 2.56(s, 3H, CH₃—Ph), 2.46-2.63(br. m, 2H, CH₂CO), 3.0-3.95(3 br. m, 5H, CH₂N, CHN), 4.10-4.30(br. m, 1H, CH), 4.40-4.80(br. m, 3H, CHN, CH₂), 7.22-7.80(a series of m, 8H, fulvene), HPLC t$_R$ = 5.73, (M⁺ + 1)732.24. |

Method K: The syntheses of (5-substituted-6-oxo-piperazin-2-yl)-acetic acid scaffolds are done starting from commercially available Fmoc-Aspartic acid α tert-butyl ester (42). Fmoc-aspartic acid α tert-butyl ester is reduced to Fmoc-Homoserine α tert-butyl ester with sodium borohydride via the mixed anhydride, followed by protection of the alcohol with benzyl bromide to give Fmoc-Homoserine benzyl ether α tert-butyl ester (43). The tert-butyl ester is then removed with trifluoroacetic acid, and the acid is reduced to the alcohol with sodium borohydride via the mixed anhydride to give 2-Fmoc-amino-4-benzyloxy-1-butanol (44). Alcohol (44) is then converted to 2-Fmoc-amino-4-benzyloxybutanal (45) using Dess-Martin periodinane as described previously. Reductive amination of 2-Fmoc-amino-4-benzyloxybutanal (45) and α-amino ester (2) gives the (2-Fmoc-amino-4-benzyloxy-butylamino)-2-substituted acetic acid methyl ester (46). Fmoc deprotection with diethyl amine gives the free primary amine which cyclizes to 6-benzyloxyethyl-3-substituted-piperazin-2-one spontaneously. The benzyl ether is removed by hydrogenation, and the secondary amine is protected as its Fmoc derivative to give 4-Fmoc-6-hydroxymethyl-3-substituted-piperazin-2-ones (47). Finally, the primary alcohol is oxidized to the acid to give the final products (48) as described in method A.

and then quenched with 1N hydrochloric acid solution. The reaction mixture is diluted with 100 mL of ethyl acetate, and the layers separated. The organic layer was washed with 2×25 mL of 1N hydrochloric acid solution, 2×25 mL of water, dried over magnesium sulfate and concentrated, and purified by silica gel column chromatography. Purified compound is then dissolved in 30 mL of tetrahydrofuran, and 12 mmol of 60% sodium hydride dispersion in mineral oil is added, followed by 0.2 mmol of tetrabutylammonium iodide and 12 mmol of benzyl bromide, and the mixture is stirred overnight, quenched with 50 mL of saturated aqueous sodium bicarbonate, and extracted with 100 mL of ethyl acetate. The compound is then purified by silica gel column chromatography.

Synthesis of 2-Fmoc-amino-4-benzyloxy-1-butanol (44): Deprotection of the tert-butyl ester using 90% trifluoroacetic acid is done as described for compound (37) in method I, followed by reduction of the acid to the alcohol with sodium borohydride via the mixed anhydride intermediate as described for compound (13).

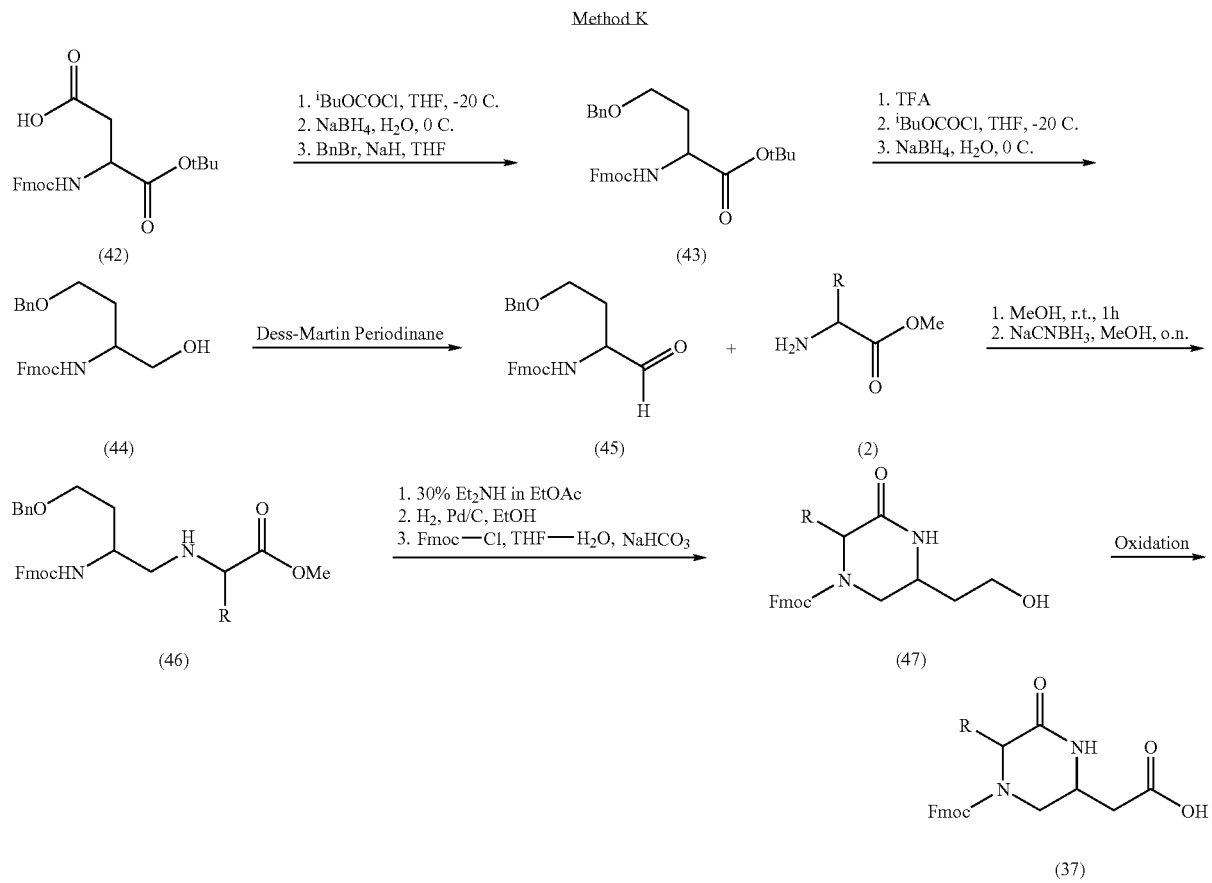

Method K

Synthesis of Fmoc-Homoserine (OBn) α tert-butyl ester (43): To a solution of 10.0 mmol of Fmoc Asp-O$^t$Bu (42) in 50 mL of dry tetrahydrofuran, kept at −20° C. under nitrogen, is added 1.77 mL (12.7 mmol) of triethyl amine, followed by the slow addition of 1.57 mL (12.0 mmol) of isobutylchloroformate. The mixture is stirred for 30 minutes, and then poured slowly over an ice-cold solution of 3.77 g (99.6 m mol) of sodium borohydride in 10 mL of water, keeping the temperature below 5° C. The reaction is stirred at 0° C. for 15 minutes, Synthesis of 2-Fmoc-amino-4-benzyloxy-butanal (45): 2-Fmoc-amino-4-benzyloxy-1-butanol (44) is oxidized to the aldehyde using Dess-Martin periodinane as described for the synthesis of (9).

Synthesis of (2-Fmoc-amino-4-benzyloxy-butylamino)-2-substituted acetic acid methyl ester (46): reductive amination of 2-Fmoc-amino-4-benzyloxy-butanal (45) with an α-amino ester (2) using either sodium cyanoborohydride or sodium triacetoxyborohydride as the reducing agent is done as described for the synthesis of (10).

Synthesis of 4-Fmoc-6-hydroxymethyl-3-substituted-piperazin-2-ones (47): Fmoc deprotection of (2-Fmoc-amino-4-benzyloxy-butylamino)-2-substituted acetic acid methyl ester (46) with concomitant cyclization, followed by de-benzylation and Fmoc reprotection is done as described for compound (37) in method J.

Synthesis of 4-Fmoc-5-substituted-6-oxo-piperazin-2-yl-acetic acid (37): Oxidation of 4-Fmoc-6-hydroxymethyl-3-substituted-piperazin-2-ones (47) to the acid is done as described in method A. The choice of the oxidizing agent used is based on the nature of the group in the 5-position.

Synthesis of 2-Substituted 3-Oxo-[1,4]-diazepane-5-carboxylic acid Scaffolds

Methods L, M, N

The synthesis of 2-substituted 3-oxo-[1,4]-diazepane-5-carboxylic acid scaffolds is done using several methods.

Method L: tert-butyl 2-Cbz-amino-4-(benzyloxycarbonyl-substituted-methyl-Boc amino)-butyrates (52) are prepared by reductive amination of tert-butyl Cbz-2-amino-4-oxo-butyrate (50) with amino ester (51), using either sodium cyanoborohydride or sodium triacetoxyborohydride as the reducing agent, followed by Boc protection of the secondary amine. The tert-butyl Cbz-2-amino-4-oxo-butyrate (50) required for the reductive amination is prepared by lithium aluminum hydride reduction of the Weinreb amide derivative (49). The diazepane ring is formed by protecting group removal, followed by cyclization with a peptide forming reagent to give (53). Finally, 4-Fmoc-2-substituted 3-oxo-[1,4]-diazepane-5-carboxylic acids (54) are formed by protecting group exchange.

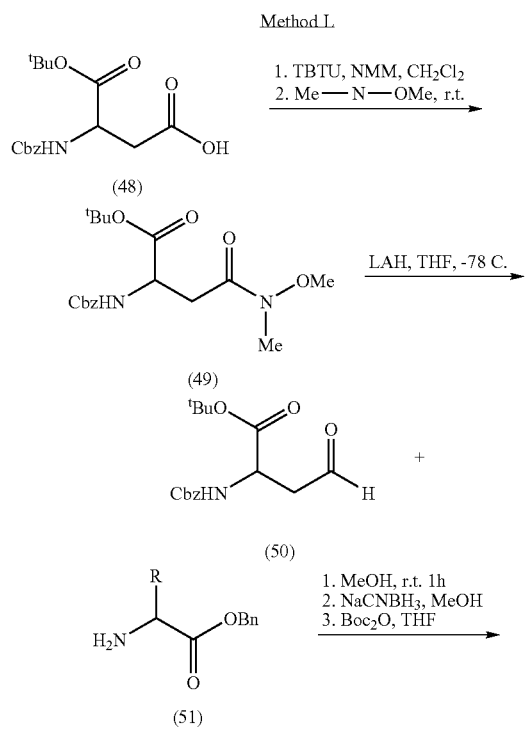

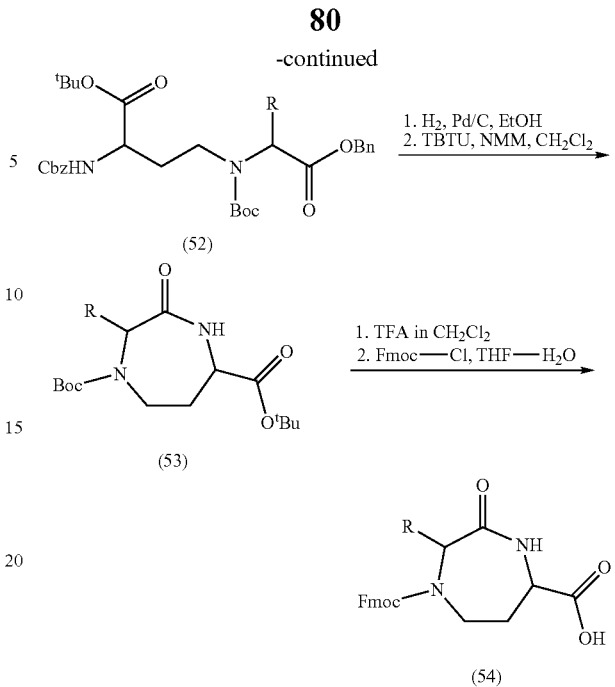

Synthesis of Cbz-Asp-(Weinreb amide)-O$^t$Bu (49): Compound (49) is prepared using a procedure similar to the one described for compound (14).

Synthesis of tert-butyl 3-Cbz-amino-4-oxo-butyrate (50): Compound (50) is prepared using a procedure similar to the one described for compound (9).

Synthesis of tert-butyl 2-Cbz-amino-4-(benzyloxycarbonyl-substituted-methyamino)-butyrate (52): The reductive amination is done with procedure similar to the one described for compound (10). The secondary amine is protected by reaction of the crude mixture with 2 equivalents of Boc dicarbonate in tetrahydrofuran.

Synthesis of tert-butyl 1-Boc 2-substituted-3-oxo-[1,4]-diazepane-5-carboxylate (53): A solution of 10 mmol of compound (52) in 30 mL of ethanol is hydrogenated at room temperature and atmospheric pressure for 2 hours, filter through celite, and concentrated to dryness. The residue is dissolved in 100 mL of dichloromethane and 1.2 equivalents of TBTU, and 2.6 equivalents of N-methyl-morpholine are added. The solution is stirred at room temperature overnight, and then concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (53) in 10 mL of 90% trifluoroacetic acid in dichloromethane is stirred at room temperature for 2 hours, and then the solution is concentrated to dryness. The residue is dissolved in 20 mL of tetrahydrofuran and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with 2×50 mL of water, dried over magnesium sulfate, and concentrated.

Method M: the reduced dipeptide analogs (60) are prepared by reductive amination of diphenylmethyl Alloc-2-amino-4-oxo-butyrate (59) with amino ester (29), using either sodium cyanoborohydride or sodium triacetoxyborohydride as the reducing agent, followed by Cbz protection of the secondary amine. Diphenylmethyl Alloc-2-amino-4-oxo-butyrate (59) required for the reductive amination is prepared by lithium aluminum hydride reduction of the Weinreb amide derivative (58), which is prepared by protecting group exchange of Weinreb amide derivative (57). The diazepane ring is then formed by allyl and alloc group removal, followed by ring closure in the presence of a peptide forming reagent. 2-substituted 3-oxo-[1,4]-diazepane-5-carboxylic acid scaffolds (54) are formed by protecting group exchange.

Synthesis of diphenylmethyl 3-Alloc-amino-4-oxo-butyrate (59): Compound (59) is prepared using a procedure similar to the one described for compound (9).

Synthesis of diphenyl methyl 2-Alloc-amino-4-(allyloxy-carbonyl-substituted-methyamino)-butyrate (60): compound 60 is prepared by reductive amination using a procedure similar to the one described for compounds (15), but using compound (59) as the aldehyde. The product is purified by silica gel column chromatography.

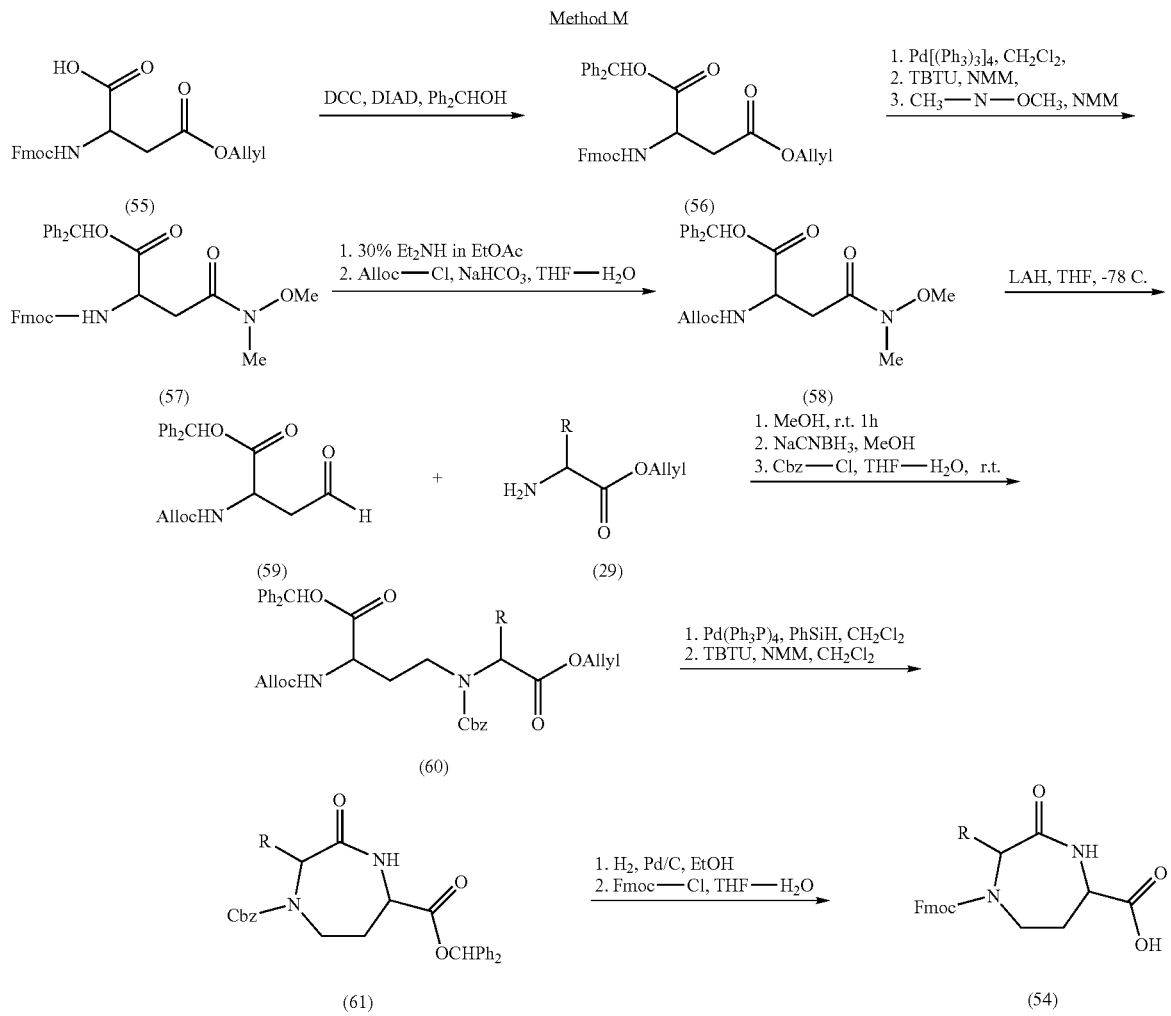

Synthesis of Fmoc-Asp-(Weinreb amide)-OCHPh₂ (57): Compound (57) is prepared using a procedure similar to the one described for compound (39).

Synthesis of Alloc-Asp-(Weinreb amide)-OCHPh₂ (58): A solution of 10 mmol of compound (56) in 20 mL of 30% diethylamine in ethyl acetate is stirred for 2 hours, and concentrated to dryness. The residue is dissolved in 20 mL of tetrahydrofuran and 10 mL of water, and 2.52 g (30 mmol) of solid sodium bicarbonate is added, followed by the addition of 13 mmol of Alloc-Cl. The mixture is stirred for 3 hours, and then diluted with ethyl acetate. The layers are separated, and the organic layer washed with water, dried over magnesium sulfate, and concentrated. Compound (58) is purified by silica gel column chromatography.

Synthesis of diphenylmethyl 1-Cbz 2-substituted-3-oxo-[1,4]-diazepane-5-carboxylate (61): To a solution of 10 mmol of compound (60) in 30 mL of dichloromethane, kept at room temperature under nitrogen, is added 2 equivalents of phenylsilane and 0.3 equivalents of tetrakistriphenylphosphine palladium (0), and the solution stirred for 2 hours, and then 1.2 equivalents of TBTU and 1.3 equivalents of N-methyl-morpholine are added. The solution is stirred at room temperature overnight and concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (61) in 30 mL of ethanol is hydrogenated at room temperature for 2 hours, filtered through celite, and then the solution is concentrated to dryness. The residue is dissolved in 20 mL of tetrahydrofuran, and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with water, dried over magnesium sulfate, and concentrated.

Method N: Fmoc-Aspartic acid β tert-butyl ester is reduced to Fmoc-Aspartanol β tert-butyl ester (63) with sodium borohydride via the mixed anhydride, followed by protection of the alcohol with allyl bromide to give Fmoc-Aspartanol allyl ether β tert-butyl ester (64). The tert-butyl ester is then removed with trifluoroacetic acid, and the acid reduced to the alcohol with sodium borohydride via the mixed anhydride to give 3-Fmoc-amino-4-allyloxy-1-butanol (65). Alcohol (65) is then converted to 3-Fmoc-amino-4-allyloxybutanal (66) using Dess-Martin periodinane as described previously. Reductive amination of 3-Fmoc-amino-4-allyloxybutanal (66) and α amino ester (51), followed by alloc protection on the secondary amine, gives the (3-Fmoc-amino-4-allyloxy-butyl-alloc-amino)-2-substituted acetic acid benzyl esters (67). Alloc 7-allyloxymethyl-3-substituted-[1,4]-diazepan-2-ones (68) are formed by saponification of the benzyl ester, followed by Fmoc deprotection with diethyl amine to give the free primary amine which is cyclized using a peptide forming reagent such as TBTU. The final products (54) are formed by protecting group exchange: the allyl ether and the alloc are removed by palladium (0), and the secondary amine is protected as its Fmoc derivative to give 4-Fmoc-7-benzyloxymethyl-3-substituted-[1,4]-diazepan-2-ones, followed by primary alcohol oxidation to the acid to give the final products (54). The choice of the oxidizing agent used is based on the nature of the group in the 2-position.

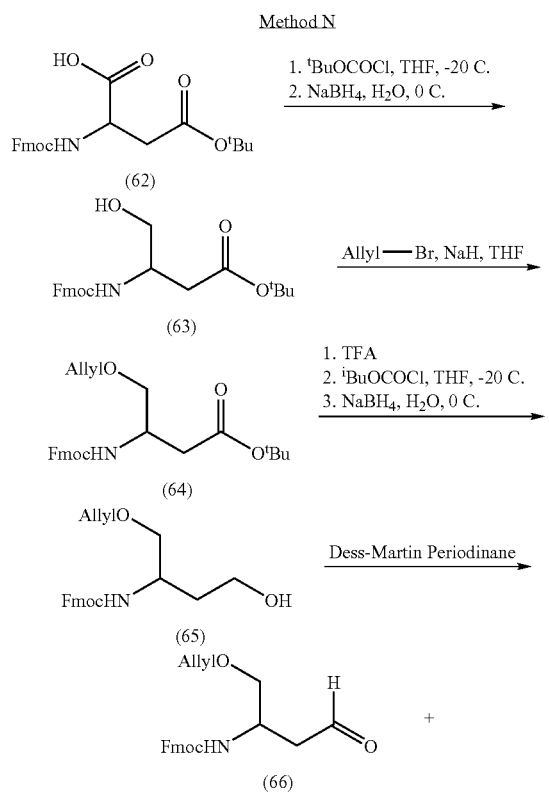

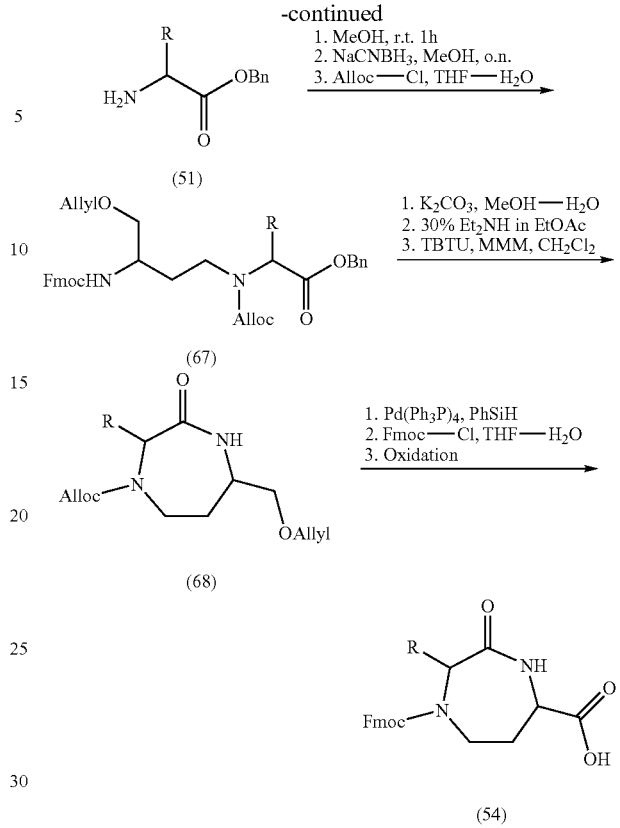

Synthesis of Fmoc-Aspartanol β tert-butyl ester (63): Compound (63) is prepared as described for the synthesis of compound (13), using Fmoc-Aspartic acid β tert-butyl ester (62) as the starting material.

Synthesis of 3-Fmoc-amino-4-allyloxy-butyric acid tert-butyl ester (64): To a solution of 10 mmol of (63) in 30 mL of tetrahydrofuran, kept at room temperature under nitrogen, is added 12 mmol of 60% sodium hydride dispersion in mineral oil, 2 mmol of tetrabutylammonium iodide, and 13 mmol allyl bromide, and the mixture is stirred overnight, quenched with 10 mL of saturated aqueous sodium bicarbonate, and extracted with 50 mL of ethyl acetate.

Synthesis of 3-Fmoc-amino-4-allyloxy-1-butanol (65): Compound (65) is prepared as described for the synthesis of compound (44).

Synthesis of 3-Fmoc-amino-4-allyloxy-butanal (66): 3-Fmoc-amino-4-allyloxy-1-butanol (65) is oxidized to the aldehyde using Dess-Martin periodinane as described for the synthesis of (9).

Synthesis of (3-Fmoc-amino-4-allyloxy-butyl-alloc-amino)-2-substituted acetic acid methyl ester (67): reductive amination of 3-Fmoc-amino-4-benzyloxy-butanal (66) with an α-amino ester (51) using either sodium cyanoborohydride or sodium triacetoxyborohydride as the reducing agent as described for compound (10), followed by protection of the secondary amine as the alloc derivative, is done as described for compound (15), but using allyl chloroformate instead of benzyl chloroformate.

Synthesis of 4-Alloc-7-allyloxymethyl-3-substituted-[1,4]-diazepan-2-ones (68): A solution of 10 mmol of (3-Fmoc-amino-4-allyloxy-butyl-alloc-amino)-2-substituted acetic acid methyl ester (67), 20 mmol of potassium carbonate in 20 mL of methanol, and 10 mL of water is stirred at room temperature for 3 hours, neutralized with 21 mL of a 1N hydrochloric acid solution, and then concentrated to dryness. The residue is dissolved in 20 mL of 30% diethyl amine in ethyl acetate and stirred at 3 hours, and then concentrated to dryness. The residue is dissolved in 100 mL of dichloromethane, and 12 mmol of TBTU and 24 mmol of N-methylmorpholine are added, and the solution stirred at room temperature overnight, and then concentrated to dryness. The residue is partitioned between 30 mL of ethyl acetate and 30 mL of 1N hydrochloric acid solution, and then the layers separated. The organic layer is washed with 30 mL of a saturated sodium bicarbonate solution, dried over magnesium sulfate, and purified by silica gel column chromatography.

Synthesis of 4-Fmoc-2-substituted-3-oxo-[1,4]-diazepane-5-carboxylic acid (54): To solution of 10 mmol of compound (68) in 30 mL of dichloromethane, kept at room temperature under nitrogen, is added 2 equivalents of phenylsilane and 0.3 equivalents of tetrakistriphenylphosphine palladium (0), and the solution then stirred for 2 hours, and concentrated to dryness. The secondary amine is dissolved in 20 mL of tetrahydrofuran, and 10 mL of water, followed by the addition of 2.52 g (30 mmol) of solid sodium bicarbonate, and 1.2 equivalents of Fmoc-Cl and the biphasic solution is stirred at room temperature for 2 hours, diluted with 30 mL of ethyl acetate, and the layers separated. Oxidation of 4-Fmoc-7-hydroxymethyl-3-substituted-[1,4]-diazepan-2-ones to the final product (54) is done as described in method A. The choice of the oxidizing agent used is based on the nature of the group in the 2-position, as in Method A for the conversion of (6) to (7).

Synthesis of
6-substituted-5-oxo-piperazine-2-carboxylic acid
Scaffolds

Method O

The syntheses of 6-substituted-5-oxo-piperazine-2-carboxylic acid scaffolds containing non-functionalized side chains in the 6-position are done as outlined in Method O, starting from commercially available 3-Fmoc-amino-1,2-propan-diol 1-chloro-trityl resin (69) which is oxidized to the ketone (70) using Dess-Martin periodinane. Reductive amination of ketone (70) with an α amino ester (2) gives resin bound (1-aminomethyl-2-chloro-trityloxy-ethylamino)-2-substituted acetic acid methyl ester (71), which is cyclized to 5-chlorotrityloxymethyl-3-substituted-piperazin-2-one (72) after deprotection of the amine. Reprotection of the secondary amine, followed by cleavage from the resin, gives Fmoc-5-hydroxymethyl-3-substituted-piperazin-2-one (73) which is oxidized to 6-substituted-5-oxo-piperazine-2-carboxylic acid (74) using either of the procedures described in method A.

Method O

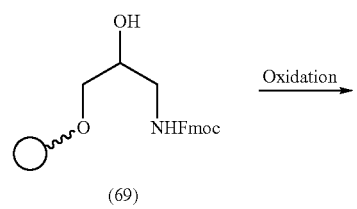

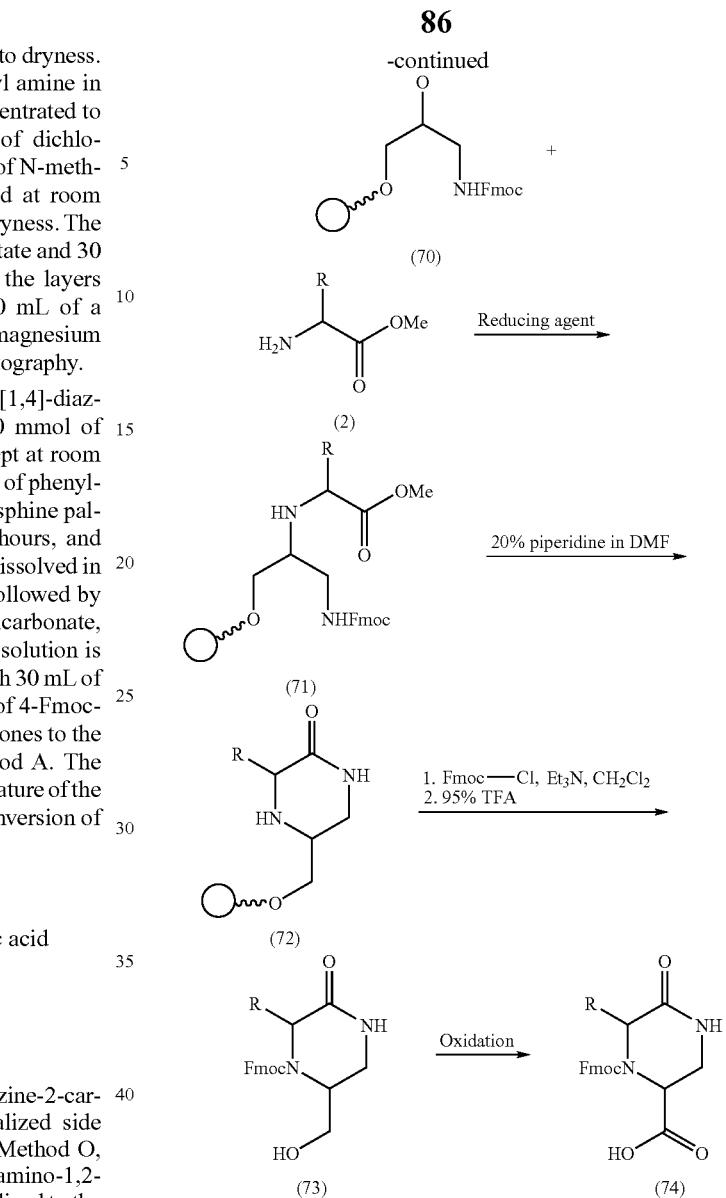

Synthesis of 1-amino-3-chlortrityloxy-propan-2-one (70): the oxidation of resin bound alcohol (69) is done by sulfur trioxide oxidation, NMO/TPAP (N-methylmorpholine-N-oxide/tetrapropyl ammonium perrthenate) oxidation, or PDC oxidation. For sulfur trioxide oxidation, a procedure similar to the one described in Parikh, J. R. and Doering, W. V., *J. Am. Chem. Soc.* 89:5505-5507 (1967) is used. For NMO/TPAP oxidation, to 0.3 mmol of resin-bound alcohol is added a solution of 3 mmol of N-methylmorpholine N-oxide in 10 mL of dry dimethylformamide, and then 0.06 mmol of tetrapropylammonium perruthenate (TPAP) is added to the resin suspension. The reaction is shaken for 80 minutes. The solvent is drained, the resin washed with tetrahydrofuran and dichloromethane, and then dried under vacuum. For PDC oxidation, a suspension of resin bound alcohol in 0.2 M pyridinium dichromate in dimethylformamide is shaken at 37° C. for 4 hours, the solvent is drained, and the resin washed with dimethylformamide, tetrahydrofuran, and dichloromethane.

Synthesis of (1-aminomethyl-2-chloro-trityloxy-ethylamino)-2-substituted acetic acid methyl ester (71): the reductive amination of resin bound ketone (70) with amino ester is done by one of two different methods. In one method, a solution of 2.6 mmol of α amino ester (2) in 20 mL of 1% acetic acid in dimethylformamide is added 2.6 mmol of sodium triacetoxyborohydride, followed by the immediate addition of 0.5 mmol of ketone-derivatized resin (70), and the mixture is shaken for 60 minutes, rinsed with methanol, 10% di-isopropyl ethyl amine, dimethylformamide, and methanol. In a second method, a suspension of 0.05 mmol of ketone-derivatized resin (70) and 2.0 Mα amino ester hydrochloride (2) in methanol, containing 0.05 M sodium cyanoborohydride is shaken at room temperature for 5 hours, drained, and washed.

Synthesis of 5-chlorotrityloxymethyl-3-substituted-piperazin-2-one (72): A suspension of 0.05 mmol of resin in 10 mL of 20% piperidine in dimethylformamide is shaken at room temperature for 2 hours.

Synthesis of Fmoc-5-hydroxymethyl-3-substituted-piperazin-2-one (73): A suspension of 0.05 mmol of (72) in 10 mL of dichloromethane, containing 0.25 mmol of Fmoc-Cl and 0.25 mmol of triethyl amine is stirred at room temperature for 6 hours, drained, and washed with dichloromethane. The resin is resuspended in 10 mL of 95% trifluoroacetic acid in dichloromethane, and the suspension shaken for 2 hours, and filtered, and the filtrate is concentrated.

Synthesis of Fmoc-6-substituted-5-oxo-piperazine-2-carboxylic acid (74): Oxidation of (73) to the desired product is done by any of the procedures described for method A.

Synthesis of α,α-Disubstituted Amino Acids

Methods P and Q

In certain of the constructs of the invention, it is possible and contemplated to employ a disubstituted amino acid residue, such as an α,α-disubstituted amino acid where the substituents are either the same or different. In one aspect, an α,α-disubstituted amino acid is employed in either the Aaa[1] or Aaa[8] position, wherein at least one of the side chains of the α,α-disubstituted amino acid is a side chain of Nle, Ala, Leu, Ile, Val, Nva, Met(O) or Met($O_2$). The following synthetic Methods P and Q describe making α,α-di-n-butylglycine (2-Amino-2-butyl-hexanoic acid), wherein each of the side chains are —$(CH_2)_3$—$CH_3$, and thus each is the same as the side chain of Nle. However, it is to be understood that similar methods and schemes may be employed in the making of other α,α-disubstituted amino acids, where the substituents are either the same or different. Additionally, any method of making an α,α-disubstituted amino acid may be employed in the practice of this invention, and the practice of this invention is not limited to the methods of the following synthetic schemes. Thus any method known in the art for the synthesis of α,α-disubstituted amino acids may be employed in the practice of this invention. The following teach alternative methods for the making of α,α-disubstituted amino acids: Clark J. S, and Middleton M. D.: Synthesis of novel alpha-substituted and alpha,alpha-disubstituted amino acids by rearrangement of ammonium ylides generated from metal carbenoids. Org. Lett. 4(5):765-8 (2002); Guino M., Hii K. K.: Wang-aldehyde resin as a recyclable support for the synthesis of alpha, alpha-disubstituted amino acid derivatives. Org. Biomol. Chem. 3(17):3188-93 (2005); and Kotha S., Behera M.: Synthesis and modification of dibenzylglycine derivatives via the Suzuki-Miyaura cross-coupling reaction. J. Pept. Res. 64(2):72-85 (2004).

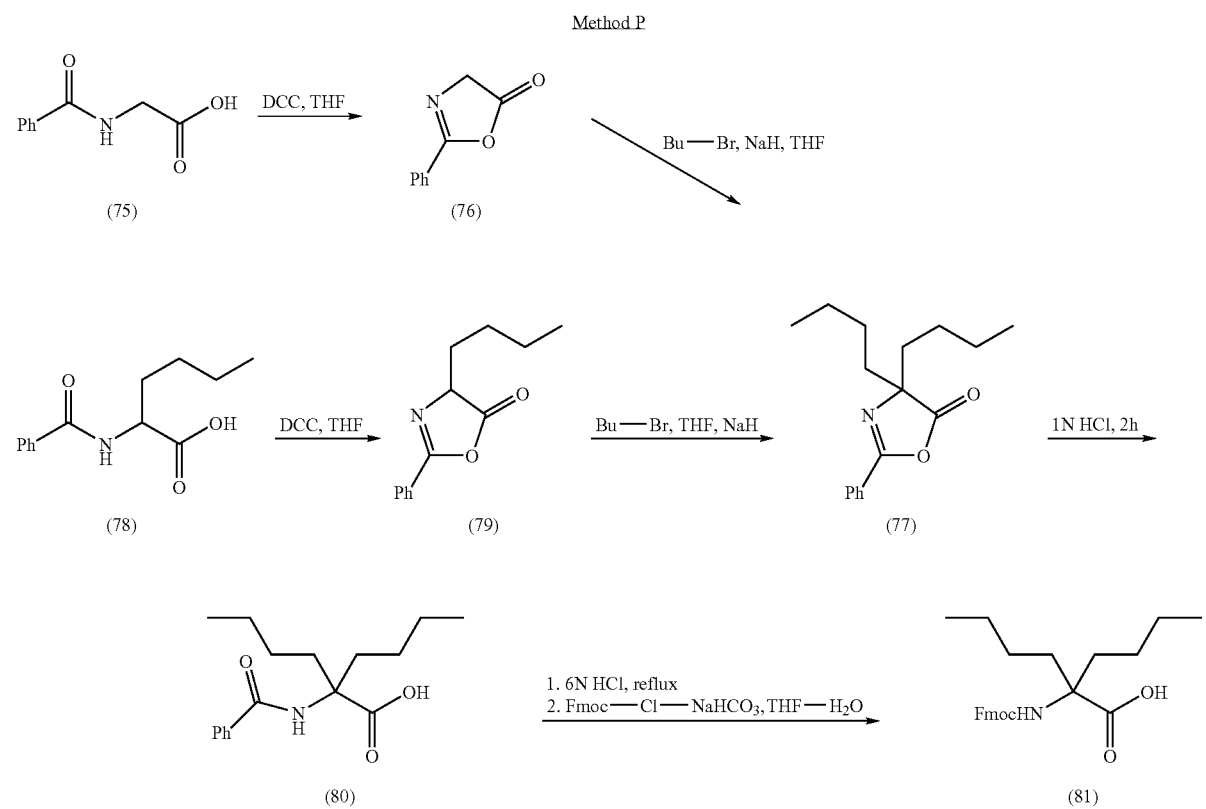

Synthesis of Benzoyl di-n-butylglycine (80): To a solution of 10 mmol benzoyl glycine (75) in 20 mL of dichloromethane, kept at 0° C. under nitrogen, is added slowly 12 mmol of N,N'-dicyclohexylcarbodiimide (DCC), and the reaction stirred for 2 hours to yield compound (76). The solid is filtered off, and the filtrate concentrated. The residue is dissolved in 15 mL of tetrahydrofuran, cooled to 0° C., and then 24 mmol of sodium hydride is added, followed by 30 mmol of n-butyl bromide. The suspension is stirred at 0° C. for 2 hours and then allowed to warm to room temperature, and the solution concentrated to dryness to yield compound (77). Alternatively, compound (77) can also be prepared from benzoyl norleucine (78) in a similar manner except that 12 mmol of sodium hydride and 15 mmol of n-butyl bromide are used. Compound (77) is dissolved in methanol, 50 mL of 1N hydrochloric acid solution is added, and the solution stirred for 2 hours, and concentrated. Compound (80) is purified by silica gel column chromatography.

Synthesis of Fmoc di-n-butylglycine (81): 10 mmol of compound (80) is dissolved in 30 mL of dioxane, and 10 mL of 6N hydrochloric acid solution is added, and the solution is refluxed overnight. The reaction is cooled to room temperature, concentrated to dryness, redissolved in 30 mL of tetrahydrofuran, and 10 mL of water and 30 mmol of sodium bicarbonate is added, followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dry over sodium sulfate, and concentrated. Compound (81) is purified by silica gel column chromatography.

Similar methods may be employed by starting with any appropriate amino acid derivative (similar to compound 78), and by using an appropriate alkyl butyl, aryl butyl, or aralkyl butyl reagent the scheme will yield a variety of disubstituted (R, R') amino acid surrogates where R and R' are different.

Synthesis of Fmoc-α,α di-n-butyl glycine (87): To a suspension of 20 mmol of glycine methyl ester hydrochloride (82), and 2 g of powdered molecular sieves in 40 mL of dry tetrahydrofuran, kept at room temperature, is added 24 mmol of potassium hydroxide, followed by 22 mmol of benzaldehyde. The suspension is stirred for 2 hours, filtered, and the filtrate concentrated. The residue is redissolved in 40 mL of dry toluene, and then added to a suspension of 60 mmol of sodium hydride in toluene, followed by the addition of 60 mmol of n-butyl bromide. The suspension is stirred for 12 hours, followed by addition of 30 mL of a solution of 6N hydrochloric acid, stirred at room temperature for 2 hours, and then the layers separated. The hydrochloride salt of (84) thus obtained is used in situ for preparation of (87). To isolate (84) as the hydrochloride salt the aqueous layer is concentrated to dryness and the product crystallized from dry methanol-ether.

Alternatively, compound (84) can be prepared from norleucine methyl ester hydrochloride using a similar synthetic procedure except that 30 mmol of sodium hydride and 30 mmol of n-butyl bromide are used for conversion of (86) to (84).

The aqueous mixture of the hydrochloride form of compound (84) as obtained above is heated to reflux for 1 hour and then cooled to room temperature. It is neutralized with solid sodium hydroxide and then diluted with 30 mL of tetrahydrofuran. Sodium bicarbonate (30 mmol) is added followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dried over sodium sulfate, and concentrated. Compound (87) is purified by silica gel column chromatography.

Similar methods may be employed by starting with any appropriate amino acid derivative (similar to compound 85), and by using an appropriate alkyl butyl, aryl butyl, or aralkyl butyl reagent the scheme will yield a variety of disubstituted (R, R') amino acid surrogates where R and R' are different.

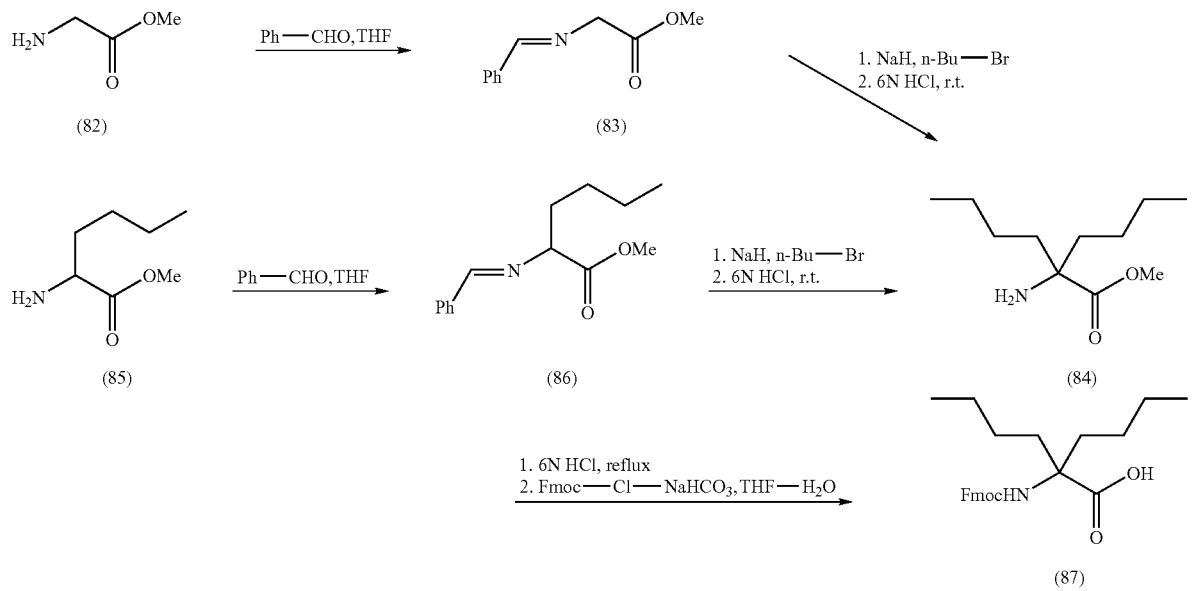

Synthesis of Disubstituted (R, R') Scaffolds

Method R

The invention further provides for constructs in which amino acid surrogates are employed with two R groups, R and R'. The following method describes synthesis of Fmoc protected (R)-5,5-dibutyl-6-oxo-piperazine-2-carboxylic acid, where R and R' are each groups corresponding to a norleucine side chain moiety. It may be seen that the method below may be modified, based in part on the foregoing methods, to produce similar disubstituted (R, R') amino acid surrogates. Similar methods may be employed such that starting with any appropriate amino acid derivative (a compound similar to compound (84)) the scheme can yield a variety of disubstituted (R, R') amino acid surrogates where R and R' are different.

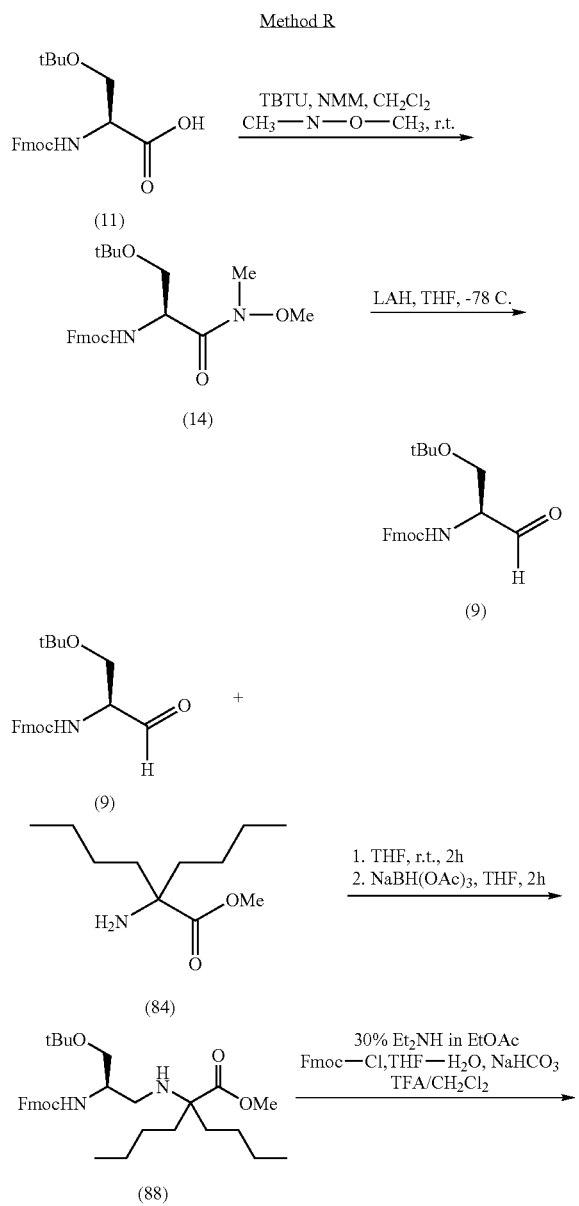

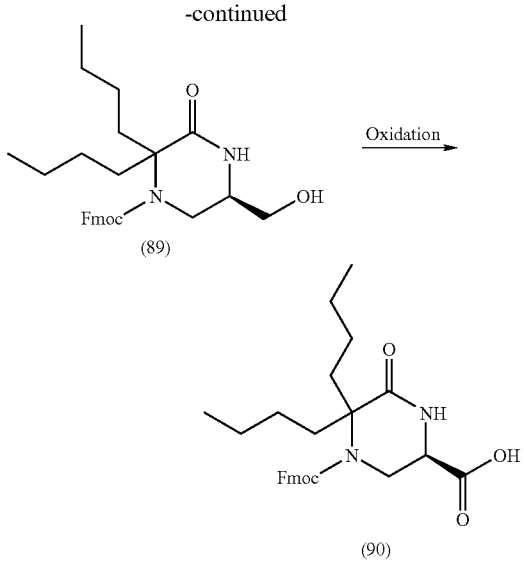

Synthesis of (2-Fmoc-amino-3-tert-butoxy-propylamino)-2,2,di-n-butyl acetic acid methyl ester (88): A suspension of 21 mmol of (84, scheme Q), and 2.9 mL (21 mmol) of triethyl amine in 50 mL of dry tetrahydrofuran, is stirred at room temperature for 45 minutes, and then a solution of ~20 mmol crude Fmoc-(O-t-butyl)-serinal (9, scheme D) in 30 mL of tetrahydrofuran is added, followed by 1.7 g of 4 Å powdered molecular sieves, and the suspension is stirred for an additional 2 hours. 6.4 g (30 mmol) of solid sodium triacetoxyborohydride is added, and the suspension stirred at room temperature overnight. The suspension is diluted with methanol, the molecular sieves filtered, and the filtrate concentrated. The residue is partitioned between 100 mL of ethyl acetate and 50 mL of water. The organic layer is dried over sodium sulfate, filtered, and concentrated. Compound (88) is purified by silica gel column chromatography.

Synthesis of 4-Fmoc-6-hydroxymethyl-3,3-di-n-butyl-piperazin-2-one (89): A solution of 10 mmol of compound (88) in 30 mL of 30% diethyl amine in ethyl acetate is stirred at room temperature overnight, and then concentrated to dryness. The residue is dissolved in 20 mL of tetrahydrofuran and 10 mL of water, 2.52 g (30 mmol) of solid sodium bicarbonate is added, followed by 3.36 g (13 mmol) of Fmoc-Cl. The mixture is stirred for 3 hours, diluted with 50 mL of ethyl acetate, the layers separated, and the organic layer washed with 30 mL of water, dried over magnesium sulfate, and concentrated. The crude mixture is dissolved in a solution of 10 mL of 90% trifluoroacetic acid in dichloromethane, stirred for 2 hours, and then concentrated to dryness. The residue is dissolved in ethyl acetate and washed with 50 mL of a saturated solution of sodium bicarbonate, dried over magnesium sulfate, and concentrated. Compound (89) is purified by silica gel column chromatography.

Synthesis of 4-Fmoc-5,5-di-n-butyl-6-oxo-piperazine-2-carboxylic acid (90): To a solution of 8 mmol alcohol (89) in 81 mL of acetonitrile kept at room temperature, is added phosphate buffer solution (prepared with 0.72 g of sodium phosphate monobasic and 1.43 g of sodium phosphate dibasic in 29.5 mL of water), followed by the addition of 0.33 g (2.1 mmol) of TEMPO, and 1.86 g (16.5 mmol) of sodium chlorite, and the biphasic solution is placed in an oil bath kept at 43° C. A solution of 4.3 mL (2.6 mmol) of sodium hypochlorite solution (prepared by mixing 1.9 mL of 10-13% sodium hypochlorite solution, and 2.4 mL of water) is added slowly.

The reaction is stirred at 43° C. for 4 hours, cooled to room temperature, 20 mL of 10% sodium hydrogen sulfite added, stirred for 10 minutes, diluted with 50 mL of ethyl acetate, and the layers separated. The organic layer is washed with 1×10 mL of brine, 1×10 mL of 1N hydrochloric acid solution, dried over sodium sulfate, and concentrated. Compound (90) is purified by silica gel column chromatography.

6. Synthetic Methods for Compounds Including Surrogates of Formula I

The compounds including one or more surrogates of formula I as disclosed in the several embodiments of this invention may be readily synthesized by any known conventional procedure for the formation of a peptide linkage between amino acids. Such conventional procedures include, for example, any solution phase procedure permitting a condensation between the free alpha amino group of an amino acid residue having its carboxyl group or other reactive groups protected and the free primary carboxyl group of another amino acid residue having its amino group or other reactive groups protected. In a preferred conventional procedure, the compounds of this invention may be synthesized by solid-phase synthesis and purified according to methods known in the art. The amino acid surrogates of the present invention may be incorporated into compounds of this invention by methods substantially similar to or identical to those employed with residues. Any of a number of well-known procedures utilizing a variety of resins and reagents may be used to prepare the compounds of this invention.

The process for synthesizing the compounds may be carried out by a procedure whereby each amino acid or amino acid surrogate in the desired sequence is added one at a time in succession to another amino acid residue or amino acid surrogate or by a procedure whereby peptide fragments with the desired amino acid sequence, which may include one or more amino acid surrogates, are first synthesized conventionally and then condensed to provide the desired compound. The resulting compound is cyclized to yield a cyclic compound of the invention.

Solid phase peptide synthesis methods are well known and practiced in the art. In such methods the synthesis of compounds of the invention can be carried out by sequentially incorporating the desired amino acid residues or amino acid surrogates one at a time into the growing peptide chain according to the general principles of solid phase methods. These methods are disclosed in numerous references, including Merrifield R. B., Solid phase synthesis (Nobel lecture). *Angew. Chem.* 24:799-810 (1985) and Barany et al., *The Peptides, Analysis, Synthesis and Biology*, Vol. 2, Gross E. and Meienhofer J., Eds. Academic Press, 1-284 (1980).

In chemical syntheses of compounds, reactive side chain groups of the various amino acid residues or amino acid surrogates are protected with suitable protecting groups, which prevent a chemical reaction from occurring at that site until the protecting group is removed. Also common is the protection of the alpha amino group of an amino acid residue or amino acid surrogate while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf), Fmoc and Boc. Pbf is one preferred protecting group for Arg. Other preferred protecting groups include Z, Fmoc, and Boc. It is to be understood that particularly guanidino protecting groups may be cleaved and removed during the synthetic process, or may alternatively not be cleaved or removed, in which event the side chain with the protecting group forms a derivative of an amino acid side chain moiety as defined herein. Particularly where the protecting group is labile, and may be removed by some mechanism in vivo upon administration to a patient, the compound becomes a "prodrug", which is to say a compound that is a drug precursor which, following administration to a patient, is converted to the desired drug form in vivo via some chemical or physiological process (e.g., a prodrug on being brought to physiological pH or through enzyme action is converted to the desired drug form).

The compounds of the invention described herein can be prepared using solid phase synthesis, either manually or by means of an automated peptide synthesizer, using programming modules as provided by the manufacturer and following the protocols set forth by the manufacturer, or by modifications of the manufacturer's protocols to improve the yield of difficult couplings.

Solid phase synthesis is commenced from the C-terminal end of the compound by coupling a protected α-amino acid, α-amino acid surrogate or α-amino alcohol mimetic to a suitable resin. Such starting material is prepared by attaching an α-amino-protected amino acid or α-amino-protected amino acid surrogate by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art, such as by attaching an α-amino-protected alcohol mimetic to 3,4-dihydro-2H-pyran-2-yl-methanol linker attached to chloromethyl polystyrene resin. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids or amino acid surrogates are coupled stepwise in the desired order to obtain an intermediate, protected peptide-resin. The activating reagents used for coupling of the amino acids in the solid phase synthesis of the peptides are well known in the art. After the compound is synthesized, if desired, the orthogonally protected side chain protecting groups may be removed using methods well known in the art for further derivatization of the compound.

Reactive groups in a compound can be selectively modified, either during solid phase synthesis or after removal from the resin. For example, compounds can be modified to obtain N-terminus modifications, such as acetylation, while on resin, or may be removed from the resin by use of a cleaving reagent and then modified. Methods for N-terminus modification, such as acetylation, or C-terminus modification, such as amidation or introduction of an N-acetyl group, are known in the art. Similarly, methods for modifying side chains of amino acids are well known to those skilled in the art of peptide synthesis. The choice of modifications made to reactive groups present on the compound will be determined, in part, by the characteristics that are desired in the compound.

The compounds are, in one embodiment, cyclized prior to cleavage from the resin. For cyclization through reactive side chain moieties, the desired side chains are deprotected, and the compound suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCl/HOBt). Coupling is conventionally initiated by use of a suitable base, such as N,N-diisopropylethylamine (DIPEA), sym-collidine or N-methylmorpholine (NMM).

Following cleavage of compounds from the solid phase following synthesis, the compound can be purified by any number of methods, such as reverse phase high performance liquid chromatography (RP-HPLC), using a suitable column, such as a $C_{18}$ column. Other methods of separation or purification, such as methods based on the size or charge of the compound, can also be employed. Once purified, the compound can be characterized by any number of methods, such as high performance liquid chromatograph (HPLC), amino acid analysis, mass spectrometry, and the like.

Compounds of the present invention with a substituted amide derivative C-terminus, typically an N-alkyl group, are prepared by solid phase synthesis commenced from the C-terminal end of the compound by coupling a protected alpha amino acid or amino acid surrogate to a suitable resin. Such methods for preparing substituted amide derivatives on solid phase have been described in the art. See, for example, Barn D. R., Morphy J. R., Rees D. C. Synthesis of an array of amides by aluminum chloride assisted cleavage of resin-bound esters. *Tetrahedron Lett.* 37, 3213-3216 (1996); DeGrado W. F. Kaiser E. T. Solid-phase synthesis of protected peptides on a polymer bound oxime: Preparation of segments comprising the sequences of a cytotoxic 26-peptide analogue. *J. Org. Chem.* 47:3258-3261 (1982). Such starting material can be prepared by attaching an alpha amino-protected amino acid or amino acid surrogate by an ester linkage to a p-benzyloxybenzyl alcohol (Wang) resin by well known means. The peptide chain is grown with the desired sequence of amino acids or amino acid surrogates, the product cyclized and resin-treated with a solution of appropriate amine and aluminum chloride (such as methyl amine, dimethyl amine, ethylamine, and so on) in dichloromethane. The resulting amide derivative compound is released in solution from the resin. The resin is filtered and the amide derivative compound recovered by concentration of solvent followed by precipitation with ether. The crude compound is dried and remaining amino acid side chain protective groups cleaved using trifluoroacetic acid (TFA) in the presence of water and 1,2-ethanedithiol (EDT). The final product is precipitated by adding cold ether and collected by filtration. Final purification is by RP-HPLC using a $C_{18}$ column.

In one preferred method, compounds were synthesized by the following methods. Each of the compounds had one or two amino acid surrogates based on a keto-piperazine structure. The amino acid surrogates were synthesized as described above. The compounds were synthesized using Fmoc chemistry. A manual synthetic approach was used for couplings immediately before and after incorporation of the keto-piperazine amino acid surrogate.

The following protocol was employed to attach an amino acid surrogate to resin, such as where the amino acid surrogate was in a terminal position. Rink amide resin (loading at 0.3 mmol/g, Advanced ChemTech) was allowed to swell in DMF for 30 minutes. Fmoc deprotection of the resin was accomplished using 20% piperidine/DMF for 20 minutes. Coupling of the resin with the selected Fmoc-protected keto-piperazine amino acid surrogate (2 eq) was accomplished by overnight incubation in DMF with PyBop (2 eq) and DIEA (4 eq). If following Kaiser testing a positive result was obtained, the coupling reaction was conducting a second time. Acetylation was carried out using $Ac_2O$ (10 eq) and pyridine (20 eq) in DMF.

The following protocol was employed to attach a keto-piperazine amino acid surrogate to peptide-resin. Coupling was carried out by mixing Fmoc-protected keto piperazine amino acid surrogate (2 eq), TBTU (2 eq) and DIEA (4 eq) in DMF and allowing to incubate overnight, again with a repeat of the coupling reaction if a positive Kaiser test obtained. Acetylation was carried out using $Ac_2O$ (10 eq) and pyridine (20 eq) in DMF.

The following protocol was employed to couple an Fmoc-protected amino acid to a keto-piperazine amino acid surrogate on solid phase. In most instances at least two coupling cycles were needed, and frequently three cycles were employed. In a typical cycle Fmoc-protected amino acid (4 eq) was mixed with HOAt (4 eq) and DIC (4 eq) in DMF for 30 minutes. The resulted mixture was then mixed overnight in a SPE tube with a keto-piperazine amino acid surrogate attached directly or through intermediates to resin.

Couplings between amino acids that were not directly adjacent to a keto-piperazine amino acid surrogate in the sequence were conducted using standard protocols for solid phase peptide synthesis. The following protecting groups were employed: Boc for Lys and Orn, t-Butyl for Tyr and Ser, Trityl for Cys and His, O-t-Butyl for Asp and Pbf for Arg.

Compounds were cleaved from resin employing a mixture of TFA/thioanisole/phenol/$H_2O$/EDT (87.5/2.5/2.5/5/2.5) (5 mL) for 3 hours. The resulting material was filtered and precipitated from cold ether under freezing conditions for one hour. Precipitated cysteinyl peptide was washed with cold ether at least three times before being use in an oxidation step.

For cyclization to form disulfide bonds via air oxidation, crude cysteinyl compound was dissolved in a mixture of acetonitrile and water. The pH of the reaction mixture was adjusted to 7-8 using 5% $NH_4OH$. The resulted solution was stirred slowly with 150 mg granular activated carbon for 2 days. Completion of cyclization was confirmed by LC-MS analysis before proceeding to the next process step. After cyclization, solid carbon was filtered from solution. The filtrate was lyophilized or dried in a speed-vac to obtain crude cyclic compound.

Certain compounds of the invention, where the surrogate of formula I is bound to resin or other peptide solid support and is at the C-terminal position, may be synthesized by means of the following scheme.

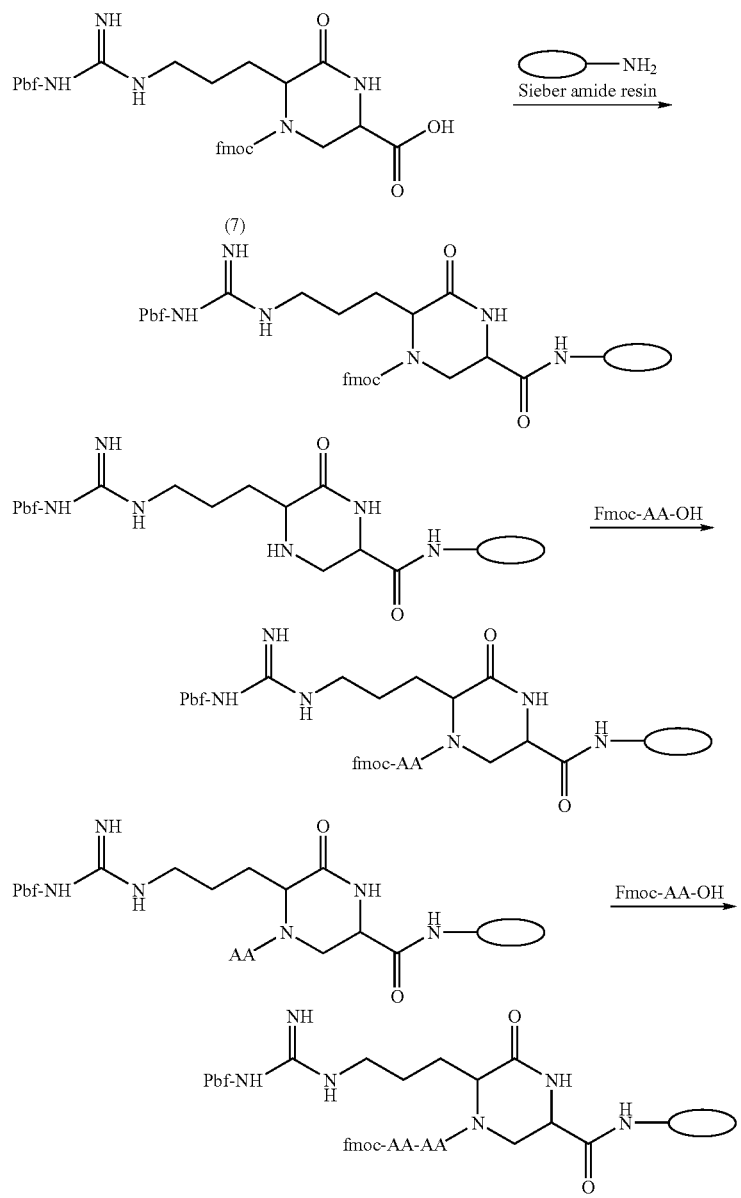

Surrogate (7) is prepared by the scheme of method A above, or any alternative method. Fmoc protected Sieber amide resin was treated by swelling the resin in a 1:1 mixture of dimethylformamide and dichloromethane for 45 minutes, followed by filtering and washing with dimethylformamide. The washed resin was then deprotected with 20% piperidine in dimethylformamide for 15 minutes, filtered, and washed with dimethylformamide.

A solution of Fmoc-protected surrogate (7) in dimethylformamide was added to the deprotected Sieber amide resin as prepared above, followed by solid PyBop and diisopropylethylamine, followed by additional dimethylformamide. The mixture was agitated overnight with nitrogen bubbling. The resin was filtered, and washed with of dimethylformamide, capped with capping solution consisting of a 3:2:1 solution of dimethylformamide:acetic anhydride:pyridine for 30 minutes, filtered, and washed with dimethylformamide to provide surrogate (7) complexed to resin.

The resulting Fmoc-protected surrogate (7) complexed to resin was deprotected with 20% piperidine in dimethylformamide for 15 minutes, filtered, and washed with dimethylformamide to yield surrogate (7) complexed to resin. A solution of the desired Fmoc-AA-OH (4 eq, where AA is any desired amino acid) in dimethylformamide was added to surrogate (7) complexed to resin, followed by a solution of HCTU (60 mmol, 4 eq), and diisopropylethylamine (120 mmol, 8 eq.) in DMF and coupled overnight with nitrogen bubbling. The resulting Fmoc-AA-surrogate (7)-resin was isolated by filtration and washed with dimethylformamide. In order to ensure complete coupling, the product was again treated with a solution of Fmoc-AA-OH as above overnight with nitrogen bubbling. The resulting resin was filtered and washed with dimethylformamide.

The resulting Fmoc-AA-surrogate (7)-resin was then capped with capping solution as above for 30 minutes. The resin was then filtered, washed with dimethylformamide, dichloromethane, MeOH, and diethyl ether, and then dried under vacuum.

Thereafter each succeeding amino acid is coupled using conventional peptide coupling methods.

Optional PEGylation of compounds made employing a surrogate of formula I of the invention may be performed, including by the methods described below.

PEGylation of reactive amine groups, such as lysine or ornithine side chains, an omega amino aliphatic in the N-terminal position, or an amine group of a surrogate of formula I in the C-terminal position, was accomplished by dissolving 0.005 mmol purified compound in 2 mL of dimethylsulfoxide, followed by the addition of 55.5 mg (0.011 mmol, 2 eq) of PEG-5K-OSu (5,000 Da MW methoxy-PEG with a succinimidyl propionate reactive group), with 17.7 μL (0.13 mmol, 20 eq.) of triethyl amine then added, and the slightly cloudy solution stirred at room temperature for 3 hours. Excess PEG-5K-OSu was quenched by the addition of 7 μL (0.111 mmol, 10 eq.) of ethanol amine, and the reaction stirred overnight.

PEGylation of reactive carboxyl groups, such as Asp or Glu side chains or a terminal carboxyl on a compound on either a terminal amino acid residue or a terminal surrogate of formula I, is accomplished by coupling PEG-NH$_2$ (PEG-amine), to the construct containing a carboxylate group in the side chain of Asp or Glu or at the C-terminus. The peptide construct (0.005 mmol) is dissolved in DMSO (2 mL), followed by the addition of 55.5 mg (0.011 mmol, 2 eq) of PEG-NH$_2$ and HOBt (0.01 mmol). The coupling is started by the addition of 0.0055 mmole of coupling reagent N-ethyl-N'-(3-dimethylaminopropyl)-carbodiimide (EDAC). The slightly cloudy solution stirred at room temperature overnight. The PEGylated peptide construct is then purified by HPLC.

PEGylation of reactive thiol groups, such as Cys or Hcys side chains or a thiol group in R$^1$ of the surrogate of formula I, is accomplished by treating the compound in DMSO with PEG-methyl-maleimide reagent (SunBio, Orinda, Calif.) overnight. The PEGylated compound is then purified by HPLC.

Following PEGylation, the resulting crude compound mixture is purified by HPLC, yielding a PEG derivatized compound including one or more amino acid surrogates.

7. Assays for Determining Efficacy of Compounds Including Surrogates of Formula I In general, any assay system appropriate for a parent polypeptide may be employed. The following exemplifies assay systems employed where the parent polypeptide is an ANP peptide, such as mini-ANP. Selected compounds including at least one surrogate of formula I were tested in assays to determine binding and functional status. The following assays were employed.

Cell culture. A cDNA clone that encodes for human natriuretic peptide receptor A (NPRA) was purchased from Bio S&T Inc. (Montreal, Quebec). The cDNA clone was inserted into the mammalian expression vector pcDNA3.1 (Invitrogen) and transfected into HEK-293 cells. Stable clones were selected by culture of cells in the presence of G418 sulfate. Expression of NPRA was examined by binding of [$^{125}$I]-atrial natriuretic peptide ([$^{125}$I]-ANP) to membrane homogenates prepared from clonal cell lines. HEK-hNPRA cells were maintained in culture at 37° C. in 5% CO$_2$ in Dulbecco's Modified Eagle's Medium (DMEM) supplemented with 10% FBS, G418 sulfate (300 μg/mL) sodium glutamate (0.29 mg/mL), penicillin (100 units/mL) and streptromycin (100 μg/mL).

Competitive binding assay. A competitive inhibition binding assay was performed using crude membrane homogenates prepared from HEK-hNPRA cells. To prepare membrane homogenates, cells were rinsed with phosphate-buffered saline and incubated for 15 minutes at 4° C. in hypotonic lysis buffer (10 mM Tris, pH 7.4+5 mM EDTA). Cells were transferred from plates to polypropylene tubes and homogenized. Homogenates were centrifuged at 25,000×g for 20 minutes. Pellets were resuspended in buffer consisting of 50 mM Tris (pH 7.4) and 1 mM EDTA, homogenized and centrifuged at 25,000×g for 20 minutes. Pellets were resuspended in buffer consisting of 100 mM Tris (pH 7.4) and 10 mM MgCl$_2$ and stored at −80° C. until needed. On the day of an assay, homogenates were thawed and homogenized. Binding of [$^{125}$I]-ANP was carried out in buffer containing 25 mM Hepes (pH 7.4), 100 mM NaCl, 2 mM CaCl$_2$, 5 mM MgCl$_2$, 0.1% BSA and 1 mM 1,10-phenanthroline. Homogenates (1-10 μg protein/well) were incubated with [$^{125}$I]-ANP (25-30 pM) and increasing concentrations of competing ligands in Millipore filter plates for 120 minutes at 4° C. Assays were stopped by addition of cold wash buffer (phosphate-buffered saline) followed by filtration using a vacuum manifold. Bound radioactivity was determined using a gamma counter. Non-specific binding was defined by binding of [I$^{125}$]-hANP to non-transfected HEK293 membranes. Data were analyzed using GraphPad Prism® curve-fitting software.

General method for determination of EC$_{50}$. Functional evaluation of compounds was performed by measuring the accumulation of intracellular cGMP in HEK-293 cells that express recombinant hNPR-A. HEK-NPRA cells were harvested by washing and centrifugation in Cell Dissociation Buffer (Gibco, Life Technologies). Pelleted cells were resuspended in Hank's Balanced Salt Solution (HBSS) containing 10 mM Hepes (pH 7.4), 5 mM MgCl$_2$, 200 mM L-glutamine, 1 mM 1,10-phenanthroline and BSA (0.5 mg/mL). Following centrifugation, cells were resuspended in the above buffer supplemented with 0.5 mM 3-isobutyl-1-methylxanthine (IBMX). Cells (~2×10$^5$/well) were added to each well of a 96-well plate and incubated for 15 minutes at 37° C. Following the pre-incubation period, cells were incubated for an additional 15 minutes in the presence of increasing concentrations of compounds. The reaction was terminated by lysis of the cells with temperature shock. The reaction plate was incubated in a dry ice/ethanol bath for 15 minutes followed by incubation at 90° C. for 10 minutes. Accumulation of cGMP was measured using the cGMP Flashplate RIA (Perkin-Elmer). Data analysis and EC$_{50}$ values were determined by using nonlinear regression analysis with GraphPad Prism® software.

Determination of mass and nuclear magnetic resonance analysis. The mass values were determined using a Waters MicroMass ZQ device utilizing a positive mode. Mass determinations were compared with calculated values and expressed in the form of mass weight plus two divided by two (M+2)/2, unless otherwise specified.

Proton NMR data was obtained using a Bruker 300 MHz spectrometer. The spectra were obtained after dissolving compounds in a deuteriated solvent such as chloroform, DMSO, or methanol as appropriate.

HPLC measurements were made using a Waters Alliance HT with a YMC Pack Pro C-18 column (4.6×50 mm, 3μ) eluted at 1 mL/minute in a step-wise procedure. Solvent A (water containing 0.1% trifluoroacetic acid v/v) and solvent B (acetonitrile containing 0.1% trifluoroacetic acid v/v) were used as mobile phases. For analysis of keto piperazine intermediates, the column was equilibrated with 10% B and then B was increased to 90% over a period of 8 minutes. For analysis of peptides, the column was equilibrated with 2% B and then B was increased to 90% over a period of 8 minutes.

8. Compounds Including Surrogates of Formula I

The invention is further illustrated by the following non-limiting examples.

EXAMPLE 1

The following compounds based upon the parent polypeptide H-Met-cyclo(Cys-His-Phe-Gly-Gly-Arg-Met-Asp-Arg-Ile-Ser-Cys)-Tyr-Arg-NH$_2$ (SEQ ID NO:1) were synthesized, each employing a single amino acid surrogate of formula I of one or more of the foregoing methods. For synthetic reasons, Met in position 1 was substituted with Nle. The resulting compounds were purified and the mass weights determined, with the results as shown below:

TABLE 1

| Number (M + 2)/2 | Structure |
|---|---|
| 1-1 932.0 | 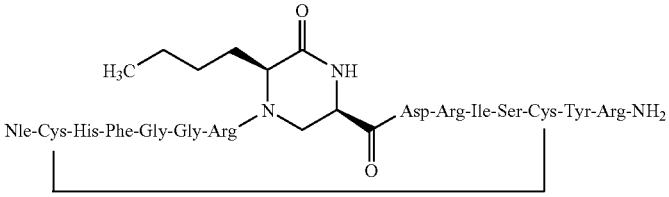 |
| 1-2 931.9 | 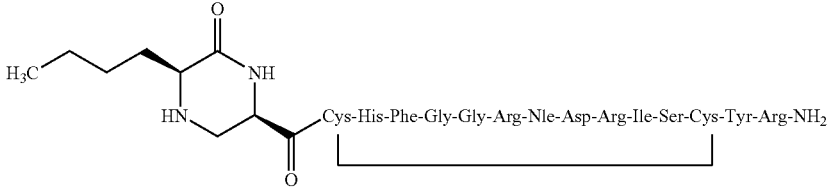 |
| 1-3 932.0 | 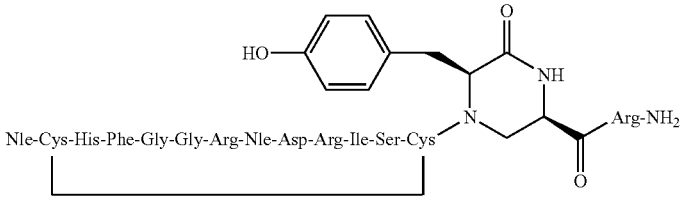 |
| 1-4 938.9 | 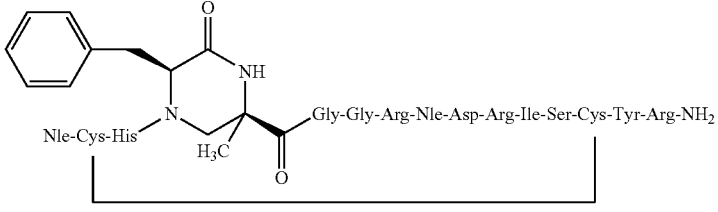 |
| 1-5 932.0 | 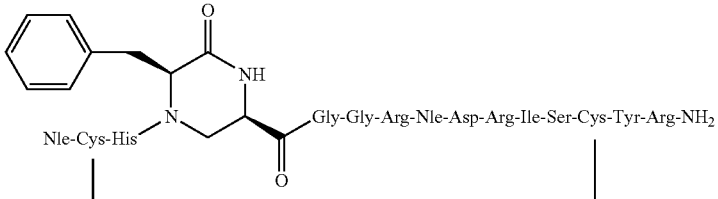 |
| 1-6 932.0 | 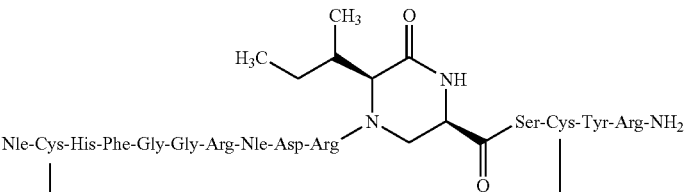 |

TABLE 1-continued
| Number (M + 2)/2 | Structure |
|---|---|
| 1-7 932.8 | 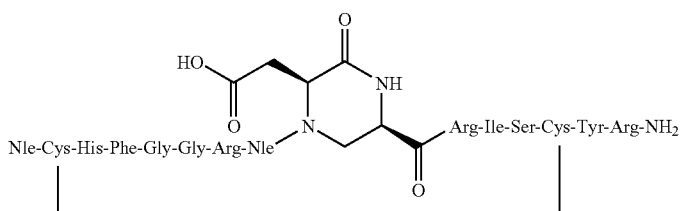 |
| 1-8 932.9 | 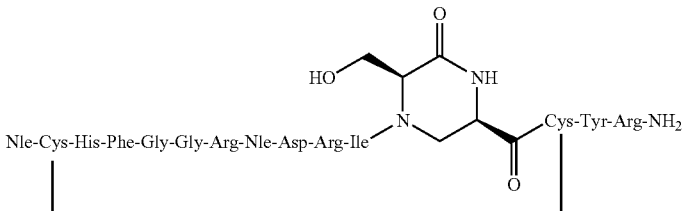 |
| 1-9 932.9 | 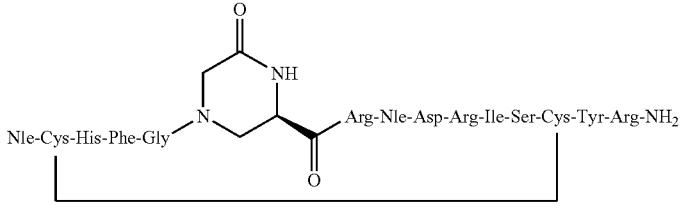 |
| 1-10 932.7 | 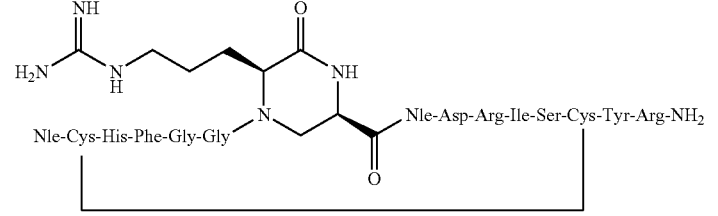 |
| 1-11 932.3 | 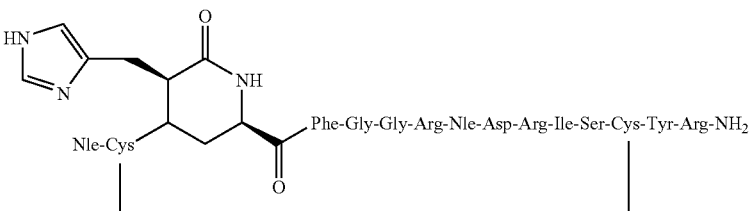 |
| 1-12 932.0 | 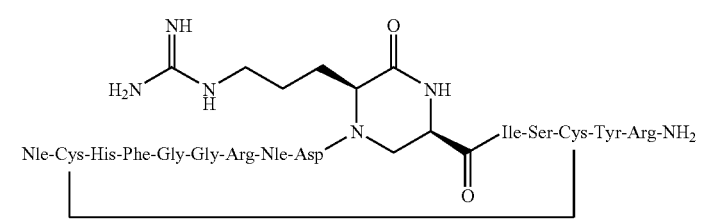 |

TABLE 1-continued
| Number (M + 2)/2 | Structure |
|---|---|
| 1-13 932.0 | 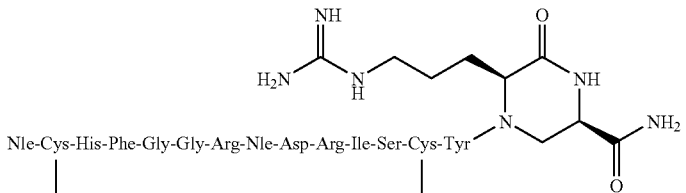 |
| 1-14 932.2 | 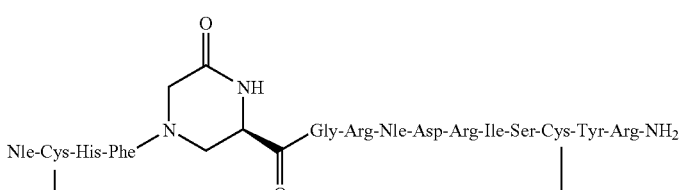 |
| 1-15 931.9 | 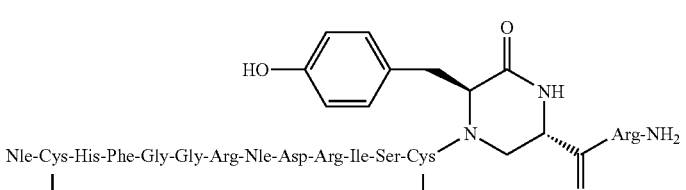 |
| 1-16 931.8 | 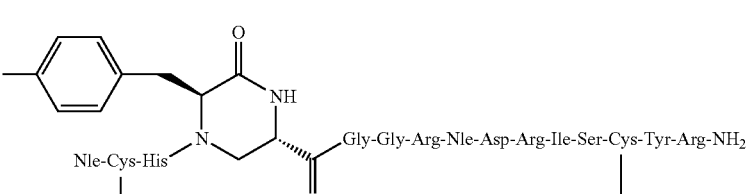 |
| 1-17 931.6 | 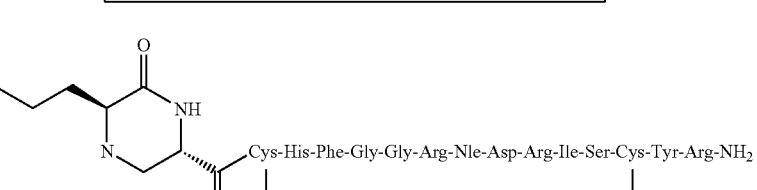 |
| 1-18 931.8 | 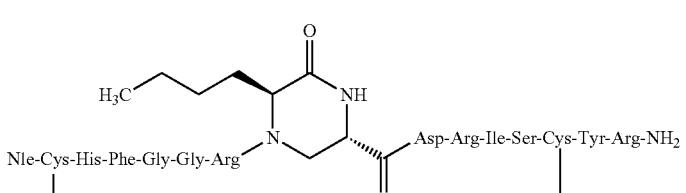 |
| 1-19 931.6 | 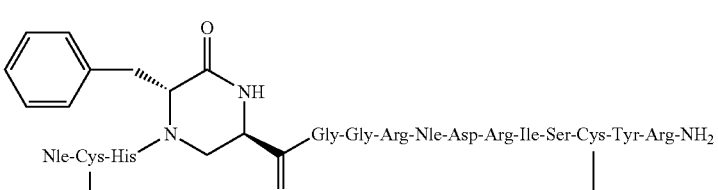 |

TABLE 1-continued
| Number (M + 2)/2 | Structure |
|---|---|
| 1-20 931.7 | 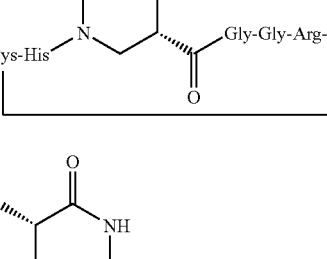 |
| 1-21 931.6 | 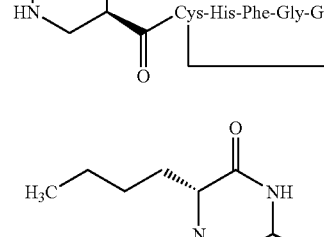 |
| 1-22 931.6 | 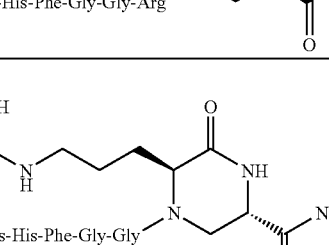 |
| 1-23 931.3 | 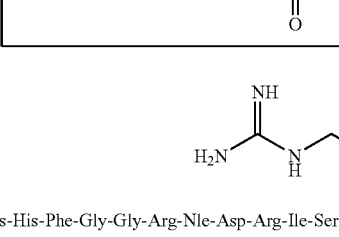 |
| 1-24 931.6 | 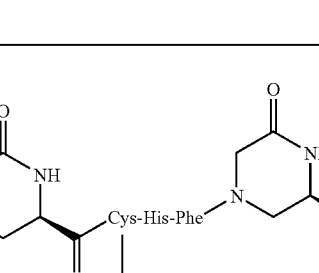 |
| 1-25 966.4 | 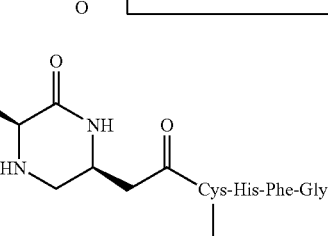 |
| 1-26 938.6 | 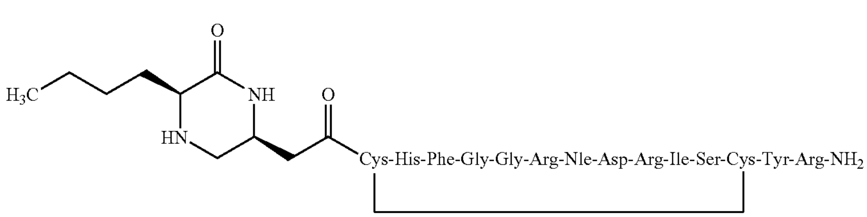 |

TABLE 1-continued

| Number (M + 2)/2 | Structure |
|---|---|
| 1-27 938.6 | 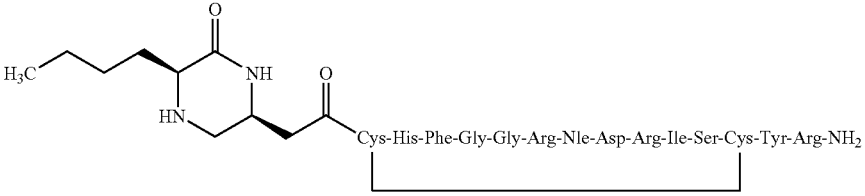 |

In the compounds of Table 1, compounds 1-1, 1-5, 1-7, 1-8, 1-12, 1-15, 1-18, 1-20 and 1-22 were inactive in relevant assay systems. The remaining compounds were active. Compound 1-2, with the following structure, was tested as described above.

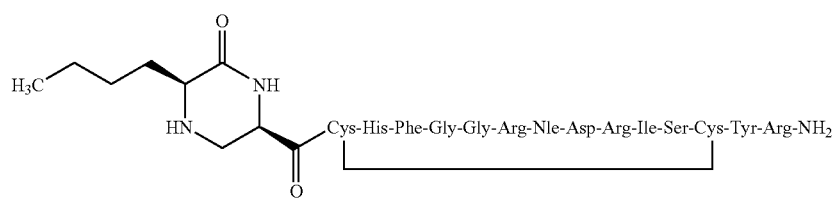

In receptor binding studies this compound had an average Ki of 0.3 nM in an assay system in which hANP had a Ki of 0.05 nM and mini-ANP had a Ki of 0.6 nM. Compound 1-2 had an $EC_{50}$ of 2 nM in an assay system in which hANP had an $EC_{50}$ of 0.6 nM and mini-ANP had an $EC_{50}$ of 3.3 nM.

Compound 1-14, with the following structure, was tested as described above.

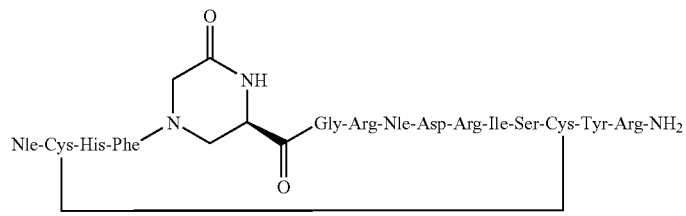

In receptor binding studies this compound had an average Ki of 0.9 nM in an assay system in which hANP had a Ki of 0.05 nM and mini-ANP had a Ki of 0.6 nM. Compound 1-14 had an $EC_{50}$ of 3.5 nM in an assay system in which hANP had an $EC_{50}$ of 0.6 nM and mini-ANP had an $EC_{50}$ of 3.3 nM.

Compound 1-13, with the following structure, was tested as described above.

In receptor binding studies this compound had an average Ki of 0.2 nM in an assay system in which hANP had a Ki of 0.05 nM and mini-ANP had a Ki of 0.6 nM. Compound 1-13 had an $EC_{50}$ of 2 nM in an assay system in which the construct of FIG. 1 had an $EC_{50}$ of 0.6 nM and mini-ANP had an $EC_{50}$ of 3.3 nM.

EXAMPLE 2

The following compounds based upon the parent polypeptide H-Met-cyclo(Cys-His-Phe-Gly-Gly-Arg-Met-Asp-Arg-Ile-Ser-Cys)-Tyr-Arg-NH$_2$ (SEQ ID NO:1) were synthesized, each employing two amino acid surrogates of formula I of one or more of the foregoing methods. For synthetic reasons, Met in position 1 was substituted with Nle. The resulting compounds were purified and the mass weights determined, with the results as shown below:

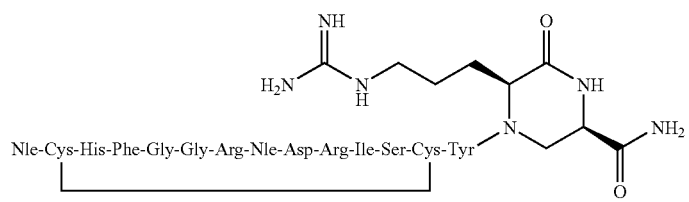

TABLE 2

| Number (M + 2)/2 | Structure |
| --- | --- |
| 2-1 966.4 | Cys-His-Phe-[piperazinone]-Gly-Arg-Nle-Asp-Arg-Ile-Ser-Cys-Tyr-Arg-NH₂ |
| 2-2 966.4 | Cys-His-Phe-Gly-[piperazinone]-Arg-Nle-Asp-Arg-Ile-Ser-Cys-Tyr-Arg-NH₂ |
| 2-3 966.4 | Cys-His-Phe-Gly-Gly-[piperazinone(Arg side chain)]-Nle-Asp-Arg-Ile-Ser-Cys-Tyr-Arg-NH₂ |
| 2-4 966.0 | Cys-His-Phe-Gly-Gly-Arg-Nle-Asp-Arg-[piperazinone(sec-Bu)]-Ser-Cys-Tyr-Arg-NH₂ |
| 2-5 966.0 | Cys-His-Phe-Gly-Gly-Arg-Nle-Asp-Arg-Ile-Ser-Cys-[piperazinone(Tyr side chain)]-Arg-NH₂ |
| 2-6 966.4 | Cys-His-Phe-Gly-Gly-Arg-Nle-Asp-Arg-Ile-Ser-Cys-Tyr-[piperazinone(Arg side chain)]-NH₂ |
| 2-7 965.7 | Cys-His-[piperazinone(Bn)]-Gly-Gly-Arg-Nle-Asp-Arg-Ile-Ser-Cys-Tyr-Arg-NH₂ |

TABLE 2-continued

| Number (M + 2)/2 | Structure |
|---|---|
| 2-8 965.9 | |
| 2-9 965.7 | |
| 2-10 965.6 | |

In the compounds of Table 2, compounds 2-2 and 2-4 were inactive in relevant assay systems. The remaining compounds were active. Compound 2-6, with the following structure, was tested as described above.

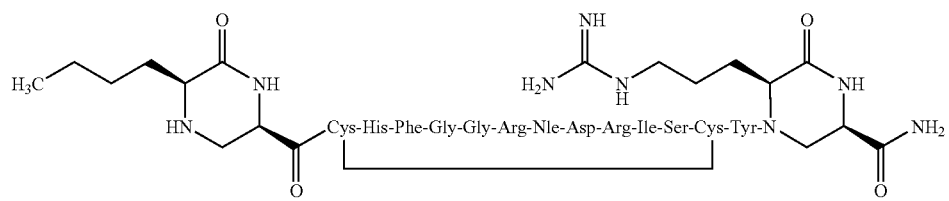

In receptor binding studies this compound had an average Ki of 0.027 nM in an assay system in which hANP had a Ki of 0.05 nM and mini-ANP had a Ki of 0.6 nM. Compound 2-6 had an $EC_{50}$ of 0.2 nM in an assay system in which hANP had an $EC_{50}$ of 0.6 nM and mini-ANP had an $EC_{50}$ of 3.3 nM.

EXAMPLE 3

The following compound based upon the parent polypeptide H-Met-cyclo(Cys-His-Phe-Gly-Gly-Arg-Met-Asp-Arg-Ile-Ser-Cys)-Tyr-Arg-$NH_2$ (SEQ ID NO:1) was synthesized, employing three amino acid surrogates of formula I of one or more of the foregoing methods. For synthetic reasons, Met in position 1 was substituted with Nle. The resulting compound was purified and the mass weights determined.

TABLE 3

| Number (M + 2)/2 | Structure |
|---|---|
| 3-1 1000.4 | [structure: H₃C-(piperazinone)-Cys-His-Phe-(piperazinone)-Gly-Arg-Nle-Asp-Arg-Ile-Ser-Cys-Tyr-(piperazinone with guanidine sidechain)-NH₂, with disulfide bridge between the two Cys residues] |

EXAMPLE 4

The following compounds based upon the parent polypeptide H-Met-cyclo(Cys-His-Phe-Gly-Gly-Arg-Met-Asp-Arg-Ile-Ser-Cys)-Tyr-Arg-NH₂ (SEQ ID NO:1) were synthesized, employing two amino acid surrogates of formula I of one or more of the foregoing methods and a PEG prosthetic group. For synthetic reasons, Met in position 1 was substituted with Nle. The resulting compounds were purified and the mass weights determined.

TABLE 4

| Construct (M + 1) | Structure |
|---|---|
| 4-1 6391-8332 | [structure: H₃C-(piperazinone)-Cys-Orn(PEG)-Phe-Gly-Gly-Arg-Nle-Asp-Arg-Ile-Ser-Cys-Tyr-(piperazinone with guanidine sidechain)-NH₂, disulfide bridge] |
| 4-2 6338-8412 | [structure: H₃C-(piperazinone)-Cys-His-Phe-Gly-Gly-Lys(PEG)-Nle-Asp-Arg-Ile-Ser-Cys-Tyr-(piperazinone with guanidine sidechain)-NH₂, disulfide bridge] |
| 4-3 6427-8159 | [structure: H₃C-(piperazinone)-Cys-His-Phe-Gly-Gly-Arg-Nle-Lys(PEG)-Arg-Ile-Ser-Cys-Tyr-(piperazinone with guanidine sidechain)-NH₂, disulfide bridge] |
| 4-4 6406-8219 | [structure: H₃C-(piperazinone)-Cys-Lys(PEG)-Phe-Gly-Gly-Arg-Nle-Asp-Arg-Ile-Ser-Cys-Tyr-(piperazinone with guanidine sidechain)-NH₂, disulfide bridge] |

TABLE 4-continued

| Construct (M + 1) | Structure |
|---|---|
| 4-5 11959-13514 | 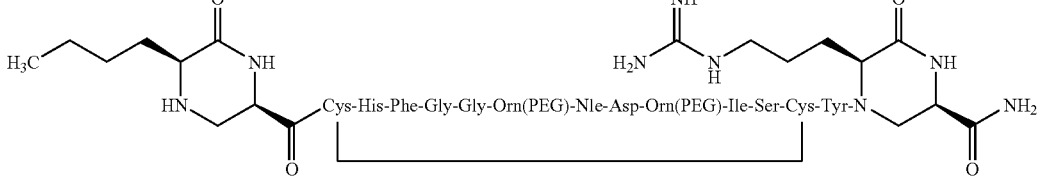 |
| 4-6 6479-8289 | 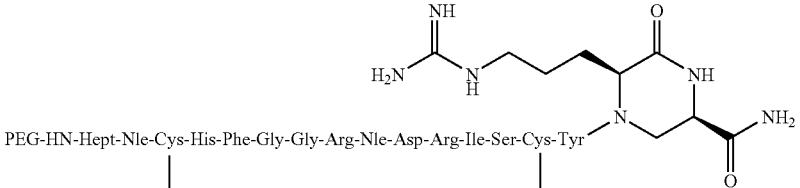 |
| 4-7 6602-8279 | 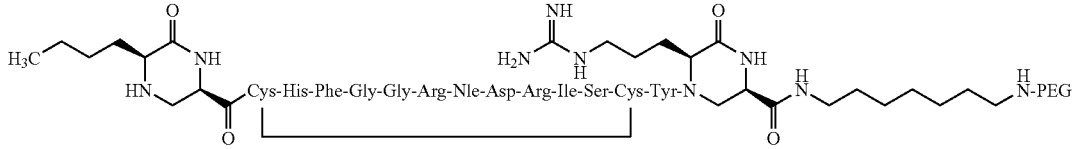 |
| 4-8 6506-8580 | 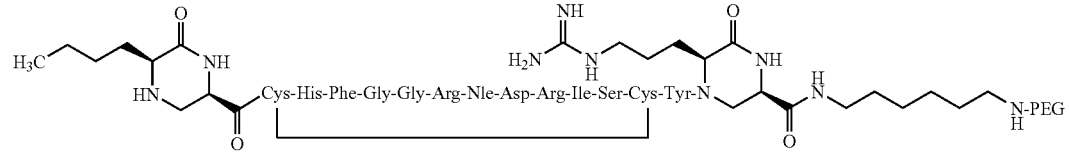 |
| 4-9 6319-8387 | 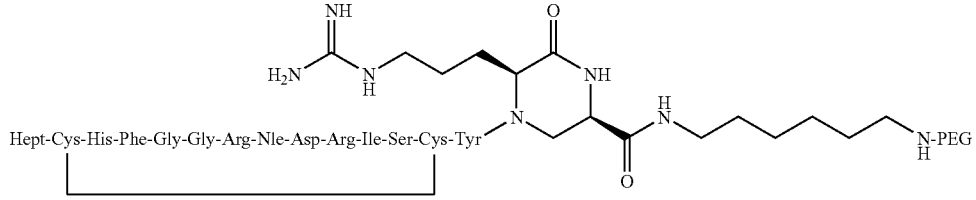 |

In the compounds of Table 4, compound 4-6 was inactive in relevant assay systems. The remaining compounds were active.

EXAMPLE 5

The following compounds based upon the parent polypeptide H-Met-cyclo(Cys-His-Phe-Gly-Gly-Arg-Met-Asp-Arg-Ile-Ser-Cys)-Tyr-Arg-NH$_2$ (SEQ ID NO:1) were synthesized, employing one or two amino acid surrogates of formula I of one or more of the foregoing methods. While the parent polypeptide was cyclic, these compounds were linear, with each Cys residue substituted with an Ala residue. For synthetic reasons, Met in position 1 was substituted with Nle.

Compound 5-1, with the following structure, was tested as described above.

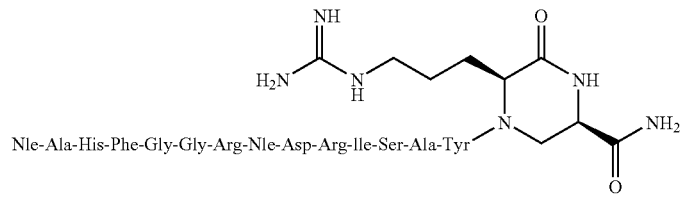

In receptor binding studies this compound had an average Ki of 88.5 nM in an assay system in which hANP had a Ki of 0.05 nM and mini-ANP had a Ki of 0.6 nM. Compound 5-1 had an $EC_{50}$ of 340 nM in an assay system in which hANP had an $EC_{50}$ of 0.6 nM and mini-ANP had an $EC_{50}$ of 3.3 nM.

Compound 5-2, with the following structure, was tested as described above.

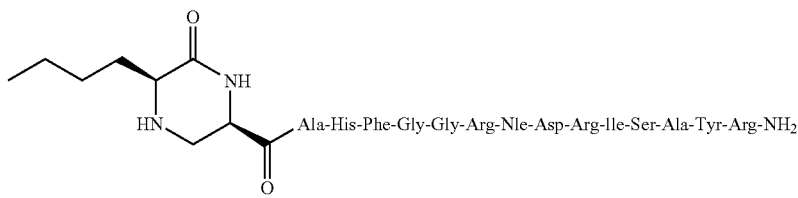

In receptor binding studies this compound had an average Ki of 14.5 nM in an assay system in which hANP had a Ki of 0.05 nM and mini-ANP had a Ki of 0.6 nM. Compound 5-2 had an $EC_{50}$ of 550 nM in an assay system in which hANP had an $EC_{50}$ of 0.6 nM and mini-ANP had an $EC_{50}$ of 3.3 nM.

Compound 5-3, with the following structure, was tested as described above.

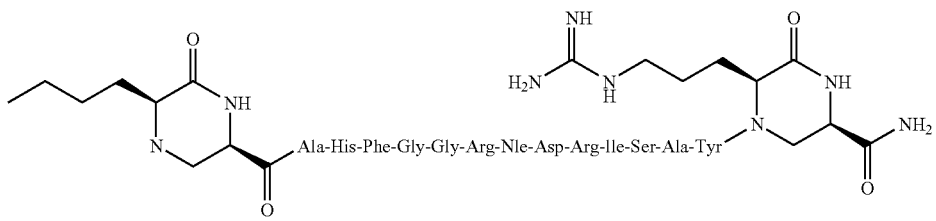

In receptor binding studies this compound had an average Ki of 8.7 nM in an assay system in which hANP had a Ki of 0.05 nM and mini-ANP had a Ki of 0.6 nM. Compound 5.3 had an $EC_{50}$ of 80.5 nM in an assay system in which hANP had an $EC_{50}$ of 0.6 nM and mini-ANP had an $EC_{50}$ of 3.3 nM.

EXAMPLE 6

The following compounds based upon the oxytocin parent polypeptide H-cyclo(Cys-Tyr-Ile-Gln-Asn-Cys)-Pro-Leu-Gly-NH$_2$ (SEQ ID NO:2) were synthesized, employing a single amino acid surrogates of formula I of one or more of the foregoing methods.

TABLE 6

| Construct | Structure |
|---|---|
| 6-1 | (structure shown) |

TABLE 6-continued

| Construct | Structure |
|---|---|
| 6-2 | 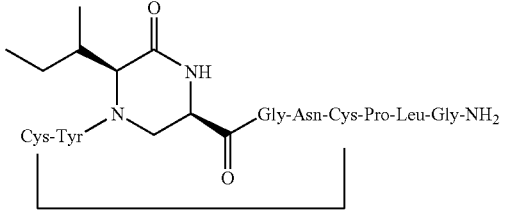 |
| 6-3 | 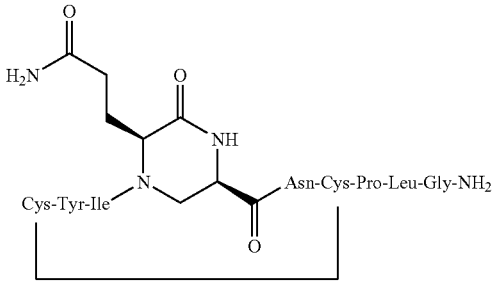 |
| 6-4 | 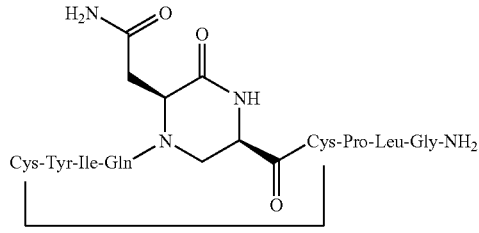 |
| 6-5 | 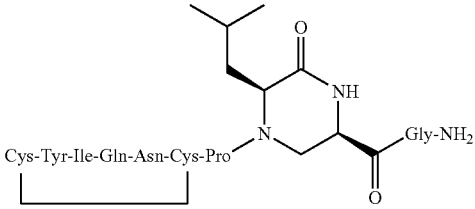 |
| 6-6 | 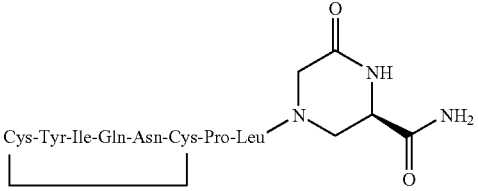 |

EXAMPLE 7

The following compounds based upon the oxytocin parent polypeptide H-cyclo(Cys-Tyr-Ile-Gln-Asn-Cys)-Pro-Leu Gly-NH$_2$ (SEQ ID NO:2) were synthesized, employing a single amino acid surrogates of formula I of one or more of the foregoing methods. While the parent polypeptide was cyclic, these compounds were linear, with each Cys residue substituted with an Ala residue.

TABLE 7
| Construct | Structure |
|---|---|
| 7-1 | 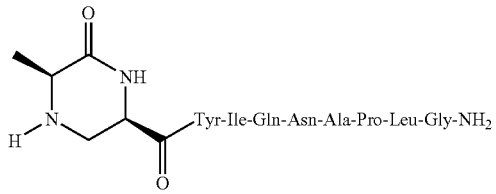 |
| 7-2 | 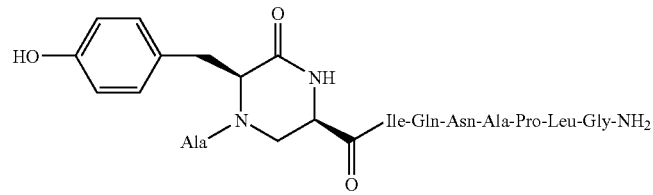 |
| 7-3 | 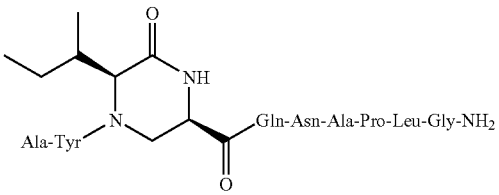 |
| 7-4 | 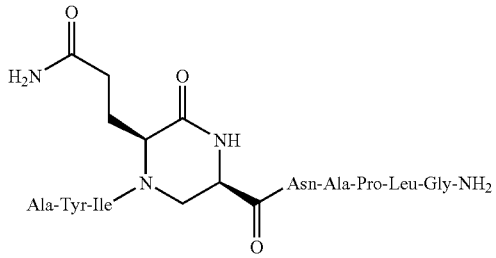 |
| 7-5 | 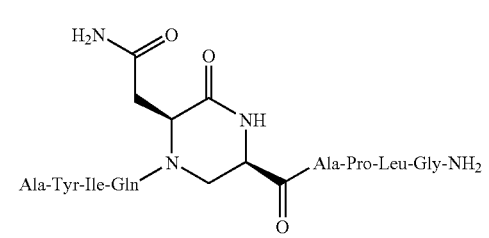 |
| 7-6 | 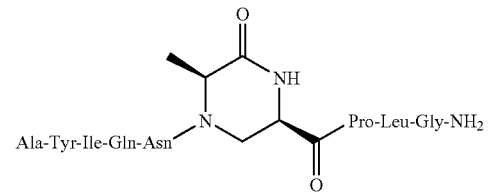 |
| 7-7 | 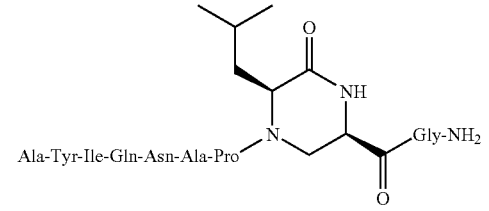 |

TABLE 7-continued

| Construct | Structure |
|---|---|
| 7-8 | Ala-Tyr-Ile-Gln-Asn-Ala-Pro-Leu attached to a piperazine-2,5-dione ring bearing a carboxamide (C(=O)NH₂) substituent |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A compound having a formula of structure I:

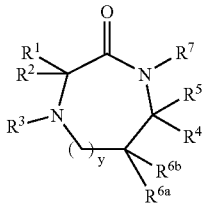

or a synthetically acceptable salt thereof, wherein:
$R^1$ is a group of a formula:

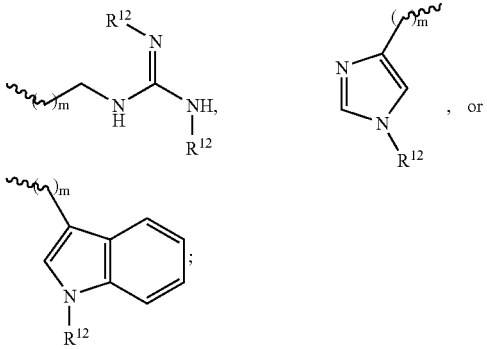

$R^2$ is H or alkyl;
$R^3$ is H or a first nitrogen protecting group;
$R^4$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^5$ is H or alkyl;
$R^{6a}$ is H, alkyl, $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^{6b}$ is H or alkyl;
provided that one of $R^4$ and $R^{6a}$ is H or alkyl and the other of $R^4$ and $R^{6a}$ is $(CH_2)_mC(=O)OH$, $(CH_2)_mC(=O)N(H)R^{11}$, $(CH_2)_mC(=O)OR^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$;
$R^7$ is H, C(=O)alkyl, $C(=O)(CH_2)_m(NR^8)_2$, alkyl, aralkyl, or aryl;
each occurrence of $R^8$ is independently H, aryl, or alkyl;
$R^{11}$ is a peptide solid support;
$R^{12}$ is H or a second nitrogen protecting group;
each occurrence of m is an independent integer having a value between 0 and 6;
each occurrence of q is an independent integer having a value between 1 and 6;
p is an integer having a value between 1 and 10; and
y is 0 or 1.

2. The compound of claim 1, wherein y is 1.
3. The compound of claim 1, wherein y is 0.
4. The compound of claim 1, wherein $R^4$ is $(CH_2)_mC(=O)OH$, $(CH_2)_mC(=O)N(R^8)_2$, $(CH_2)_mC(=O)N(H)R^{11}$, or $(CH_2)_mC(=O)OR^{11}$, and $R^{6a}$ is H or alkyl.

5. The compound of claim 1, wherein $R^{6a}$ is $(CH_2)_mC(=O)OH$, $(CH_2)_mC(=O)N(R^8)_2$, $(CH_2)_mC(=O)N(H)R^{11}$, or $(CH_2)_mC(=O)OR^{11}$, and $R^4$ is H or alkyl.

6. The compound of claim 1, wherein $R^3$ is a group of a formula:

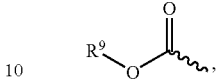

and $R^9$ is tert-butyl, allyl, or a group of a formula:

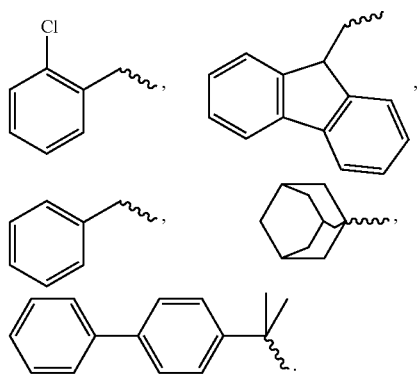

7. The compound of claim 1, wherein $R^1$ is the group of the formula:

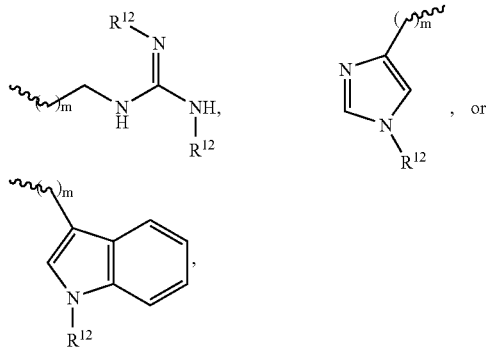

and $R^{12}$ is H or triphenylmethylene, tert-butyloxycarbonyl, toluenesulphonyl, formyl, nitro or benzyloxycarbonyl and m is, for $R^1$, an integer having a value between 2 and 6.

8. The compound of claim 1, wherein $R^7$ is H.
9. The compound of claim 1 having a formula:

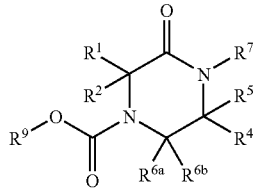

or a synthetically acceptable salt thereof, wherein:
$R^{6a}$ is H or alkyl; and
$R^9$ is tert-butyl, allyl, or a group of a formula:

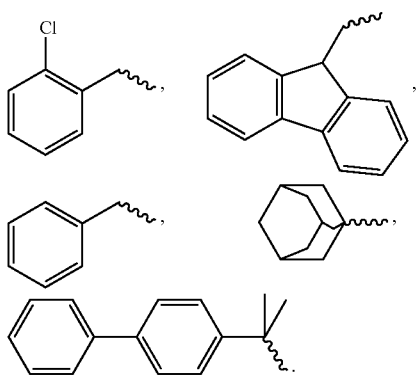
, 
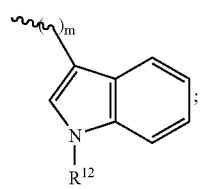

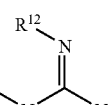

10. The compound of claim 9, wherein $R^1$ is the group of the formula:

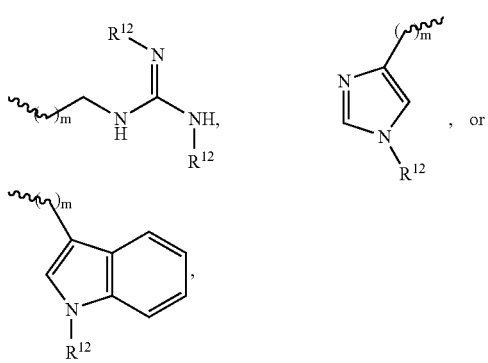

and $R^{12}$ is H or triphenylmethylene, tert-butyloxycarbonyl, toluenesulphonyl, formyl, nitro or benzyloxycarbonyl and m is, for $R^1$, an integer having a value between 2 and 6.

11. The compound of claim 9, wherein $R^7$ is H.

12. The compound of claim 9, wherein $R^4$ is $(CH_2)_m C(=O)OH$, $(CH_2)_m C(=O)N(R^8)_2$, or $(CH_2)_m C(=O)N(H)R^{11}$.

13. The compound of claim 1 having a formula:

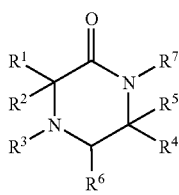

or a synthetically acceptable salt thereof, wherein:
$R^1$ is the group of the formula:

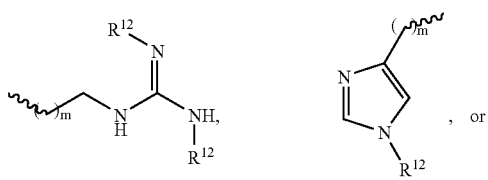

-continued

$R^4$ is $(CH_2)_m C(=O)OH$, $(CH_2)_m C(=O)N(H)R^{11}$, $(CH_2)_q OH$, $(CH_2)_q OBn$, $(CH_2)_q Oallyl$, $(CH_2)_m C(=O)N(R^8)_2$, or $(CH_2)_m C(=O)N(R^8)(CH_2)_p N(R^8)_2$;

$R^6$ is H or alkyl; and m is, for $R^1$, an integer having a value between 2 and 6.

14. The compound of claim 13, wherein $R^1$ is the group of the formula:

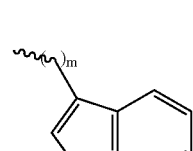

and $R^{12}$ is H or triphenylmethylene, tert-butyloxycarbonyl, toluenesulphonyl, formyl, nitro or benzyloxycarbonyl and m is, for $R^1$, an integer having a value between 2 and 6.

15. The compound of claim 13, wherein $R^7$ is H.

16. The compound of claim 13, wherein $R^4$ is $(CH_2)_m C(=O)OH$, $(CH_2)_m C(=O)N(R^8)_2$, $(CH_2)_m C(=O)N(H)R^{11}$, or $(CH_2)_m C(=O)OR^{11}$.

17. The compound of claim 1 having a formula:

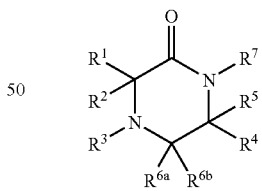

or a synthetically acceptable salt thereof, wherein:
$R^1$ is a group of a formula:

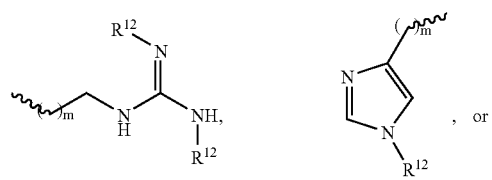

-continued

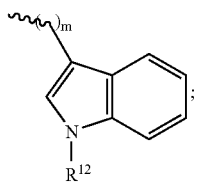

R[4] is H or alkyl;
R[6a] is $(CH_2)_mC(=O)OH$, $(CH_2)_mC(=O)N(H)R^{11}$, $(CH_2)_qOH$, $(CH_2)_qOBn$, $(CH_2)_qOallyl$, $(CH_2)_mC(=O)N(R^8)_2$, or $(CH_2)_mC(=O)N(R^8)(CH_2)_pN(R^8)_2$; and
m is, for R[1], an integer having a value between 2 and 6.

18. The compound of claim 17, wherein R[3] is a group of a formula:

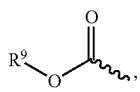

and R[9] is tert-butyl, allyl, or a group of a formula:

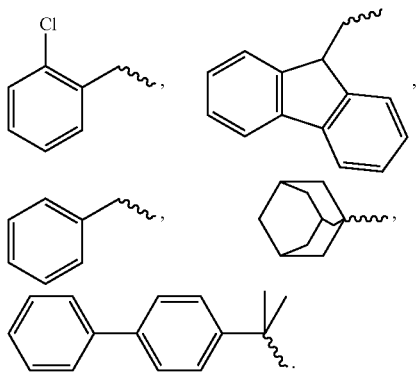

19. The compound of claim 17, wherein R[1] is alkyl-$N(R^8)_2$, alkyl-$OR^8$, $(CH_2)_m$—$C(=O)OR^8$, $C(=O)OR^8$, alkyl-S—$R^8$, alkyl-$C(=O)N(R^8)_2$, or the group of the formula:

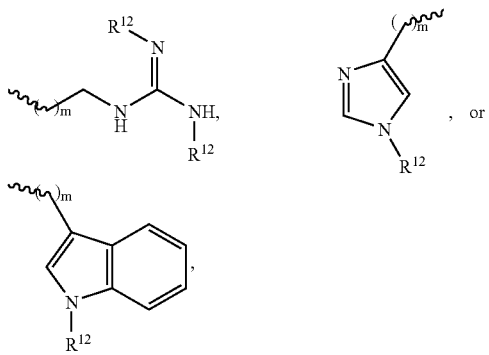

and R[12] is H or triphenylmethylene, tert-butyloxycarbonyl, toluenesulphonyl, formyl, nitro or benzyloxycarbonyl and m is, for R[1], an integer having a value between 2 and 6.

20. The compound of claim 17, wherein R[6a] is $(CH_2)_mC(=O)OH$, $(CH_2)_mC(=O)N(R^8)_2$, $(CH_2)_mC(=O)N(H)R^1$, or $(CH_2)_mC(=O)OR^{11}$.

21. The compound of claim 17, wherein R[7] is H.

22. The compound of claim 1 having a formula:

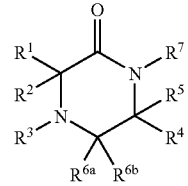

or an enantiomer, stereoisomer or diastereoisomer thereof, or a synthetically acceptable salt thereof, wherein:
R[4] is H or alkyl; and
R[9] is tert-butyl, allyl, or a group of a formula:

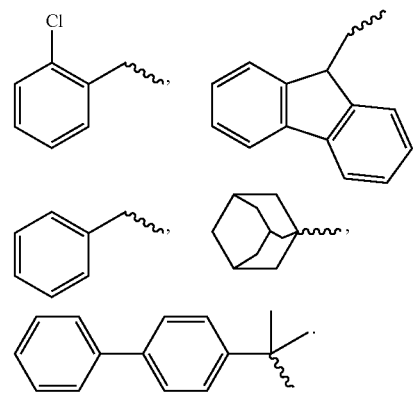

23. The compound of claim 22, wherein R[1] is the group of the formula:

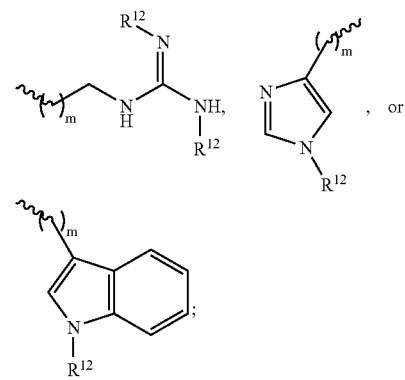

and R[12] is H or triphenylmethylene, tert-butyloxycarbonyl, toluenesulphonyl, formyl, nitro or benzyloxycarbonyl and m is, for R[1], an integer having a value between 2 and 6.

24. The compound of claim 22, wherein R[7] is H.

25. The compound of claim 22, wherein R[4] is $(CH_2)_mC(=O)OH$, $(CH_2)_mC(=O)N(R^8)_2$, $(CH_2)_mC(=O)N*H)R^{11}$, or $(CH_2)_mC(=O)OR^{11}$.

26. The compound of claim 22, wherein $R^3$ is a group of a formula:

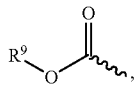

and $R^9$ is tert-butyl, allyl, or a group of a formula:

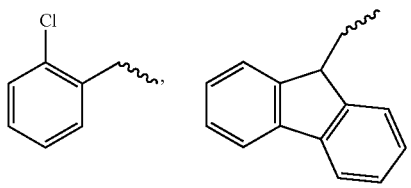

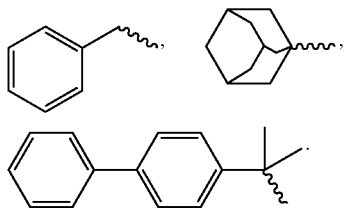

27. The compound of claim 22, wherein $R^{6a}$ is $(CH_2)_m C(=O)OH$, $(CH_2)_m C(=O)N(H)R^{11}$, $(CH_2)_m C(=O)OR^{11}$, $(CH_2)_q OH$, $(CH_2)_q OBn$, $(CH_2)_q Oallyl$, $(CH_2)_m C(=O)N(R^8)_2$, or $(CH_2)_m C(=O)N(R^8)(CH_2)_p N(R^8)_2$.

28. The compound of claim 22, wherein $R^7$ is H.

29. A method of synthesizing a peptide comprising a group of the formula:

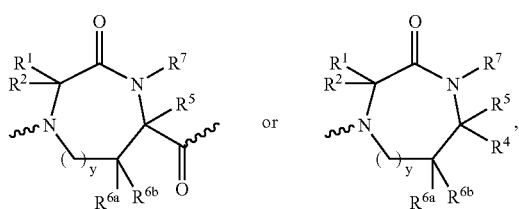

said method comprising the step of reacting a compound having a formula of structure I:

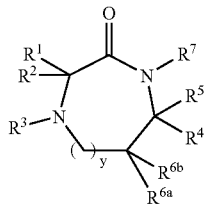

I or a synthetically acceptable salt thereof, with an N-protected amino acid, wherein:

$R^1$ is a group of a formula:

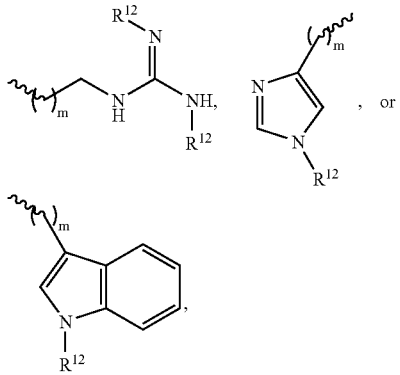

$R^2$ is H or alkyl;

$R^3$ is H or a first nitrogen protecting group;

$R^4$ is H, alkyl, $(CH_2)_m C(=O)OH$, $(CH_2)_m C(=O)N(H)R^{11}$, $(CH_2)_m C(=O)OR^{11}$, $(CH_2)_q OH$, $(CH_2)_q OBn$, $(CH_2)_q Oallyl$, $(CH_2)_m C(=O)N(R^8)_2$, or $(CH_2)_m C(=O)N(R^8)(CH_2)_p N(R^8)_2$;

$R^5$ is H or alkyl;

$R^{6a}$ is H, alkyl, $(CH_2)_m C(=O)OH$, $(CH_2)_m C(=O)N(H)R^{11}$, $(CH_2)_m C(=O)OR^{11}$, $(CH_2)_q OH$, $(CH_2)_q OBn$, $(CH_2)_q Oallyl$, $(CH_2)_m C(=O)N(R^8)_2$, or $(CH_2)_m C(=O)N(R^8)(CH_2)_p N(R^8)_2$;

$R^{6b}$ is H or alkyl;

provided that one of $R^4$ and $R^{6a}$ is H or alkyl and the other of $R^4$ and $R^{6a}$ is $(CH_2)_m C(=O)OH$, $(CH_2)_m C(=O)N(H)R^{11}$, $(CH_2)_m C(=O)OR^{11}$, $(CH_2)_q OH$, $(CH_2)_q OBn$, $(CH_2)_q Oallyl$, $(CH_2)_m C(=O)N(R^8)_2$, or $(CH_2)_m C(=O)N(R^8)(CH_2)_p N(R^8)_2$;

$R^7$ is H, $C(=O)$alkyl or $C(=O)(CH_2)_m (NR^8)_2$;

each occurrence of $R^8$ is independently H, aryl, or alkyl;

$R^{11}$ is a peptide solid support;

$R^{12}$ is H or a second nitrogen protecting group;

each occurrence of m is an independent integer having a value between 0 and 6;

each occurrence of q is an independent integer having a value between 1 and 6;

p is an integer having a value between 1 and 10; and y is 0 or 1.

30. A compound having a formula:

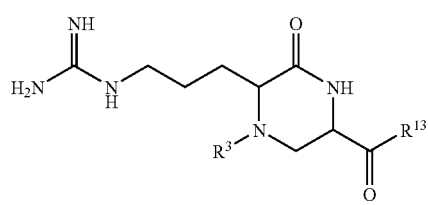

or a synthetically acceptable salt thereof, wherein:

$R^3$ is H or a first nitrogen protecting group;

each occurrence of $R^8$ is independently H, aryl, or alkyl; and $R^{13}$ is OH or $N(R^8)_2$.

31. The compound of claim 30, wherein $R^3$ is a first nitrogen protecting group of a formula:

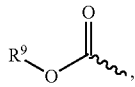

and $R^9$ is tert-butyl, allyl, or a group of a formula:

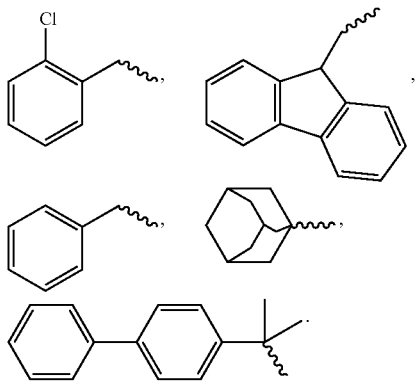

32. A compound having a formula of structure I:

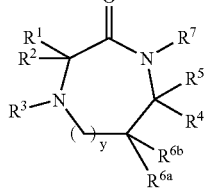

I or a synthetically acceptable salt thereof, wherein:
$R^1$ is alkyl-$OR^8$, alkyl-C(=O)$OR^8$, C(=O)$OR^8$, alkyl-S—$R^8$, alkyl-C(=O)N($R^8$)$_2$, or a group of a formula:

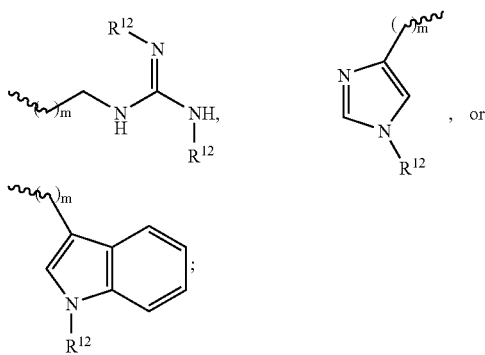

$R^2$ is H or alkyl;
$R^3$ is a first nitrogen protecting group of a formula:

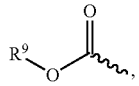

$R^4$ is H, alkyl, (CH$_2$)$_m$C(=O)OH, (CH$_2$)$_m$C(=O)N(H)$R^{11}$, (CH$_2$)$_m$C(=O)$OR^{11}$, (CH$_2$)$_q$OH, (CH$_2$)$_q$OBn, (CH$_2$)$_q$Oallyl, (CH$_2$)$_m$C(=O)N($R^8$)$_2$, or (CH$_2$)$_m$C(=O)N($R^8$)(CH$_2$)$_p$N($R^8$)$_2$;
$R^5$ is H or alkyl;
$R^{6a}$ is H, alkyl, (CH$_2$)$_m$C(=O)OH, (CH$_2$)$_m$C(=O)N(H)$R^{11}$, (CH$_2$)$_m$C(=O)$OR^{11}$, (CH$_2$)$_q$OH, (CH$_2$)$_q$OBn, (CH$_2$)$_q$Oallyl, (CH$_2$)$_m$C(=O)N($R^8$)$_2$, or (CH$_2$)$_m$C(=O)N($R^8$)(CH$_2$)$_p$N($R^8$)$_2$;
$R^{6b}$ is H or alkyl;
provided that one of $R^4$ and $R^{6a}$ is H or alkyl and the other of $R^4$ and $R^{6a}$ is (CH$_2$)$_m$C(=O)OH, (CH$_2$)$_m$C(=O)N(H)$R^{11}$, (CH$_2$)$_m$C(=O)$OR^{11}$, (CH$_2$)$_q$OH, (CH$_2$)$_q$OBn, (CH$_2$)$_q$Oallyl, (CH$_2$)$_m$C(=O)N($R^8$)$_2$, or (CH$_2$)$_m$C(=O)N($R^8$)(CH$_2$)$_p$N($R^8$)$_2$;
$R^7$ is H, C(=O)alkyl, C(=O)(CH$_2$)$_m$(NR$^8$)$_2$, alkyl, aralkyl, or aryl;
each occurrence of $R^8$ is independently H, aryl, or alkyl;
$R^9$ is tert-butyl, allyl, or a group of a formula:

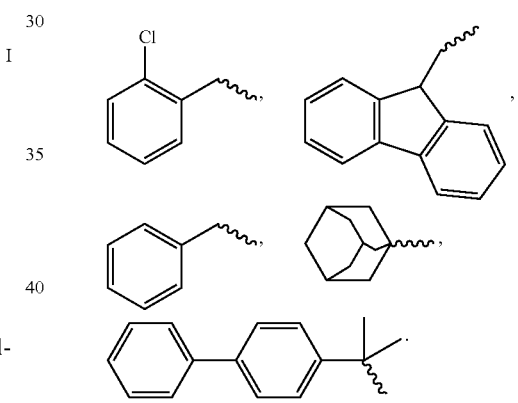

$R^{11}$ is a peptide solid support;
$R^{12}$ is H or a second nitrogen protecting group;
each occurrence of m is an independent integer having a value between 0 and 6;
each occurrence of q is an independent integer having a value between 1 and 6;
p is an integer having a value between 1 and 10; and
y is 0 or 1.

33. The compound of claim 32, wherein y is 1.
34. The compound of claim 32, wherein y is 0.
35. The compound of claim 34, wherein $R^4$ is (CH$_2$)$_m$C(=O)OH, (CH$_2$)$_m$C(=O)N($R^8$)$_2$, (CH$_2$)$_m$C(=O)N(H)$R^{11}$, or (CH$_2$)$_m$C(=O)$OR^{11}$, and $R^{6a}$ is H or alkyl.

* * * * *

UNITED STATES PATENT AND TRADEMARK OFFICE
CERTIFICATE OF CORRECTION

| | | |
|---|---|---|
| PATENT NO. | : 7,964,181 B2 | Page 1 of 1 |
| APPLICATION NO. | : 11/694181 | |
| DATED | : June 21, 2011 | |
| INVENTOR(S) | : Shubh D. Sharma et al. | |

It is certified that error appears in the above-identified patent and that said Letters Patent is hereby corrected as shown below:

In the Claims

Claim 1, Column 127, line 51, delete "$C(=O)(CH_2)_m(NR^8)_2$" and replace with --$C(=O)(CH_2)_mN(R^8)_2$--.

Claim 25, Column 132, line 66, delete "$(CH_2)_mC(=O)N*H)R^{11}$" and replace with --$(CH_2)_mC(=O)N(H)R^{11}$--.

Claim 29, Column 134, line 39, delete "$C(=O)(CH_2)_m(NR^8)_2$" and replace with --$C(=O)(CH_2)_mN(R^8)_2$--.

Signed and Sealed this
Fifteenth Day of July, 2014

Michelle K. Lee
*Deputy Director of the United States Patent and Trademark Office*

```
                        SEQUENCE LISTING

<160> NUMBER OF SEQ ID NOS: 2

<210> SEQ ID NO 1
<211> LENGTH: 15
<212> TYPE: PRT
<213> ORGANISM: Homo sapiens
<220> FEATURE:
<221> NAME/KEY: DOMAIN
<222> LOCATION: (1)..(15)
<223> OTHER INFORMATION: ANP derivative
<220> FEATURE:
<221> NAME/KEY: DISULFID
<222> LOCATION: (2)..(13)
<220> FEATURE:
<221> NAME/KEY: MOD_RES
<222> LOCATION: (15)..(15)
<223> OTHER INFORMATION: AMIDATION

<400> SEQUENCE: 1

Met Cys His Phe Gly Gly Arg Met Asp Arg Ile Ser Cys Tyr Arg
1               5                   10                  15

<210> SEQ ID NO 2
<211> LENGTH: 9
<212> TYPE: PRT
<213> ORGANISM: Homo sapiens
<220> FEATURE:
<221> NAME/KEY: DOMAIN
<222> LOCATION: (1)..(9)
<223> OTHER INFORMATION: oxytocin derivative
<220> FEATURE:
<221> NAME/KEY: DISULFID
<222> LOCATION: (1)..(6)
<220> FEATURE:
<221> NAME/KEY: MOD_RES
<222> LOCATION: (9)..(9)
<223> OTHER INFORMATION: AMIDATION

<400> SEQUENCE: 2

Cys Tyr Ile Gln Asn Cys Pro Leu Gly
1               5
```